US012781219B2

(12) United States Patent
Sontheimer et al.

(10) Patent No.: US 12,781,219 B2
(45) Date of Patent: Nov. 3, 2026

(54) MODIFIED GUIDE RNAS FOR CRISPR GENOME EDITING

(71) Applicant: UNIVERSITY OF MASSACHUSETTS, Boston, MA (US)

(72) Inventors: Erik Joseph Sontheimer, Auburndale, MA (US); Anastasia Khvorova, Westborough, MA (US); Jonathan Kenneth Watts, Worcester, MA (US); Aamir Mir, Worcester, MA (US); Julia Frances Alterman, Worcester, MA (US); Matthew Ryan Hassler, Worcester, MA (US); Michael Harry Brodsky, Sudbury, MA (US); Alexandre Jean-Marie Debacker, Worcester, MA (US)

(73) Assignee: UNIVERSITY OF MASSACHUSETTS, Westborough, MA (US)

( * ) Notice: Subject to any disclaimer, the term of this patent is extended or adjusted under 35 U.S.C. 154(b) by 1251 days.

(21) Appl. No.: 16/981,908

(22) PCT Filed: Mar. 18, 2019

(86) PCT No.: PCT/US2019/022818

§ 371 (c)(1),
(2) Date: Sep. 17, 2020

(87) PCT Pub. No.: WO2019/183000

PCT Pub. Date: Sep. 26, 2019

(65) Prior Publication Data

US 2021/0363518 A1 Nov. 25, 2021

Related U.S. Application Data

(60) Provisional application No. 62/644,944, filed on Mar. 19, 2018.

(51) Int. Cl.

*C12N 15/11* (2006.01)
*C12N 9/22* (2006.01)
*C12N 15/90* (2006.01)

(52) U.S. Cl.

CPC ................ *C12N 15/11* (2013.01); *C12N 9/22* (2013.01); *C12N 15/907* (2013.01); *C12N 2310/20* (2017.05); *C12N 2310/315* (2013.01); *C12N 2310/321* (2013.01); *C12N 2310/322* (2013.01); *C12N 2310/3515* (2013.01); *C12N 2320/52* (2013.01); *C12N 2800/80* (2013.01)

(58) Field of Classification Search

CPC ........ C12N 15/11; C12N 9/22; C12N 15/907; C12N 2310/20; C12N 2310/315; C12N 2310/321; C12N 2310/322; C12N 2320/52; C12N 2800/80

See application file for complete search history.

(56) References Cited

U.S. PATENT DOCUMENTS

2017/0362644 A1 12/2017 Doudna et al.
2018/0015174 A1 1/2018 Irvine et al.
2018/0051281 A1 2/2018 Ryan et al.
2018/0179523 A1* 6/2018 Collingwood ........ C12N 15/111
2019/0048338 A1* 2/2019 Yin .......................... C12N 9/16

FOREIGN PATENT DOCUMENTS

EP 3752632 A1 12/2020
WO WO 2010/056403 A1 5/2010
WO WO 2016/100951 A2 6/2016
WO WO 2016/186745 A1 11/2016
WO WO 2017/004279 A2 1/2017
WO WO 2017/068377 A1 4/2017
WO WO 2017/132669 A1 8/2017
WO WO 2017/136794 A1 8/2017
WO WO 2017/158153 A1 9/2017
WO WO 2018/026976 A1 2/2018
WO WO 2019/183000 A1 9/2019

OTHER PUBLICATIONS

Jiang et al., "A Cas9-guide RNA complex preorganized for target DNA recognition", Science, vol. 348, Published Jun. 16, 2015, pp. 1477-1481. (Year: 2015).*

Rahdar et al., "Synthetic CRISPR RNA-Cas9-guided genome editing in human cells", PNAS, pp. E7110-E7117, Published Nov. 16, 2015. (Year: 2015).*

Anders, et al., "Structural Basis of PAM-Dependent Target DNA Recognition by the Cas9 Endonuclease", Nature, vol. 513, No. 7519, pp. 569-573., Jul. 27, 2014.

Briner, et al., "Guide RNA Functional Modules Direct Cas9 Activity and Orthogonality", Molecular Cell, vol. 56, No. 2, pp. 333-339., Oct. 23, 2014.

Brinkman, et al., "Easy Quantitative Assessment of Genome Editing by Sequence Trace Decomposition", Nucleic Acids Research, vol. 42, Issue 22, pp. 1-8., Dec. 16, 2014.

Chen, et al., "Enhanced Proofreading Governs CRISPR-Cas9 Targeting Accuracy", Nature, vol. 550, pp. 407-410., Sep. 20, 2017.

Gasiunas, et al., "Cas9-crRNA Ribonucleoprotein Complex Mediates Specific DNA Cleavage for Adaptive Immunity in Bacteria", Proceedings of the National Academy of Sciences, vol. 109, No. 39, pp. E2579-E2586., Sep. 4, 2012.

(Continued)

*Primary Examiner* — Abigail Vanhorn
*Assistant Examiner* — Stephanie L Sullivan
(74) *Attorney, Agent, or Firm* — LATHROP GPM LLP; James H. Velema, Esq.

(57) ABSTRACT

Chemically modified crRNAs and tracrRNAs are provided. crRNAs and tracrRNAs with 5' and/or 3' conjugated moieties are provided. crRNAs and tracrRNAs with modifications in the repeat region of the crRNA or the anti-repeat region of the tracrRNA are provided. Methods of using the crRNAs and tracrRNAs for genome editing with a CRISPR nuclease and kits for performing the same are also provided.

27 Claims, 25 Drawing Sheets

Specification includes a Sequence Listing.

(56) References Cited

OTHER PUBLICATIONS

Hsu, et al., "DNA Targeting Specificity of RNA-Guided Cas9 Nucleases", Nature Biotechnology, vol. 31, No. 9, pp. 827-832., Sep. 2013.
Hu, et al., "Evolved Cas9 Variants with Broad PAM Compatibility and High DNA Specificity", Nature, vol. 556, pp. 57-63., Feb. 28, 2018.
International Preliminary Report on Patentability Received for PCT Application No. PCT/US2019/022818, mailed on Sep. 22, 2020, 11 pages.
International Search Report & Written Opinion Received for PCT Application No. PCT/US2019/022818, mailed on Aug. 28, 2019, 16 Pages.
Jiang, et al., "A Cas9-Guide RNA Complex Preorganized for Target DNA Recognition", Science, vol. 348, Issue 6242, pp. 1477-1481., Jun. 26, 2015.
Jiang, et al., "RNA-guided editing of bacterial genomes using CRISPR-Cas systems", Nature biotechnology, vol. 31, No. 3, pp. 233-239., Jan. 29, 2013.
Jiang, et al., "Structures of a CRISPR-Cas9 R-loop Complex Primed for DNA Cleavage", Science, vol. 351, Issue 6275, pp. 867-871., Feb. 19, 2016.
Jinek, et al., "A Programmable Dual-RNA-Guided DNA Endonuclease In Adaptive Bacterial Immunity", Science, vol. 337, No. 6096, pp. 816-821., Aug. 2012.
Kleinstiver, et al., "High-Fidelity CRISPR-Cas9 Nucleases with no Detectable Genome-Wide Off-Target Effects", Nature, vol. 529, No. 7587, pp. 490-495., Jan. 6, 2016.
Lee, et al., "Synthetically Modified Guide RNA and Donor DNA are a Versatile Platform for CRISPR-Cas9 Engineering", eLIFE Genes and Chromosomes Human Biology and Medicine, vol. 6, 17 Pages., May 2, 2017.
Ma, et al., "Correction of a Pathogenic Gene Mutation in Human Embryos", Nature, vol. 548, pp. 413-419., Aug. 2, 2017.
Mali, et al., "RNA-Guided Human Genome Engineering via Cas9", Science, vol. 339, No. 6121, pp. 823-826., Feb. 15, 2013.
Manoharan, et al., "Unique Gene-Silencing and Structural Properties of 2'-Fluoro-Modified siRNAs", Angewandte Chemie International Edition, vol. 50, Issue 10, pp. 2284-2288., Mar. 1, 2011.
Mingozzi, et al., "Immune Responses to AAV vectors: Overcoming Barriers to Successful Gene Therapy", The Journal of the American Society of Hematology, vol. 122, No. 1, pp. 23-36., Jul. 4, 2013.
Nishimasu, et al., "Crystal Structure of Cas9 In Complex With Guide RNA and Target DNA", Cell, vol. 156, No. 5, pp. 935-949., Feb. 27, 2014.
Nishimasu, et al., "Crystal Structure of *Staphylococcus aureus* Cas9", Cell, vol. 162, No. 5, pp. 1113-1126., Aug. 27, 2015.
Patra, et al., "2'-Fluoro RNA Shows Increased Watson-Crick H-Bonding Strength and Stacking Relative to RNA: Evidence from NMR and Thermodynamic Datat", Angewandte Chemie International Edition, vol. 51, Issue 47, pp. 11863-11866., Nov. 19, 2012.
Pils, et al., "Flexible Non-Nucleotide Linkers as Loop Replacements in Short Double Helical RNAs", Nucleic Acids Research, vol. 28, Issue 9, pp. 1859-1863., May 1, 2000.
Slaymaker, et al., "Rationally Engineered Cas9 Nucleases with Improved Specificity", Science, vol. 351, No. 6268, pp. 84-88., Jan. 1, 2016.
Yin, et al., "Structure-Guided Chemical Modification of Guide RNA Enables Potent Non-Viral In Vivo Genome Editing", Nature Biotechnology, vol. 35, No. 12, pp. 1179-1187., Dec. 2017.
Zetsche, et al., "Cpf1 is a Single RNA-Guided Endonuclease of a Class 2 CRISPR-Cas System", Cell, vol. 163, No. 3, pp. 759-771., Oct. 22, 2015.
Extended European Search Report for European Patent Application No. 19771322.5, dated Jun. 14, 2022.
Partial Supplementary European Search Report for European Patent Application No. 19771322.5, dated Mar. 10, 2022.

* cited by examiner

X, Y, Z, M can either be nothing, or one or more of the conjugates from the list below:

| | Identity of X, Y, Z, M | | Identity of X, Y, Z, M |
|---|---|---|---|
| 1 | GalNac | 8 | Lipophillic entities |
| 2 | Chol | 9 | DCA |
| 3 | DHA | 10 | PC-DCA |
| 4 | Vitamins | 11 | PEG |
| 5 | Small molecules | 12 | poloxamer |
| 6 | Aptamers | 13 | Nuclear Localization Signal |
| 7 | Antibodies | 14 | peptides |

SEQUENCE LISTING

```
<160> NUMBER OF SEQ ID NOS: 137

<210> SEQ ID NO 1
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 1

nnnnnnnnnn nnnnnnnnnn guuuuagagc uaugcu                                36
```

```
<210> SEQ ID NO 2
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 2

nnnnnnnnnn nnnnnnnnnn guuuuagagc uaugcu                              36


<210> SEQ ID NO 3
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 3

nnnnnnnnnn nnnnnnnnnn guuuuagagc uaugcu                              36


<210> SEQ ID NO 4
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 4

nnnnnnnnnn nnnnnnnnnn guuuuagagc uaugcu                              36


<210> SEQ ID NO 5
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 5

nnnnnnnnnn nnnnnnnnnn guuuuagagc uaugcu                              36


<210> SEQ ID NO 6
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
```

<223> OTHER INFORMATION: a, c, u, g, unknown or other

<400> SEQUENCE: 6
nnnnnnnnnn nnnnnnnnnn guuuuagagc uaugcu 36

<210> SEQ ID NO 7
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 7
nnnnnnnnnn nnnnnnnnnn guuuuagagc uaugcu 36

<210> SEQ ID NO 8
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 8
nnnnnnnnnn nnnnnnnnnn guuuuagagc uaugcu 36

<210> SEQ ID NO 9
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 9
nnnnnnnnnn nnnnnnnnnn guuuuagagc uaugcu 36

<210> SEQ ID NO 10
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 10
nnnnnnnnnn nnnnnnnnnn guuuuagagc uaugcu 36

<210> SEQ ID NO 11
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 11
nnnnnnnnnn nnnnnnnnnn guuuuagagc uaugcu 36

<210> SEQ ID NO 12
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 12
nnnnnnnnnn nnnnnnnnnn guuuuagagc uaugcu 36

<210> SEQ ID NO 13
<211> LENGTH: 67
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 13
agcauagcaa guuaaaauaa ggcuaguccg uuaucaacuu gaaaaagugg caccgagucg 60
gugcuuu 67

<210> SEQ ID NO 14
<211> LENGTH: 67
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 14
agcauagcaa guuaaaauaa ggcuaguccg uuaucaacuu gaaaaagugg caccgagucg 60
gugcuuu 67

<210> SEQ ID NO 15
<211> LENGTH: 67
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 15
agcauagcaa guuaaaauaa ggcuaguccg uuaucaacuu gaaaaagugg caccgagucg 60
gugcuuu 67

<210> SEQ ID NO 16
<211> LENGTH: 67
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 16
agcauagcaa guuaaaauaa ggcuaguccg uuaucaacuu gaaaaagugg caccgagucg 60
gugcuuu 67

<210> SEQ ID NO 17
<211> LENGTH: 67
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 17
agcauagcaa guuaaaauaa ggcuaguccg uuaucaacuu gaaaaagugg caccgagucg 60
gugcuuu 67

<210> SEQ ID NO 18
<211> LENGTH: 67
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 18
agcauagcaa guuaaaauaa ggcuaguccg uuaucaacuu gaaaaagugg caccgagucg 60
gugcuuu 67

<210> SEQ ID NO 19
<211> LENGTH: 67
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 19
agcauagcaa guuaaaauaa ggcuaguccg uuaucaacuu gaaaaagugg caccgagucg 60
gugcuuu 67

<210> SEQ ID NO 20
<211> LENGTH: 67
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 20
agcauagcaa guuaaaauaa ggcuaguccg uuaucaacuu gaaaaagugg caccgagucg 60
gugcuuu 67

<210> SEQ ID NO 21
<211> LENGTH: 67
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 21
agcauagcaa guuaaaauaa ggcuaguccg uuaucaacuu gaaaaagugg caccgagucg 60
gugcuuu 67

<210> SEQ ID NO 22
<211> LENGTH: 67
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 22
agcauagcaa guuaaaauaa ggcuaguccg uuaucaacuu gaaaaagugg caccgagucg 60
gugcuuu 67

<210> SEQ ID NO 23
<211> LENGTH: 67
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 23
agcauagcaa guuaaaauaa ggcuaguccg uuaucaacuu gaaaaagugg caccgagucg 60
gugcuuu 67

<210> SEQ ID NO 24
<211> LENGTH: 67
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 24
agcauagcaa guuaaaauaa ggcuaguccg uuaucaacuu gaaaaagugg caccgagucg 60
gugcuuu 67

<210> SEQ ID NO 25
<211> LENGTH: 67
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 25
agcauagcaa guuaaaauaa ggcuaguccg uuaucaacuu gaaaaagugg caccgagucg 60
gugcuuu 67

<210> SEQ ID NO 26
<211> LENGTH: 67
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 26
agcauagcaa guuaaaauaa ggcuaguccg uuaucaacuu gaaaaagugg caccgagucg 60
gugcuuu 67

<210> SEQ ID NO 27
<211> LENGTH: 67
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 27
agcauagcaa guuaaaauaa ggcuaguccg uuaucaacuu gaaaaagugg caccgagucg 60
gugcuuu 67

<210> SEQ ID NO 28
<211> LENGTH: 67
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 28
agcauagcaa guuaaaauaa ggcuaguccg uuaucaacuu gaaaaagugg caccgagucg 60
gugcuuu 67

<210> SEQ ID NO 29
<211> LENGTH: 67
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 29
agcauagcaa guuaaaauaa ggcuaguccg uuaucaacuu gaaaaagugg caccgagucg 60
gugcuuu 67

<210> SEQ ID NO 30
<211> LENGTH: 67
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 30
agcauagcaa guuaaaauaa ggcuaguccg uuaucaacuu gaaaaagugg caccgagucg 60
gugcuuu 67

<210> SEQ ID NO 31
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 31
nnnnnnnnnn nnnnnnnnnn guuuuagagc gagcgc 36

<210> SEQ ID NO 32
<211> LENGTH: 67
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 32
gcgcucgcaa guuaaaauaa ggcuaguccg uuaucaacuu gaaaaagugg caccgagucg 60
gugcuuu 67

<210> SEQ ID NO 33
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 33
nnnnnnnnnn nnnnnnnnnn guuuuagagc gagcgc 36

<210> SEQ ID NO 34
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 34
nnnnnnnnnn nnnnnnnnnn guuuuagagc gagcgc 36

<210> SEQ ID NO 35
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 35
nnnnnnnnnn nnnnnnnnnn guuuuagagc gagcgc 36

<210> SEQ ID NO 36
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 36
nnnnnnnnnn nnnnnnnnnn guuuuagagc gagcgc 36

<210> SEQ ID NO 37
<211> LENGTH: 67
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 37
gcgcucgcaa guuaaaauaa ggcuaguccg uuaucaacuu gaaaaagugg caccgagucg 60
gugcuuu 67

<210> SEQ ID NO 38
<211> LENGTH: 67
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 38
gcgcucgcaa guuaaaauaa ggcuaguccg uuaucaacuu gaaaaagugg caccgagucg 60
gugcuuu 67

<210> SEQ ID NO 39
<211> LENGTH: 67
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 39
gcgcucgcaa guuaaaauaa ggcuaguccg uuaucaacuu gaaaaagugg caccgagucg 60
gugcuuu 67

<210> SEQ ID NO 40
<211> LENGTH: 67
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 40
gcgcucgcaa guuaaaauaa ggcuaguccg uuaucaacuu gaaaaagugg caccgagucg 60
gugcuuu 67

<210> SEQ ID NO 41
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 41
ggugagcucu uauuugcgua guuuuagagc uaugcu 36

<210> SEQ ID NO 42

```
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42

ggugagcucu uauuugcgua guuuuagagc uaugcu                              36


<210> SEQ ID NO 43
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43

ggugagcucu uauuugcgua guuuuagagc uaugcu                              36


<210> SEQ ID NO 44
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44

ggugagcucu uauuugcgua guuuuagagc uaugcu                              36


<210> SEQ ID NO 45
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45

ggugagcucu uauuugcgua guuuuagagc uaugcu                              36


<210> SEQ ID NO 46
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46

ggugagcucu uauuugcgua guuuuagagc uaugcu                              36


<210> SEQ ID NO 47
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47

ggugagcucu uauuugcgua guuuuagagc uaugcu                              36


<210> SEQ ID NO 48
<211> LENGTH: 36
```

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 48
ggugagcucu uauuugcgua guuuuagagc uaugcu 36

<210> SEQ ID NO 49
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 49
ggugagcucu uauuugcgua guuuuagagc uaugcu 36

<210> SEQ ID NO 50
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 50
ggugagcucu uauuugcgua guuuuagagc uaugcu 36

<210> SEQ ID NO 51
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 51
ggugagcucu uauuugcgua guuuuagagc uaugcu 36

<210> SEQ ID NO 52
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 52
ggugagcucu uauuugcgua guuuuagagc uaugcu 36

<210> SEQ ID NO 53
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 53
ggugagcucu uauuugcgua guuuuagagc uaugcu 36

<210> SEQ ID NO 54
<211> LENGTH: 36
<212> TYPE: RNA

<213> ORGANISM: Artificial Sequence
<220> FEATURE:
<223> OTHER INFORMATION: Description of Artificial Sequence: Synthetic oligonucleotide

<400> SEQUENCE: 54
ggugagcucu uauuugcgua guuuuagagc uaugcu 36

<210> SEQ ID NO 55
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 55
ggugagcucu uauuugcgua guuuuagagc uaugcu 36

<210> SEQ ID NO 56
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 56
ggugagcucu uauuugcgua guuuuagagc uaugcu 36

<210> SEQ ID NO 57
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 57
ggugagcucu uauuugcgua guuuuagagc uaugcu 36

<210> SEQ ID NO 58
<211> LENGTH: 67
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 58
agcauagcaa guuaaaauaa ggcuaguccg uuaucaacuu gaaaaagugg caccgagucg 60
gugcuuu 67

<210> SEQ ID NO 59
<211> LENGTH: 67
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 59
agcauagcaa guuaaaauaa ggcuaguccg uuaucaacuu gaaaaagugg caccgagucg 60
gugcuuu 67

<210> SEQ ID NO 60
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 60
ggugagcucu uauuugcgua guuuuagagc gagcgc 36

<210> SEQ ID NO 61
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 61
ggugagcucu uauuugcgua guuuuagagc gagcgc 36

<210> SEQ ID NO 62
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 62
ggugagcucu uauuugcgua guuuuagagc gagcgc 36

<210> SEQ ID NO 63
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 63
ggugagcucu uauuugcgua guuuuagagc gagcgc 36

<210> SEQ ID NO 64
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 64
ggugagcucu uauuugcgua guuuuagagc uaugcu 36

<210> SEQ ID NO 65
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 65
ggugagcucu uauuugcgua guuuuagagc uaugcu 36

<210> SEQ ID NO 66

<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 66
ggugagcucu uauuugcgua guuuuagagc uaugcu 36

<210> SEQ ID NO 67
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 67
ggugagcucu uauuugcgua guuuuagagc uaugcu 36

<210> SEQ ID NO 68
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 68
ggugagcucu uauuugcgua guuuuagagc uaugcu 36

<210> SEQ ID NO 69
<211> LENGTH: 67
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 69
gcgcucgcaa guuaaaauaa ggcuaguccg uuaucaacuu gaaaaagugg caccgagucg 60
gugcuuu 67

<210> SEQ ID NO 70
<211> LENGTH: 67
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 70
gcgcucgcaa guuaaaauaa ggcuaguccg uuaucaacuu gaaaaagugg caccgagucg 60
gugcuuu 67

<210> SEQ ID NO 71
<211> LENGTH: 67
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 71
gcgcucgcaa guuaaaauaa ggcuaguccg uuaucaacuu gaaaaagugg caccgagucg 60
gugcuuu 67

<210> SEQ ID NO 72
<211> LENGTH: 67
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 72
gcgcucgcaa guuaaaauaa ggcuaguccg uuaucaacuu gaaaaagugg caccgagucg 60
gugcuuu 67

<210> SEQ ID NO 73
<211> LENGTH: 67
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 73
gcgcucgcaa guuaaaauaa ggcuaguccg uuaucaacuu gaaaaagugg caccgagucg 60
gugcuuu 67

<210> SEQ ID NO 74
<211> LENGTH: 67
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 74
gcgcucgcaa guuaaaauaa ggcuaguccg uuaucaacuu gaaaaagugg caccgagucg 60
gugcuuu 67

<210> SEQ ID NO 75
<211> LENGTH: 67
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 75
gcgcucgcaa guuaaaauaa ggcuaguccg uuaucaacuu gaaaaagugg caccgagucg 60
gugcuuu 67

<210> SEQ ID NO 76
<211> LENGTH: 67
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 76
gcgcucgcaa guuaaaauaa ggcuaguccg uuaucaacuu gaaaaagugg caccgagucg 60
gugcuuu 67

<210> SEQ ID NO 77
<211> LENGTH: 67
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 77
gcgcucgcaa guuaaaauaa ggcuaguccg uuaucaacuu gaaaaagugg caccgagucg 60
gugcuuu 67

<210> SEQ ID NO 78
<211> LENGTH: 67
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 78
gcgcucgcaa guuaaaauaa ggcuaguccg uuaucaacuu gaaaaagugg caccgagucg 60
gugcuuu 67

<210> SEQ ID NO 79
<211> LENGTH: 67
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 79
gcgcucgcaa guuaaaauaa ggcuaguccg uuaucaacuu gaaaaagugg caccgagucg 60
gugcuuu 67

<210> SEQ ID NO 80
<211> LENGTH: 67
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 80
gcgcucgcaa guuaaaauaa ggcuaguccg uuaucaacuu gaaaaagugg caccgagucg 60
gugcuuu 67

<210> SEQ ID NO 81
<211> LENGTH: 67
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 81
gcgcucgcaa guuaaaauaa ggcuaguccg uuaucaacuu gaaaaagugg caccgagucg 60
gugcuuu 67

<210> SEQ ID NO 82
<211> LENGTH: 67
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 82
gcgcucgcaa guuaaaauaa ggcuaguccg uuaucaacuu gaaaaagugg caccgagucg 60
gugcuuu 67

<210> SEQ ID NO 83
<211> LENGTH: 67
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 83
gcgcucgcaa guuaaaauaa ggcuaguccg uuaucaacuu gaaaaagugg caccgagucg 60
gugcuuu 67

<210> SEQ ID NO 84
<211> LENGTH: 67
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 84
gcgcucgcaa guuaaaauaa ggcuaguccg uuaucaacuu gaaaaagugg caccgagucg 60
gugcuuu 67

<210> SEQ ID NO 85
<211> LENGTH: 67
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 85
gcgcucgcaa guuaaaauaa ggcuaguccg uuaucaacuu gaaaaagugg caccgagucg 60
gugcuuu 67

<210> SEQ ID NO 86
<211> LENGTH: 67
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 86
gcgcucgcaa guuaaaauaa ggcuaguccg uuaucaacuu gaaaaagugg caccgagucg 60
gugcuuu 67

<210> SEQ ID NO 87
<211> LENGTH: 67
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 87
gcgcucgcaa guuaaaauaa ggcuaguccg uuaucaacuu gaaaaagugg caccgagucg 60
gugcuuu 67

<210> SEQ ID NO 88
<211> LENGTH: 67
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 88
gcgcucgcaa guuaaaauaa ggcuaguccg uuaucaacuu gaaaaagugg caccgagucg 60
gugcuuu 67

<210> SEQ ID NO 89
<211> LENGTH: 67
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 89
gcgcucgcaa guuaaaauaa ggcuaguccg uuaucaacuu gaaaaagugg caccgagucg 60
gugcuuu 67

<210> SEQ ID NO 90
<211> LENGTH: 67
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 90
gcgcucgcaa guuaaaauaa ggcuaguccg uuaucaacuu gaaaaagugg caccgagucg 60
gugcuuu 67

<210> SEQ ID NO 91
<211> LENGTH: 67
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 91
gcgcucgcaa guuaaaauaa ggcuaguccg uuaucaacuu gaaaaagugg caccgagucg 60
gugcuuu 67

<210> SEQ ID NO 92
<211> LENGTH: 67
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 92
gcgcucgcaa guuaaaauaa ggcuaguccg uuaucaacuu gaaaaagugg caccgagucg 60
gugcuuu 67

<210> SEQ ID NO 93
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 93
ggugagcucu uauuugcgua guuuuagagc gagcgc 36

<210> SEQ ID NO 94
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 94
ggugagcucu uauuugcgua guuuuagagc gagcgc 36

<210> SEQ ID NO 95
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 95
ggugagcucu uauuugcgua guuuuagagc gagcgc 36

<210> SEQ ID NO 96
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 96
ggugagcucu uauuugcgua guuuuagagc gagcgc 36

<210> SEQ ID NO 97
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 97
ggugagcucu uauuugcgua guuuuagagc gagcgc 36

<210> SEQ ID NO 98
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 98
ggugagcucu uauuugcgua guuuuagagc gagcgc 36

<210> SEQ ID NO 99
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 99
ggugagcucu uauuugcgua guuuuagagc gagcgc 36

<210> SEQ ID NO 100
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 100
ggugagcucu uauuugcgua guuuuagagc gagcgc 36

<210> SEQ ID NO 101
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 101
ggugagcucu uauuugcgua guuuuagagc gagcgc 36

<210> SEQ ID NO 102
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 102
ggugagcucu uauuugcgua guuuuagagc gagcgc 36

<210> SEQ ID NO 103
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 103
ggugagcucu uauuugcgua guuuuagagc gagcgc 36

<210> SEQ ID NO 104
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 104
ggugagcucu uauuugcgua guuuuagagc gagcgc 36

<210> SEQ ID NO 105
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 105
ggugagcucu uauuugcgua guuuuagagc gagcgc 36

<210> SEQ ID NO 106
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 106
ggugagcucu uauuugcgua guuuuagagc gagcgc 36

<210> SEQ ID NO 107
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 107
ggugagcucu uauuugcgua guuuuagagc gagcgc 36

<210> SEQ ID NO 108
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 108
ggugagcucu uauuugcgua guuuuagagc gagcgc 36

<210> SEQ ID NO 109
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 109
ggugagcucu uauuugcgua guuuuagagc gagcgc 36

<210> SEQ ID NO 110
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 110
ggugagcucu uauuugcgua guuuuagagc gagcgc 36

<210> SEQ ID NO 111
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 111
ggugagcucu uauuugcgua guuuuagagc gagcgc 36

<210> SEQ ID NO 112
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 112
ggugagcucu uauuugcgua guuuuagagc gagcgc 36

<210> SEQ ID NO 113
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 113
ggugagcucu uauuugcgua guuuuagagc gagcgc 36

<210> SEQ ID NO 114
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 114
ggugagcucu uauuugcgua guuuuagagc gagcgc 36

<210> SEQ ID NO 115
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 115
ggugagcucu uauuugcgua guuuuagagc gagcgc 36

<210> SEQ ID NO 116
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 116
ggugagcucu uauuugcgua guuuuagagc gagcgc 36

<210> SEQ ID NO 117

```
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117

ugaagugcac acaguagaug guuuuagagc uaugcu                              36


<210> SEQ ID NO 118
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118

ugaagugcac acaguagaug guuuuagagc gagcgc                              36


<210> SEQ ID NO 119
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119

ugaagugcac acaguagaug guuuuagagc uaugcu                              36


<210> SEQ ID NO 120
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120

ggugagcucu uauuugcgua guuuuagagc uaugcu                              36


<210> SEQ ID NO 121
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121

cuugccccac agggcaguaa guuuuagagc uaugcu                              36


<210> SEQ ID NO 122
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122

ccugccccac agggcaguaa guuuuagagc uaugcu                              36


<210> SEQ ID NO 123
<211> LENGTH: 36
```

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 123
ugaagugcac acaguagaug guuuuagagc uaugcu 36

<210> SEQ ID NO 124
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 124
ugaagugcac acaguagaug guuuuagagc uaugcu 36

<210> SEQ ID NO 125
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 125
ggugagugag ugugugcgug guuuuagagc uaugcu 36

<210> SEQ ID NO 126
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 126
ggugagugag ugugugcgug guuuuagagc uaugcu 36

<210> SEQ ID NO 127
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 127
ggugagugag ugugugcgug guuuuagagc uaugcu 36

<210> SEQ ID NO 128
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 128
nnnnnnnnnn nnnnnnnnnn guuuuagagc uaugcu 36

<210> SEQ ID NO 129
<211> LENGTH: 67
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 129
agcauagcaa guuaaaauaa ggcuaguccg uuaucaacuu gaaaaagugg caccgagucg 60
gugcuuu 67

<210> SEQ ID NO 130
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 130
ggugagcucu uauuugcgua guuuuagagc uaugcu 36

<210> SEQ ID NO 131
<211> LENGTH: 67
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 131
agcauagcaa guuaaaauaa ggcuaguccg uuaucaacuu gaaaaagugg caccgagucg 60
gugcuuu 67

<210> SEQ ID NO 132
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 132
ggugagcucu uauuugcgua guuuuagagc uaugcu 36

<210> SEQ ID NO 133
<211> LENGTH: 67
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 133
agcauagcaa guuaaaauaa ggcuaguccg uuaucaacuu gaaaaagugg caccgagucg 60
gugcuuu 67

<210> SEQ ID NO 134
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide -continued

```
<400> SEQUENCE: 134

ggugagcucu uauuugcgua guuuuagagc uaugcu                          36


<210> SEQ ID NO 135
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135

agcauagcaa guuaaaauaa ggcuaguccg uuaucaacuu gaaaaagugg caccgagucg    60

gugcuuu                                                              67


<210> SEQ ID NO 136
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136

ggugagcucu uauuugcgua guuuuagagc uaugcu                          36


<210> SEQ ID NO 137
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137

agcauagcaa guuaaaauaa ggcuaguccg uuaucaacuu gaaaaagugg caccgagucg    60

gugcuuu                                                              67
```

MODIFIED GUIDE RNAS FOR CRISPR GENOME EDITING

CROSS-REFERENCE TO RELATED APPLICATIONS

This application is a 35 U.S.C. § 371 filing of International Patent Application No. PCT/US2019/022408, filed Mar. 15, 209, which claims priority to U.S. Provisional Patent Application No. 62/644,944, filed Mar. 19, 2018, the contents of which are incorporated herein in their entirety.

SEQUENCE LISTING

The instant application contains a Sequence Listing which has been submitted electronically in ASCII format and is hereby incorporated by reference in its entirety. Said ASCII copy, created on Sep. 17, 2020, is named 708838_UM9-233US_ST25.txt and is 38,295 bytes in size.

FIELD OF THE INVENTION

This disclosure relates to compositions and methods of modified guide RNAs for CRISPR genome editing.

BACKGROUND

CRISPR RNA-guided genome engineering has revolutionized research into human genetic disease and many other aspects of biology. Numerous CRISPR-based in vivo or ex vivo genome editing therapies are nearing clinical trials. At the heart of this revolution are the microbial effector proteins found in class II CRISPR-Cas systems such as Cas9 (type II) and Cas12a/Cpf1 (type V) (Jinek et al. Science 337, 816-821 (2012); Gasiunas et al. PNAS 109, E2579-E2586 (2012); Zetsche et al. Cell 163, 759-771 (2015)).

The most widely used genome editing tool is the type II-A Cas9 from *Streptococcus pyogenes* strain SF370 (SpCas9) (Jinek et al, supra). Cas9 forms a ribonucleoprotein (RNP) complex with a CRISPR RNA (crRNA) and a trans-activating crRNA (tracrRNA) for efficient DNA cleavage both in bacteria and eukaryotes (FIG. 1). The crRNA contains a guide sequence that directs the Cas9 RNP to a specific locus via base-pairing with the target DNA to form an R-loop. This process requires the prior recognition of a protospacer adjacent motif (PAM), which for SpCas9 is NGG. R-loop formation activates the His-Asn-His (HNH) and RuvC-like endonuclease domains that cleave the target strand and the non-target strand of the DNA, respectively, resulting in a double-strand break (DSB).

For mammalian applications, Cas9 and its guide RNAs can be expressed from DNA (e.g. a viral vector), RNA (e.g. Cas9 mRNA plus guide RNAs in a lipid nanoparticle), or introduced as a ribonucleoprotein (RNP). Viral delivery of Cas9 results in efficient editing, but can be problematic because long-term expression of Cas9 and its guides can result in off-target editing, and viral vectors can elicit strong host immune responses (Mingozzi et al. Blood 122, 23-36 (2013)). RNA and RNP delivery platforms of Cas9 are suitable alternatives to viral vectors for many applications and have recently been shown to be effective genome editing tools in vivo (Yin et al. Nature Biotechnology 35, 1179 (2017); Lee et al. eLife 6, e25312 (2017)). RNP delivery of Cas9 also bypasses the requirement for Cas9 expression, leading to faster editing. Furthermore, Cas9 delivered as mRNA or RNP exists only transiently in cells and therefore exhibits reduced off-target editing. For instance, Cas9 RNPs were successfully used to correct hypertrophic cardiomyopathy (HCM) in human embryos without measurable off-target effects (Ma et al. Nature 548, 413 (2017).

The versatility of Cas9 for genome editing derives from its RNA-guided nature. The crRNA of SpCas9 usually includes a 20 nucleotide guide region followed by a 16 nucleotide repeat region (FIG. 1). The tracrRNA consists of an anti-repeat region that pairs with the crRNA, and also includes three stem-loops. All of these secondary structure elements are required for efficient editing in mammalian systems (Hsu et al. Nature Biotechnology 31, 827 (2013). Nevertheless, existing guide RNAs suffer from several limitations which limit their utility in therapeutic applications. For example, existing guide RNAs may be subject to rapid degradation in circulation and within cells. Moreover, chemical modifications of guide RNAs may reduce stability and editing efficiency. Accordingly, there exists a need in the art for optimized guide RNAs that retain efficient genome editing activity in vivo and ex vivo when paired with a CRISPR nuclease, such as Cas9.

SUMMARY

The present disclosure provides chemically modified guide RNAs for CRISPR genome editing. In certain embodiments, the guide RNAs of the disclosure are heavily or fully chemically modified. The guide RNA of the disclosure may confer several advantages in vivo or ex vivo, including stability, improved potency, and/or reduced off-target effects. Furthermore, in certain embodiments, the modified RNAs of the disclosure have reduced immunogenicity, e.g., a reduced ability to induce innate immune responses.

In certain aspects, the disclosure provides a chemically modified guide RNA comprising: (a) a crRNA portion comprising (i) a guide sequence capable of hybridizing to a target polynucleotide sequence, and (ii) a repeat sequence; and (b) a tracrRNA portion comprising an anti-repeat nucleotide sequence that is complementary to the repeat sequence, wherein the chemically modified guide RNA comprises at least 80% modified nucleotides.

In an embodiment, the one or more modified nucleotides each independently comprise a modification of a ribose group, a phosphate group, a nucleobase, or a combination thereof.

In an embodiment, each modification of the ribose group is independently selected from the group consisting of 2'-O-methyl, 2'-fluoro, 2'-deoxy, 2'-O-(2-methoxyethyl) (MOE), 2'-$NH_2$, a bicyclic nucleotide, a locked nucleic acid (LNA), a 2'-(S)-constrained ethyl (S-cEt), a constrained MOE, or a 2'-0,4'-C-aminomethylene bridged nucleic acid (2',4'-$BNA^{NC}$).

In an embodiment, at least 80% of the ribose groups are chemically modified.

In an embodiment, each modification of the phosphate group is independently selected from the group consisting of a phosphorothioate, phosphonoacetate (PACE), thiophosphonoacetate (thioPACE), amide, triazole, phosphonate, or phosphotriester modification.

In an embodiment, each modification of the nucleobase group is independently selected from the group consisting of 2-thiouridine, 4-thiouridine, $N^6$-methyladenosine, pseudouridine, 2,6-diaminopurine, inosine, thymidine, 5-methylcytosine, 5-substituted pyrimidine, isoguanine, isocytosine, or halogenated aromatic groups.

In an embodiment, the guide RNA comprises at least 90% modified nucleotides.

In an embodiment, the guide RNA comprises 100% modified nucleotides.

In an embodiment, a plurality of the nucleotides at positions 1-10, 20-21, and 27-36 from the 5' end of the crRNA portion each comprise a 2'-O-methyl chemical modification.

In an embodiment, a plurality of the nucleotides at positions 11-14, 17-18, and 25-26 from the 5' end of the crRNA portion each comprise a 2'-fluoro chemical modification.

In an embodiment, a plurality of the nucleotides at positions 1-11, 14, 16-17, 19-22, 25, 29 and 33-67 from the 5' end of the tracrRNA portion each comprise a 2'-O-methyl chemical modification.

In an embodiment, a plurality of the nucleotides at positions 18, 23-24, and 27-28 from the 5' end of the tracrRNA portion each comprise a 2'-fluoro chemical modification.

In an embodiment, a plurality of the nucleotides at positions 11-19 and 22-26 from the 5' end of the crRNA portion each comprise a 2'-fluoro chemical modification.

In an embodiment, a plurality of the nucleotides at positions 12-13, 15, 18, 23-24, 27-28, and 30-32 from the 5' end of the tracrRNA portion each comprise a 2'-fluoro chemical modification.

In an embodiment, a guide RNA modification pattern is selected from the group consisting of:

mN#mN#mN#mNmNmNmNmNmNmNmNrNrNrNrNrNm NmNmNrN mNmGrUrUrUmUmAmGmAmGmCmU-mAmU# mG#mCmU (crRNA 1) (SEQ ID NO: 1);

mN#mN#mN#mNmNmNmNmNmNmNmNrNrNrNrNrN mNmNrNm NmGrUrUrUrAmGmAmGmCmUmAmU#mG#m C#mU (crRNA 7) (SEQ ID NO: 2);

mN#mN#mN#mNmNmNmNmNmNmNmNrNrNrNrNr NrNrNrNmN mGrUrUrUmUmAmGmAmGmCmUmAmU#mG#m C#mU (crRNA 8) (SEQ ID NO: 3);

mN#mN#mN#mNmNmNmNmNmNmNmNrNrNrNrNrN#r N#rNrNrN#mNmGrU#rU#rU#mUmAmGmAmGm CmUmAmU#mG#mC#mU (crRNA 9) (SEQ ID NO: 4);

mN#mN#mN#mNmNmNmNmNmNmNmNfNfNfNfNrN# rN#fNfNrN#mNmGrU#rU#rU#mUmAmGmAmGm CmUmAmU#mG#mC#mU (crRNA 10) (SEQ ID NO: 5);

mN#mN#mN#mNmNmNmNmNmNmNmNfNfNfNfNrN# rN#rN#rN#rN#mNmGrU#rU#rU#mUmAmGmAmGm CmUmAmU#mG#mC#mU (crRNA 11) (SEQ ID NO: 6);

mN#mN#mN#mNmNmNmNmNmNmNmNfNfNfNfNrN#r N#fNfNrN#mNmGrU#rU#rU#mUrA#mGmAmGm CmUmAmU#mG#mC#mU (crRNA 17) (SEQ ID NO: 7);

mN#mN#mN#mNmNmNmNmNmNmNmNfNfNfNfNrN# rN#fNfNrN#mNmGrU#rU#rU#rU#mAmGmAmGm CmUmAmU#mG#mC#mU (crRNA 18) (SEQ ID NO: 8);

mN#mN#mN#mNmNmNmNmNmNmNfNfNfNfNrN# rN#fNfNrN#mNmGrU#rU#rU#rU#rA#mGmAmGm CmUmAmU#mG#mC#mU (crRNA 19) (SEQ ID NO: 9);

mN#mN#mN#mNmNmNmNmNmNmNmNfNfNfNfNrN# rN#fNfNrN#mNmGrU#rU#rU#fUfAmGmAmGmCm UmAmU#mG#mC#mU (crRNA 20) (SEQ ID NO: 10);

mN#mN#mN#mNmNmNmNmNmNmNmNfNfNfNfNfNfN fNfNfNmN mGfUfUfUfUfAmGmAmGmCmUmAmU#mG#mC# mU (crRNA 21) (SEQ ID NO: 11);

mN#mN#mN#mNmNmNmNmNmNmNmNfNfNfNfNrN# rN#fNfNrN#mNmGfUrU#fUfUfAmGmAmGmCm UmAmU#mG#mC#mU (crRNA 22) (SEQ ID NO: 12);

mA#mG#mC#mAmUmAmGmCmAmAmGrUrUmAr AmAmArUm AmAmGmGrCrUmArGrUrCmCrGrU-rUmAmUmCmAmAmCmUmUmGmAmAmA mAmAmGmUmGmGmCmAmCmCmGmAmGm UmCmGmGmUmGmC#mU#mU#mU (tracrRNA 2) (SEQ ID NO: 13);

mA#mG#mC#mAmUmAmGmCmAmAmGrU#rU#m ArA#mAmAr U#mAmAmGmGrC#rU#mArG#rU#rC#mCrG#rU#r U#mAmUmCmAmAmCmUmU mGmAmAmA-mAmGmUmGmGmCmAmCmCmGmAmG-mUmCmGmGmUmG mC#mU#mU#mU (tracrRNA 3) (SEQ ID NO: 14);

mA#mG#mC#mAmUmAmGmCmAmAmGrUrUmAm AmAmArUm AmAmGmGrCrUmArGrUrCmCrGrU-rUmAmUmCmAmAmCmUmUmGmAmAmA mAmAmGmUmGmGmCmAmCmCmGmAmGmUm CmGmGmUmGmC#mU#mU#mU (tracrRNA 4) (SEQ ID NO: 15);

mA#mG#mC#mAmUmAmGmCmAmAmGrUrUmAr AmAmAfUm AmAmGmGfCfUmArGfUfCmCrGrU-rUmAmUmCmAmAmCmUmUmGmAmAmA mAmAmGmUmGmGmCmAmCmCmGmAmGm UmCmGmGmUmGmC#mU#mU#mU (tracrRNA 6) (SEQ ID NO: 16);

mA#mG#mC#mAmUmAmGmCmAmAmGrUfUmAr AmAmAfUm AmAmGmGfCfUmAfGfUfCmCrGrU-rUmAmUmCmAmAmCmUmUmGmAmAmA mAmAmGmUmGmGmCmAmCmCmGmAmGmUm CmGmGmUmGmC#mU#mU#mU (tracrRNA 7) (SEQ ID NO: 17);

mA#mG#mC#mAmUmAmGmCmAmAmGfUfUmAf AmAmAfUm AmAmGmGfCfUmAfGfUfCmCfGfU-fUmAmUmCmAmAmCmUmUmGmAmAmA mAmAmGmUmGmGmCmAmCmCmGmAmGmUm CmGmGmUmGmC#mU#mU#mU (tracrRNA 8) (SEQ ID NO: 18);

mA#mG#mC#mAmUmAmGmCmAmAmGfUrUmAr AmAmArUm AmAmGmGrCrUmArGrUrCmCrGrU-rUmAmUmCmAmAmCmUmUmGmAmAmA mAmAmGmUmGmGmCmAmCmCmGmAmGmUm CmGmGmUmGmC#mU#mU#mU (tracrRNA 9) (SEQ ID NO: 19);

mA#mG#mC#mAmUmAmGmCmAmAmGrUfUmAr AmAmArUm AmAmGmGrCrUmArGrUrCmCrGrU-rUmAmUmCmAmAmCmUmUmGmAmAmA mAmAmGmUmGmGmCmAmCmCmGmAmGmUm CmGmGmUmGmC#mU#mU#mU (tracrRNA 10) (SEQ ID NO: 20);

mA#mG#mC#mAmUmAmGmCmAmAmGrUrUmAf AmAmArUm AmAmGmGrCrUmArGrUrCmCrGrU-rUmAmUmCmAmAmCmUmUmGmAmAmA mAmAmGmUmGmGmCmAmCmCmGmAmGmUm CmGmGmUmGmC#mU#mU#mU (tracrRNA 11) (SEQ ID NO: 21);

mA#mG#mC#mAmUmAmGmCmAmAmGrUrUmAr AmAmAfUm AmAmGmGrCrUmArGrUrCmCrGrU-rUmAmUmCmAmAmCmUmUmGmAmAmA mAmAmGmUmGmGmCmAmCmCmGmAmGmUm CmGmGmUmGmC#mU#mU#mU (tracrRNA 12) (SEQ ID NO: 22);

mA#mG#mC#mAmUmAmGmCmAmAmGrUrUmAr AmAmArUm AmAmGmGfCrUmArGrUrCmCrGrU-rUmAmUmCmAmAmCmUmUmGmAmAmA mAmAmGmUmGmGmCmAmCmCmGmAmGmUm CmGmGmUmGmC#mU#mU#mU (tracrRNA 13) (SEQ ID NO: 23);

mA#mG#mC#mAmUmAmGmCmAmAmGrUrUmAr AmAmArUm AmAmGmGrCfUmArGrUrCmCrGrU-rUmAmUmCmAmAmCmUmUmGmAmAmA mAmAmGmUmGmGmCmAmCmCmGmAmGmUm CmGmGmUmGmC#mU#mU#mU (tracrRNA 14) (SEQ ID NO: 24);

mA#mG#mC#mAmUmAmGmCmAmAmGrUrUmAr AmAmArUm AmAmGmGrCrUmAfGrUrCmCrGrU-rUmAmUmCmAmAmCmUmUmGmAmAmA mAmAmGmUmGmGmCmAmCmCmGmAmGm UmCmGmGmUmGmC#mU#mU#mU (tracrRNA 15) (SEQ ID NO: 25);

mA#mG#mC#mAmUmAmGmCmAmAmGrUrUmAr AmAmArUm AmAmGmGrCrUmArGfUrCmCrGrU-rUmAmUmCmAmAmCmUmUmGmAmAmA mAmAmGmUmGmGmCmAmCmCmGmAmGmUm CmGmGmUmGmC#mU#mU#mU (tracrRNA 16) (SEQ ID NO: 26);

mA#mG#mC#mAmUmAmGmCmAmAmGrUrUmAr AmAmArUm AmAmGmGrCrUmArGrUfCmCrGrU-rUmAmUmCmAmAmCmUmUmGmAmAmA mAmAmGmUmGmGmCmAmCmCmGmAmGmUm CmGmGmUmGmC#mU#mU#mU (tracrRNA 17) (SEQ ID NO: 27);

mA#mG#mC#mAmUmAmGmCmAmAmGrUrUmAr AmAmArUm AmAmGmGrCrUmArGrUrCmCfGrU-rUmAmUmCmAmAmCmUmUmGmAmAmA mAmAmGmUmGmGmCmAmCmCmGmAmGmUm CmGmGmUmGmC#mU#mU#mU (tracrRNA 18) (SEQ ID NO: 28);

mA#mG#mC#mAmUmAmGmCmAmAmGrUrUmAr AmAmArUm AmAmGmGrCrUmArGrUrCmCrGfU-rUmAmUmCmAmAmCmUmUmGmAmAmA mAmAmGmUmGmGmCmAmCmCmGmAmGmUm CmGmGmUmGmC#mU#mU#mU (tracrRNA 19) (SEQ ID NO: 29); and mA#mG#mC#mAmUmAmGmCmAmAmGrUrUmAr AmAmArUm AmAmGmGrCrUmArGrUrCmCrGrU-fUmAmUmCmAmAmCmUmUmGmAmAmA mAmAmGmUmGmGmCmAmCmCmGmAmGmUm CmGmGmUmGmC#mU#mU#mU (tracrRNA 20) (SEQ ID NO: 30), wherein rN=RNA, mN=2'-O-methyl RNA, fN=2'-fluoro RNA, N#N=phosphorothioate linkage, and N=any nucleotide.

In an embodiment, the chemically modified guide RNA further comprises at least one moiety conjugated to the guide RNA.

In an embodiment, the at least one moiety is conjugated to at least one of the 5' end of the crRNA portion, the 3' end of the crRNA portion, the 5' end of the tracrRNA portion, and the 3' end of the tracrRNA portion.

In an embodiment, the at least one moiety increases cellular uptake of the guide RNA.

In an embodiment, the at least one moiety promotes specific tissue distribution of the guide RNA.

In an embodiment, the at least one moiety is selected from the group consisting of fatty acids, steroids, secosteroids, lipids, gangliosides analogs, nucleoside analogs, endocannabinoids, vitamins, receptor ligands, peptides, aptamers, and alkyl chains.

In an embodiment, the at least one moiety is selected from the group consisting of cholesterol, docosahexaenoic acid (DHA), docosanoic acid (DCA), lithocholic acid (LA), GalNAc, amphiphilic block copolymer (ABC), hydrophilic block copolymer (HBC), poloxamer, Cy5, and Cy3.

In an embodiment, the at least one moiety is conjugated to the guide RNA via a linker.

In an embodiment, the linker is selected from the group consisting of an ethylene glycol chain, an alkyl chain, a polypeptide, a polysaccharide, and a block copolymer.

In an embodiment, the at least one moiety is a modified lipid.

In an embodiment, the modified lipid is a branched lipid. In an embodiment, the modified lipid is a branched lipid of Formula I, Formula I: X-MC(═Y)M-Z-[L-MC(═Y)M-R]n, where X is a moiety that links the lipid to the guide RNA, each Y is independently oxygen or sulfur, each M is independently $CH_2$, NH, O or S, Z is a branching group which allows two or three ("n") chains to be joined to a chemically modified guide RNA, L is an optional linker moiety, and each R is independently a saturated, monounsaturated or polyunsaturated linear or branched moiety from 2 to 30 atoms in length, a sterol, or other hydrophobic group.

In an embodiment, the modified lipid is a headgroup-modified lipid. In an embodiment, the modified lipid is a headgroup-modified lipid of Formula II, Formula II: X-MC(═Y)M-Z-[L-MC(═Y)M-R]n-L-K-J, where X is a moiety that links the lipid to the guide RNA, each Y is independently oxygen or sulfur, each M is independently $CH_2$, NH, N-alkyl, O or S, Z is a branching group which allows two or three ("n") chains to be joined to chemically modified guide RNA, each L is independently an optional linker moiety, and R is a saturated, monounsaturated or polyunsaturated linear or branched moiety from 2 to 30 atoms in length, a sterol, or other hydrophobic group, K is a phosphate, sulfate, or amide and J is an aminoalkane or quaternary aminoalkane group.

In an embodiment, the guide RNA binds to a Cas9 nuclease selected from the group consisting of *S. pyogenes* Cas9 (SpCas9), *S. aureus* Cas9 (SaCas9), *N. meningitidis* Cas9 (NmCas9), *C. jejuni* Cas9 (CjCas9), and *Geobacillus* Cas9 (GeoCas9).

In an embodiment, the Cas9 is a variant Cas9 with altered activity.

In an embodiment, the variant Cas9 is selected from the group consisting of a Cas9 nickase (nCas9), a catalytically dead Cas9 (dCas9), a hyper accurate Cas9 (HypaCas9), a high fidelity Cas9 (Cas9-HF), an enhanced specificity Cas9 (eCas9), and an expanded PAM Cas9 (xCas9).

In an embodiment, the Cas9 off-target activity is reduced relative to an unmodified guide RNA.

In an embodiment, the Cas9 on-target activity is increased relative to an unmodified guide RNA.

In an embodiment, the chemically modified guide RNA further comprises a nucleotide or non-nucleotide loop or linker linking the 3' end of the crRNA portion to the 5' end of the tracrRNA portion.

In an embodiment, the non-nucleotide linker comprises an ethylene glycol oligomer linker.

In an embodiment, the nucleotide loop is chemically modified.

In certain aspects, the disclosure provides a modified guide RNA comprising: (a) a crRNA portion comprising (i) a guide sequence capable of hybridizing to a target polynucleotide sequence, and (ii) a repeat sequence; and (b) a tracrRNA portion comprising an anti-repeat nucleotide sequence that is complementary to the repeat sequence, wherein the repeat sequence of the crRNA portion and the anti-repeat sequence on the tracrRNA are modified to increase binding affinity between the repeat sequence and the anti-repeat sequence relative to an unmodified guide RNA.

In an embodiment, the modified guide RNA comprises an increased GC nucleotide content in the repeat and anti-repeat region relative to an unmodified guide RNA.

In an embodiment, the modified guide RNA comprises ribose modifications in the repeat and anti-repeat region.

In an embodiment, the repeat and anti-repeat modifications enhance the stability of pairing between the crRNA portion and the tracrRNA portion.

In an embodiment, the crRNA portion comprises the guide RNA modification pattern of NNNNNNNNNNNNNNNNNNNNGUUUUA-GAGCGAGCGC (SEQ ID NO: 31) and the tracrRNA portion comprises the guide RNA modification pattern of GCGCUCGCAAGUUAAAAUAAGGCUAGU-CCGUUAUCAACUUGAAAAAGU GGCACCGAGUCG-GUGCUUU (SEQ ID NO: 32), wherein N=any nucleotide.

In an embodiment, the one or more nucleotides are chemically modified.

In an embodiment, each one or more chemically modified nucleotides independently comprise a modification of a ribose group, a modification of a phosphate group, a modification of a nucleobase, or a combination thereof.

In an embodiment, each modification of the ribose group is independently selected from the group consisting of 2'-O-methyl, 2'-fluoro, 2'-deoxy, 2'-O-(2-methoxyethyl) (MOE), 2'-$NH_2$, or a bicyclic nucleotide such as locked nucleic acid (LNA), 2'-(S)-constrained ethyl (S-cEt), constrained MOE, or 2'-0,4'-C-aminomethylene bridged nucleic acid (2',4'-$BNA^{NC}$).

In an embodiment, each modification of the phosphate group is independently selected from the group consisting of a phosphorothioate, phosphonoacetate (PACE), thiophosphonoacetate (thioPACE), amide, triazole, phosphonate, or phosphotriester modification.

In an embodiment, each modification of the nucleobase group is independently selected from the group consisting of 2-thiouridine, 4-thiouridine, $N^6$-methyladenosine, pseudouridine, 2,6-diaminopurine, inosine, thymidine, 5-methylcytosine, 5-substituted pyrimidine, isoguanine, isocytosine, or halogenated aromatic groups.

In an embodiment, the modified guide RNA comprises a combination of increased GC nucleotide content in the repeat and anti-repeat region relative to an unmodified guide RNA and one or more chemically modified nucleotides.

In an embodiment, the modified guide RNA comprises a modification pattern selected from the group consisting of:

mN#mN#mN#mNmNmNmNmNmNmNfNfNfNfNrN# rN#fNfNrN#mNmGrU#rU#rU#fUfAmGmAmGm CmGmAmG#mC#mG#mC (hiGC crRNA 1) (SEQ ID NO: 33);

mN#mN#mN#mNmNmNmNmNmNmNfNfNfNfNrN# rN#fNfNrN#mNmGrU#rU#rU#fUfAmGmAfGfCfGf AfG#fC#mG#mC (hiGC crRNA 2) (SEQ ID NO: 34);

mN#mN#mN#mNmNmNmNmNmNmNfNfNfNfNrN# rN#fNfNrN#mNmGrU#rU#rU#fUfAmGmAfGmCf GmAfG#mC#mG#mC (hiGC crRNA 3) (SEQ ID NO: 35);

mN#mN#mN#mNmNmNmNmNmNmNfNfNfNfNrN# rN#fNfNrN#mNfGrU#rU#rU#fUfAmGmAfGmCfG mAfG#mC#mG#mC (hiGC crRNA 4) (SEQ ID NO: 36);

mG#mC#mG#mCmUmCmGmCmAmAmGrUrUmAr AmAmArUmA mAmGmGrCrUmArGrUrCmCrGrU-rUmAmUmCmAmAmCmUmUmGmAmAmAm AmAmGmUmGmGmCmAmCmCmGmAmGmUm CmGmGmUmGmC#mU#mU#m U (hiGC tracrRNA 1) (SEQ ID NO: 37);

mG#mC#fG#fCfUfCfGfCmAmAmGrUrUmArAmAm ArUmAmAm GmGrCrUmArGrUrCmCrGrUrUmA-mUmCmAmAmCmUmUmGmAmAmAmAmA mGmUmGmGmCmAmCmCmGmAmGmUmCmGm GmUmGmC#mU#mU#mU (hiGC tracrRNA 2) (SEQ ID NO: 38);

mG#mC#fG#mCfUmCfGmCmAmAmGrUrUmArAm AmArUmAm AmGmGrCrUmArGrUrCmCrGrUrU-mAmUmCmAmAmCmUmUmGmAmAmAmA mAmGmUmGmGmCmAmCmCmGmAmGmUmCm GmGmUmGmC#mU#mU#mU (hiGC tracrRNA 3) (SEQ ID NO: 39); and mG#mC#fG#mCfUmCfGmCmAmAmGrUrUfArAfAfA rUmAmAm GmGrCrUmArGrUrCmCrGrUrUmA-mUmCmAmAmCmUmUmGmAmAmAmAmA mGmUmGmGmCmAmCmCmGmAmGmUmCmGm GmUmGmC#mU#mU#mU (hiGC tracrRNA 4) (SEQ ID NO: 40), wherein rN=RNA, mN=2'-O-methyl RNA, fN=2'-fluoro RNA, N#N=phosphorothioate linkage, and N=any nucleotide.

In certain aspects, the disclosure provides a method of altering expression of a target gene in a cell, comprising administering to said cell a genome editing system comprising: a chemically modified guide RNA comprising: (a) a crRNA portion comprising (i) a guide sequence capable of hybridizing to a target polynucleotide sequence, and (ii) a repeat sequence; and (b) a tracrRNA portion an anti-repeat nucleotide sequence that is complementary to the repeat sequence; and an RNA-guided nuclease or a polynucleotide encoding an RNA-guided nuclease, wherein the chemically modified guide RNA comprises at least 80% modified nucleotides.

In an embodiment, the expression of the target gene is knocked out or knocked down.

In an embodiment, the sequence of the target gene is modified, edited, corrected or enhanced.

In an embodiment, the guide RNA and the RNA-guided nuclease comprise a ribonucleoprotein (RNP) complex.

In an embodiment, the RNA-guided nuclease is selected from the group consisting of *S. pyogenes* Cas9 (SpCas9), *S. aureus* Cas9 (SaCas9), *N. meningitidis* Cas9 (NmCas9), *C. jejuni* Cas9 (CjCas9), and *Geobacillus* Cas9 (GeoCas9).

In an embodiment, the Cas9 is a variant Cas9 with altered activity.

In an embodiment, the variant Cas9 is selected from the group consisting of a Cas9 nickase (nCas9), a catalytically dead Cas9 (dCas9), a hyper accurate Cas9 (HypaCas9), a high fidelity Cas9 (Cas9-HF), an enhanced specificity Cas9 (eCas9), and an expanded PAM Cas9 (xCas9).

In an embodiment, the polynucleotide encoding an RNA-guided nuclease comprises a vector.

In an embodiment, the vector is a viral vector.

In an embodiment, the viral vector is an adeno-associated virus (AAV) vector or a lentivirus (LV) vector.

In an embodiment, the polynucleotide encoding an RNA-guided nuclease comprises a synthetic mRNA.

In certain aspects, the disclosure provides a CRISPR genome editing system comprising, a chemically modified guide RNA comprising: (a) a crRNA portion comprising (i) a guide sequence capable of hybridizing to a target polynucleotide sequence, and (ii) a repeat sequence; and (b) a tracrRNA portion comprising an anti-repeat nucleotide sequence that is complementary to the repeat sequence; and an RNA-guided nuclease or a polynucleotide encoding an RNA-guided nuclease, wherein the chemically modified guide RNA comprises at least 80% modified nucleotides.

In an embodiment, the one or more modified nucleotides comprise a modification in a ribose group, a phosphate group, a nucleobase, or a combination thereof.

In an embodiment, at least 80% of the ribose groups are chemically modified.

In an embodiment, each modification of the ribose group is independently selected from the group consisting of 2'-O-methyl, 2'-fluoro, 2'-deoxy, 2'-O-(2-methoxyethyl) (MOE), 2'-$NH_2$, a bicyclic nucleotide, a locked nucleic acid (LNA), a 2'-(S)-constrained ethyl (S-cEt), a constrained MOE, or a 2'-0,4'-C-aminomethylene bridged nucleic acid (2',4'-$BNA^{NC}$).

In an embodiment, each modification of the phosphate group is independently selected from the group consisting of a phosphorothioate, phosphonoacetate (PACE), thiophosphonoacetate (thioPACE), amide, triazole, phosphonate, or phosphotriester modification.

In an embodiment, each modification of the nucleobase group is independently selected from the group consisting of 2-thiouridine, 4-thiouridine, $N^6$-methyladenosine, pseudouridine, 2,6-diaminopurine, inosine, thymidine, 5-methylcytosine, 5-substituted pyrimidine, isoguanine, isocytosine, or halogenated aromatic groups.

In an embodiment, the guide RNA comprises at least 90% modified nucleotides.

In an embodiment, the guide RNA comprises 100% modified nucleotides.

In an embodiment, the RNA-guided nuclease is selected from the group consisting of *S. pyogenes* Cas9 (SpCas9), *S. aureus* Cas9 (SaCas9), *N. meningitidis* Cas9 (NmCas9), *C. jejuni* Cas9 (CjCas9), and *Geobacillus* Cas9 (GeoCas9).

In an embodiment, the Cas9 is a variant Cas9 with altered activity.

In an embodiment, the variant Cas9 is selected from the group consisting of a Cas9 nickase (nCas9), a catalytically dead Cas9 (dCas9), a hyper accurate Cas9 (HypaCas9), a high fidelity Cas9 (Cas9-HF), an enhanced specificity Cas9 (eCas9), and an expanded PAM Cas9 (xCas9).

In an embodiment, the Cas9 off-target activity is reduced relative to an unmodified guide RNA.

In an embodiment, the Cas9 on-target activity is increased relative to an unmodified guide RNA.

In certain aspects, the disclosure provides a chemically modified guide RNA comprising: (a) a crRNA portion comprising (i) a guide sequence capable of hybridizing to a target polynucleotide sequence, and (ii) a repeat sequence; and (b) a tracrRNA portion comprising an anti-repeat nucleotide sequence that is complementary to the repeat sequence, wherein the chemically modified guide RNA comprises at least 100% modified nucleotides.

In an embodiment, all ribose groups are chemically modified.

BRIEF DESCRIPTION OF THE DRAWINGS

The foregoing and other features and advantages of the present disclosure will be more fully understood from the following detailed description of illustrative embodiments taken in conjunction with the accompanying drawings.

FIG. 1A is a crRNA and tracrRNA when paired with the target genomic DNA. FIG. 1A discloses SEQ ID NOS 128-129, respectively, in order of appearance. FIG. 1B depicts an exemplary heavily modified crRNA (C20 (SEQ ID NO: 55)) and tracrRNA (T2 (SEQ ID NO: 13)). FIG. 1C depicts an exemplary fully modified crRNA (C21 (SEQ ID NO: 56)) and tracrRNA (T8 (SEQ ID NO: 18)).

FIG. 9 discloses SEQ ID NOS 60 and 37, respectively, in order of appearance.

FIG. 14A discloses SEQ ID NOS 56 and 56, FIG. 14B discloses SEQ ID NOS 18 and 18, FIG. 14C discloses SEQ ID NOS 56 and 18 and FIG. 14D discloses SEQ ID NOS 130 and 131, all respectively, in order of appearance.

FIG. 15 discloses SEQ ID NOS 132-137, respectively, in order of appearance.

DETAILED DESCRIPTION

Figure 1A:
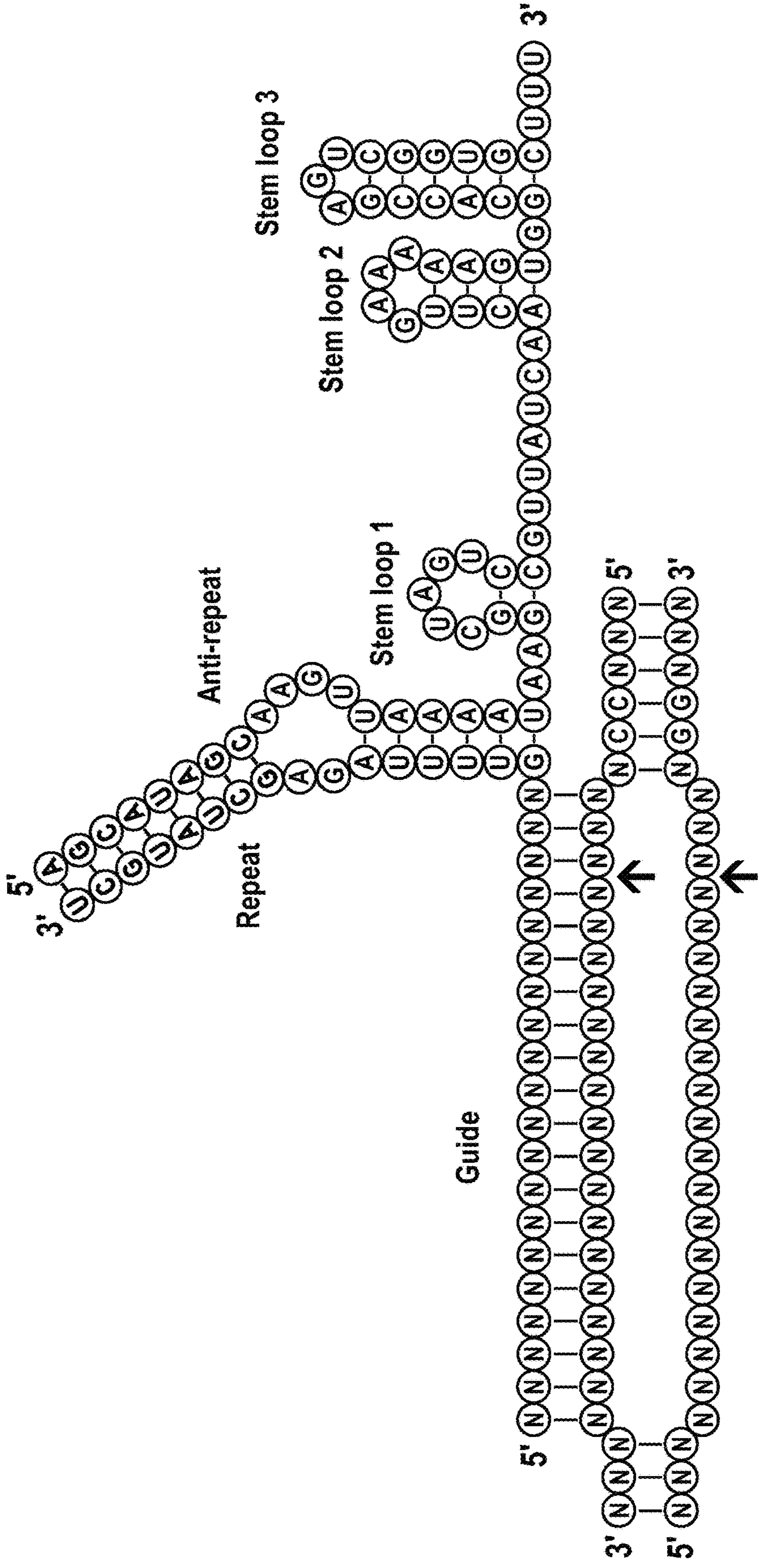
FIG. 1A-FIG. 1C depict schematics of crRNA and tracrRNA.

Provided herewith are novel chemically modified crRNAs and tracrRNAs, including heavily or fully chemically modified crRNAs and tracrRNAs. In certain embodiments, crRNAs and tracrRNAs with 5' and/or 3' conjugated moieties are provided. In yet other embodiments, crRNAs and tracrRNAs with modifications in the repeat region of the crRNA or the anti-repeat region of the tracrRNA are provided. Methods of using the crRNAs and tracrRNAs of the disclosure for genome editing with a CRISPR nuclease and kits for performing the same are also provided.

Unless otherwise defined herein, nomenclature used in connection with cell and tissue culture, molecular biology, immunology, microbiology, genetics and protein and nucleic acid chemistry and hybridization described herein are those well-known and commonly used in the art. The methods and techniques provided herein are usually performed according to conventional methods well known in the art and as described in various general and more specific references that are cited and discussed throughout the present specification unless otherwise indicated. Enzymatic reactions and purification techniques are performed according to manufacturer's specifications unless otherwise specified, as commonly accomplished in the art or as described herein. The nomenclature used in connection with, and the laboratory procedures and techniques of, analytical chemistry, synthetic organic chemistry, and medicinal and pharmaceutical chemistry described herein are those well-known and commonly used in the art, unless otherwise specified. Standard techniques are used for chemical syntheses, chemical analyses, pharmaceutical preparation, formulation, and delivery, and treatment of patients.

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

So that the disclosure may be more readily understood, certain terms are first defined.

As used herein, the term "guide RNA" or "gRNA" refer to any nucleic acid that promotes the specific association (or "targeting") of an RNA-guided nuclease such as a Cas9 to a target sequence (e.g., a genomic or episomal sequence) in a cell.

As used herein, a "modular" or "dual RNA" guide comprises more than one, and typically two, separate RNA molecules, such as a CRISPR RNA (crRNA) and a trans-activating crRNA (tracrRNA), which are usually associated with one another, for example by duplexing. gRNAs and their component parts are described throughout the literature (see, e.g., Briner et al. Mol. Cell, 56 (2), 333-339 (2014), which is incorporated by reference).

As used herein, a "unimolecular gRNA," "chimeric gRNA," or "single guide RNA (sgRNA)" comprises a single RNA molecule. The sgRNA may be a crRNA and tracrRNA linked together. For example, the 3' end of the crRNA may be linked to the 5' end of the tracrRNA. A crRNA and a tracrRNA may be joined into a single unimolecular or chimeric gRNA, for example, by means of a four nucleotide (e.g., GAAA) "tetraloop" or "linker" sequence bridging complementary regions of the crRNA (at its 3' end) and the tracrRNA (at its 5' end).

As used herein, a "repeat" sequence or region is a nucleotide sequence at or near the 3' end of the crRNA which is complementary to an anti-repeat sequence of a tracrRNA.

As used herein, an "anti-repeat" sequence or region is a nucleotide sequence at or near the 5' end of the tracrRNA which is complementary to the repeat sequence of a crRNA.

Additional details regarding guide RNA structure and function, including the gRNA/Cas9 complex for genome editing may be found in, at least, Mali et al. Science, 339 (6121), 823-826 (2013); Jiang et al. Nat. Biotechnol. 31 (3). 233-239 (2013); and Jinek et al. Science, 337 (6096), 816-821 (2012); which are incorporated by reference herein.

As used herein, a "guide sequence" or "targeting sequence" refers to the nucleotide sequence of a gRNA, whether unimolecular or modular, that is fully or partially complementary to a target domain or target polynucleotide within a DNA sequence in the genome of a cell where editing is desired. Guide sequences are typically 10-30 nucleotides in length, preferably 16-24 nucleotides in length (for example, 16, 17, 18, 19, 20, 21, 22, 23 or 24 nucleotides in length), and are at or near the 5' terminus of a Cas9 gRNA.

As used herein, a "target domain" or target polynucleotide sequence" is the DNA sequence in a genome of a cell that is complementary to the guide sequence of the gRNA.

In addition to the targeting domains, gRNAs typically include a plurality of domains that influence the formation or activity of gRNA/Cas9 complexes. For example, as mentioned above, the duplexed structure formed by first and secondary complementarity domains of a gRNA (also referred to as a repeat: anti-repeat duplex) interacts with the recognition (REC) lobe of Cas9 and may mediate the formation of Cas9/gRNA complexes (Nishimasu et al. Cell 156:935-949 (2014); Nishimasu et al. Cell 162 (2), 1113-1126 (2015), both incorporated by reference herein). It should be noted that the first and/or second complementarity domains can contain one or more poly-A tracts, which can be recognized by RNA polymerases as a termination signal. The sequence of the first and second complementarity domains are, therefore, optionally modified to eliminate these tracts and promote the complete in vitro transcription of gRNAs, for example through the use of A-G swaps as described in Briner 2014, or A-U swaps. These and other similar modifications to the first and second complementarity domains are within the scope of the present disclosure.

Along with the first and second complementarity domains, Cas9 gRNAs typically include two or more additional duplexed regions that are necessary for nuclease activity in vivo but not necessarily in vitro (Nishimasu 2015, supra). A first stem-loop near the 3' portion of the second complementarity domain is referred to variously as the "proximal domain," "stem loop 1" (Nishimasu 2014, supra; Nishimasu 2015, supra) and the "*nexus*" (Briner 2014, supra). One or more additional stem loop structures are generally present near the 3' end of the gRNA, with the number varying by species: *S. pyogenes* gRNAs typically include two 3' stem loops (for a total of four stem loop structures including the repeat: anti-repeat duplex), while s. *aureus* and other species have only one (for a total of three). A description of conserved stem loop structures (and gRNA structures more generally) organized by species is provided in Briner 2014, which is incorporated herein by reference. Additional details regarding guide RNAs generally may be found in WO2018026976A1, which is incorporated herein by reference.

Figure 1B:
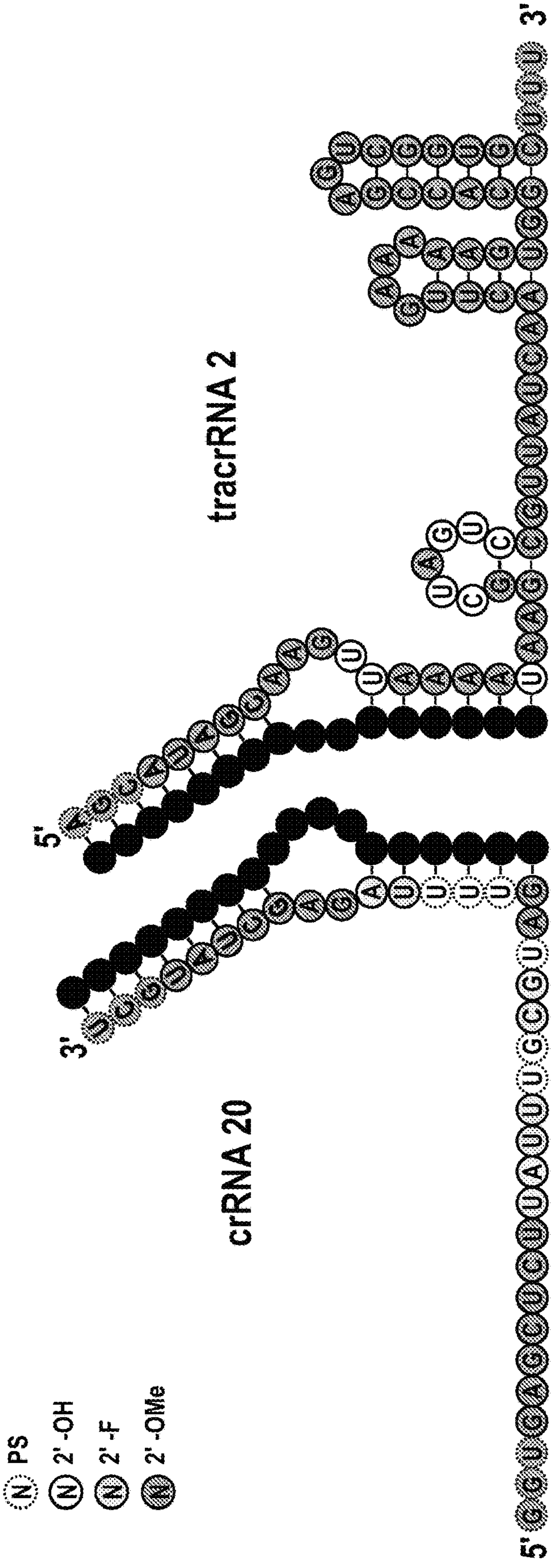
Figure 1C:
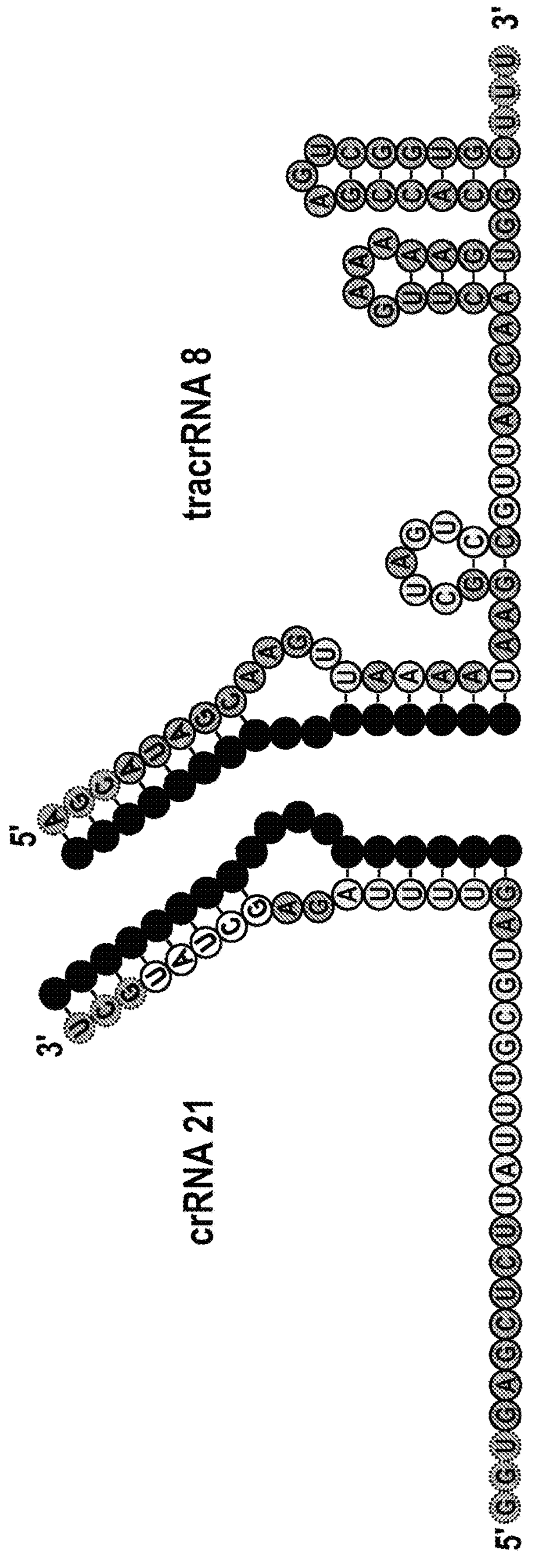

A representative guide RNA is shown in FIG. 1.

Chemically Modified Guide RNA

The chemically modified guide RNAs of the disclosure possess improved in vivo stability, improved genome editing efficacy, and/or reduced immunotoxicity relative to unmodified or minimally modified guide RNAs.

Chemically modified guide RNAs of the disclosure contain one or more modified nucleotides comprising a modification in a ribose group, a phosphate group, a nucleobase, or a combination thereof.

Chemical modifications to the ribose group may include, but are not limited to, 2'-O-methyl, 2'-fluoro, 2'-deoxy, 2'-O-(2-methoxyethyl) (MOE), 2'-NH2, 2'-O-Allyl, 2'-O-Ethylamine, 2'-O-Cyanoethyl, 2'-O-Acetalester, or a bicyclic nucleotide such as locked nucleic acid (LNA), 2'-(S)-constrained ethyl (S-cEt), constrained MOE, or 2'-0,4'-C-aminomethylene bridged nucleic acid (2',4'-$BNA^{NC}$).

Chemical modifications to the phosphate group may include, but are not limited to, a phosphorothioate, phosphonoacetate (PACE), thiophosphonoacetate (thioPACE), amide, triazole, phosphonate, or phosphotriester modification.

Chemical modifications to the nucleobase may include, but are not limited to, 2-thiouridine, 4-thiouridine, $N^6$-methyladenosine, pseudouridine, 2,6-diaminopurine, inosine, thymidine, 5-methylcytosine, 5-substituted pyrimidine, isoguanine, isocytosine, or halogenated aromatic groups.

The chemically modified guide RNAs may have one or more chemical modifications in the crRNA portion and/or the tracrRNA portion for a modular or dual RNA guide. The chemically modified guide RNAs may also have one or more chemical modifications in the single guide RNA for the unimolecular guide RNA.

The chemically modified guide RNAs may comprise at least about 50% to at least about 100% chemically modified nucleotides, at least about 60% to at least about 100% chemically modified nucleotides, at least about 70% to at least about 100% chemically modified nucleotides, at least about 80% to at least about 100% chemically modified nucleotides, at least about 90% to at least about 100% chemically modified nucleotides, and at least about 95% to at least about 100% chemically modified nucleotides.

The chemically modified guide RNAs may comprise at least about 50% chemically modified nucleotides, at least about 60% chemically modified nucleotides, at least about 70% chemically modified nucleotides, at least about 80% chemically modified nucleotides, at least about 90% chemically modified nucleotides, at least about 95% chemically modified nucleotides, at least about 99% chemically modified, or 100% (fully) chemically modified nucleotides.

The chemically modified guide RNAs may comprise at least about 80%, 81%, 82%, 83%, 84%, 85%, 86%, 87%, 88%, 89%, 90%, 91%, 92%, 93%, 94%, 95%, 96%, 97%, 98%, 99%, or 100% chemically modified nucleotides.

Guide RNAs that comprise at least about 80% chemically modified nucleotides to at least about 99% chemically modified nucleotides are considered "heavily" modified, as used herein.

Guide RNAs that comprise 100% chemically modified nucleotides are considered "fully" modified, as used herein.

In certain exemplary embodiments, the chemically modified guide RNAs may comprise a chemically modified ribose group at about 50% of the guide RNA nucleotides to about 100% of the guide RNA nucleotides, at about 60% of the guide RNA nucleotides to about 100% of the guide RNA nucleotides, at about 70% of the guide RNA nucleotides to about 100% of the guide RNA nucleotides, at about 80% of the guide RNA nucleotides to about 100% of the guide RNA nucleotides, at about 90% of the guide RNA nucleotides to about 100% of the guide RNA nucleotides, and at about 95% of the guide RNA nucleotides to about 100% of the guide RNA nucleotides In certain exemplary embodiments, the chemically modified guide RNAs may comprise a chemically modified ribose group at about 50% of the guide RNA nucleotides, at about 60% of the guide RNA nucleotides, at about 70% of the guide RNA nucleotides, at about 80% of the guide RNA nucleotides, at about 90% of the guide RNA nucleotides, at about 95% of the guide RNA nucleotides, at about 99% of the guide RNA nucleotides, or at 100% of the guide RNA nucleotides.

In certain exemplary embodiments, the chemically modified guide RNAs may comprise a chemically modified ribose group at about 80%, 81%, 82%, 83%, 84%, 85%, 86%, 87%, 88%, 89%, 90%, 91%, 92%, 93%, 94%, 95%, 96%, 97%, 98%, 99%, or 100% of the guide RNA nucleotides.

Guide RNAs that have at least about 80% of the ribose groups chemically modified to at least about 99% of the ribose groups chemically modified are considered "heavily" modified, as used herein.

Guide RNAs that have 100% of the ribose groups chemically modified are considered "fully" modified, as used herein.

In certain exemplary embodiments, the chemically modified guide RNAs may comprise a chemically modified phosphate group at about 50% of the guide RNA nucleotides to about 100% of the guide RNA nucleotides, at about 60% of the guide RNA nucleotides to about 100% of the guide RNA nucleotides, at about 70% of the guide RNA nucleotides to about 100% of the guide RNA nucleotides, at about 80% of the guide RNA nucleotides to about 100% of the guide RNA nucleotides, at about 90% of the guide RNA nucleotides to about 100% of the guide RNA nucleotides, and at about 95% of the guide RNA nucleotides to about 100% of the guide RNA nucleotides In certain exemplary embodiments, the chemically modified guide RNAs may comprise a chemically modified phosphate group at about 50% of the guide RNA nucleotides, at about 60% of the guide RNA nucleotides, at about 70% of the guide RNA nucleotides, at about 80% of the guide RNA nucleotides, at about 90% of the guide RNA nucleotides, at about 95% of the guide RNA nucleotides, at about 99% of the guide RNA nucleotides, or at 100% of the guide RNA nucleotides.

In certain exemplary embodiments, the chemically modified guide RNAs may comprise a chemically modified phosphate group at about 80%, 81%, 82%, 83%, 84%, 85%, 86%, 87%, 88%, 89%, 90%, 91%, 92%, 93%, 94%, 95%, 96%, 97%, 98%, 99%, or 100% of the guide RNA nucleotides.

Guide RNAs that have at least about 80% of the phosphate groups chemically modified to at least about 99% of the phosphate groups chemically modified are considered "heavily" modified, as used herein.

Guide RNAs that have 100% of the phosphate groups chemically modified are considered "fully" modified, as used herein.

In certain exemplary embodiments, the chemically modified guide RNAs may comprise a chemically modified nucleobase at about 50% of the guide RNA nucleotides to about 100% of the guide RNA nucleotides, at about 60% of the guide RNA nucleotides to about 100% of the guide RNA nucleotides, at about 70% of the guide RNA nucleotides to about 100% of the guide RNA nucleotides, at about 80% of the guide RNA nucleotides to about 100% of the guide RNA nucleotides, at about 90% of the guide RNA nucleotides to about 100% of the guide RNA nucleotides, and at about 95% of the guide RNA nucleotides to about 100% of the guide RNA nucleotides.

In certain exemplary embodiments, the chemically modified guide RNAs may comprise a chemically modified nucleobase at about 50% of the guide RNA nucleotides, at about 60% of the guide RNA nucleotides, at about 70% of the guide RNA nucleotides, at about 80% of the guide RNA nucleotides, at about 90% of the guide RNA nucleotides, at about 95% of the guide RNA nucleotides, at about 99% of the guide RNA nucleotides, or at 100% of the guide RNA nucleotides.

In certain exemplary embodiments, the chemically modified guide RNAs may comprise a chemically modified nucleobase at about 80%, 81%, 82%, 83%, 84%, 85%, 86%, 87%, 88%, 89%, 90%, 91%, 92%, 93%, 94%, 95%, 96%, 97%, 98%, 99%, or 100% of the guide RNA nucleotides.

Guide RNAs that have at least about 80% of the nucleobases chemically modified to at least about 99% of the nucleobases chemically modified are considered "heavily" modified, as used herein.

Guide RNAs that have 100% of the nucleobases chemically modified are considered "fully" modified, as used herein.

In certain exemplary embodiments, the chemically modified guide RNAs may comprise any combination of chemically modified ribose groups, chemically modified phosphate groups, and chemically modified nucleobases at about 50% of the guide RNA nucleotides to about 100% of the guide RNA nucleotides, at about 60% of the guide RNA nucleotides to about 100% of the guide RNA nucleotides, at about 70% of the guide RNA nucleotides to about 100% of the guide RNA nucleotides, at about 80% of the guide RNA nucleotides to about 100% of the guide RNA nucleotides, at about 90% of the guide RNA nucleotides to about 100% of the guide RNA nucleotides, and at about 95% of the guide RNA nucleotides to about 100% of the guide RNA nucleotides.

In certain exemplary embodiments, the chemically modified guide RNAs may comprise any combination of chemically modified ribose groups, chemically modified phosphate groups, and chemically modified nucleobases at about 50% of the guide RNA nucleotides, at about 60% of the guide RNA nucleotides, at about 70% of the guide RNA nucleotides, at about 80% of the guide RNA nucleotides, at about 90% of the guide RNA nucleotides, at about 95% of the guide RNA nucleotides, at about 99% of the guide RNA nucleotides, or at 100% of the guide RNA nucleotides.

In certain exemplary embodiments, the chemically modified guide RNAs may comprise any combination of chemically modified ribose groups, chemically modified phosphate groups, and chemically modified nucleobases at about 80%, 81%, 82%, 83%, 84%, 85%, 86%, 87%, 88%, 89%, 90%, 91%, 92%, 93%, 94%, 95%, 96%, 97%, 98%, 99%, or 100% of the guide RNA nucleotides.

Guide RNAs that have at least about 80% of any combination of the ribose groups, the phosphate groups, and the nucleobases chemically modified to at least about 99% of the nucleobases chemically modified are considered "heavily" modified, as used herein.

Guide RNAs that have 100% of any combination of the ribose groups, the phosphate groups, and the nucleobases chemically modified are considered "fully" modified, as used herein.

The heavily and fully chemically modified guide RNAs of the disclosure possess several advantages over the minimally modified guide RNAs in the art. Heavily and fully chemically modified guide RNAs are expected to ease chemical synthesis, further enhance in vivo stability, and provide a scaffold for terminally appended chemical functionalities that facilitate delivery and efficacy during clinical applications to genome editing.

The chemical modification pattern used in the guide RNA is preferably such that activity of the guide RNA is maintained when paired with an RNA-guided DNA endonuclease, e.g., Cas9. Exemplary chemical modification patterns are described in Table 1 below.

TABLE 1

Exemplary chemical modification patterns for crRNAs and tracrRNAs

| Name | SEQ ID NO: | Sequence |
|---|---|---|
| crRNA 1 | 41 | mG#mG#mU#mGmAmGmCmUmCmUrUrArUrUrUmGmCmGrUmAmGrUrUrUmUmAmGmAmGmCmUmAmU#mG#mCmU |
| crRNA 2 | 42 | rGrGrUrGrArGmCmUmCmUrUrArUrUrUrGrCrGrUmAmGrUrUrUrUrAmGmAmGmCmUmAmU#mG#mCmU |
| crRNA 3 | 43 | rG#rG#rU#rGrArGmCmUmCmUrUrArUrUrUrGrCrGrUmAmGrUrUrUrUrAmGmAmGmCmUmAmU#mG#mCmU |
| crRNA 4 | 44 | mG#mG#mU#mGmAmGmCmUmCmUrUrArUrUrUrGrCrGrUmAmGrUrUrUrUrAmGmAmGmCmUmAmU#mG#mC#mU |
| crRNA 5 | 45 | rG#rG#rU#rGrArGmCmUmCmUrUrArUrUrUrGmCmGrUmAmGrUrUrUrUrAmGmAmGmCmUmAmU#mG#mC#mU |
| crRNA 6 | 46 | rG#rG#rU#rGrArGmCmUmCmUrUrArUrUrUrGrCrGrUmAmGrUrUrUmUmAmGmAmGmCmUmAmU#mG#mC#mU |
| crRNA 7 | 47 | mG#mG#mU#mGmAmGmCmUmCmUrUrArUrUrUrGmCmGrUmAmGrUrUrUrUrAmGmAmGmCmUmAmU#mG#mC#mU |
| crRNA 8 | 48 | mG#mG#mU#mGmAmGmCmUmCmUrUrArUrUrUrGrCrGrUmAmGrUrUrUmUmAmGmAmGmCmUmAmU#mG#mC#mU |
| crRNA 9 | 49 | mG#mG#mU#mGmAmGmCmUmCmUrUrArUrUrU#rG#rCrGrU#mAmGrU#rU#rU#mUmAmGmAmGmCmUmAmU#mG#mC#mU |
| crRNA 10 | 50 | mG#mG#mU#mGmAmGmCmUmCmUfUfAfUfUrU#rG#fCfGrU#mAmGrU#rU#rU#mUmAmGmAmGmCmUmAmU#mG#mC#mU |
| crRNA 11 | 51 | mG#mG#mU#mGmAmGmCmUmCmUfUfAfUfUrU#rG#rC#rG#rU#mAmGrU#rU#rU#mUmAmGmAmGmCmUmAmU#mG#mC#mU |
| crRNA 17 | 52 | mG#mG#mU#mGmAmGmCmUmCmUfUfAfUfUrU#rG#fCfGrU#mAmGrU#rU#rU#mUrA#mGmAmGmCmUmAmU#mG#mC#mU |
| crRNA 18 | 53 | mG#mG#mU#mGmAmGmCmUmCmUfUfAfUfUrU#rG#fCfGrU#mAmGrU#rU#rU#rU#mAmGmAmGmCmUmAmU#mG#mC#mU |
| crRNA 19 | 54 | mG#mG#mU#mGmAmGmCmUmCmUfUfAfUfUrU#rG#fCfGrU#nAmGrU#rU#rU#rU#rA#mGmAmGmCmUmAmU#mG#mC#mU |
| crRNA 20 | 55 | mG#mG#mU#mGmAmGmCmUmCmUfUfAfUfUrU#rG#fCfGrU#mAmGrU#rU#rU#fUfAmGmAmGmCmUmAmU#mG#mC#mU |
| crRNA 21 | 56 | mG#mG#mU#mGmAmGmCmUmCmUfUfAfUfUfUfGfCfGfUmAmGfUfUfUfUfAmGmAmGmCmUmAmU#mG#mC#mU |
| crRNA 22 | 57 | mG#mG#mU#mGmAmGmCmUmCmUfUfAfUfUrU#rG#fCfGrU#mAmGfUrU#fUfUfAmGmAmGmCmUmAmU#mG#mC#mU |
| tracrRNA 1 | 58 | mA#mG#mC#mAmUmAmGrCrArArGrUrUmArArArArUrArArGmGrCrUmArGrUrCmCrGrUrUrArUrCrAmAmCmUmUmGmAmAmAmAmAmGmUrGrGrCrAmCmCmGrArGrUrCrGmGmUmGmC#mU#mU#mU |
| tracrRNA 2 | 13 | mA#mG#mC#mAmUmAmGmCmAmAmGrUrUmArAmAmArUmAmAmGmGrCrUmArGrUrCmCrGrUrUmAmUmCmAmAmCmUmUmGmAmAmAmAmAmGmUmGmGmCmAmCmCmGmAmGmUmCmGmGmUmGmC#mU#mU#mU |
| tracrRNA 3 | 14 | mA#mG#mC#mAmUmAmGmCmAmAmGrU#rU#mArA#mAmArU#mAmAmGmGrC#rU#mArG#rU#rC#mCrG#rU#rU#mAmUmCmAmAmCmUmUmGmAmAmAmAmAmGmUmGmGmCmAmCmCmGmAmGmUmCmGmGmUmGmC#mU#mU#mU |
| tracrRNA 4 | 15 | mA#mG#mC#mAmUmAmGmCmAmAmGrUrUmAmAmAmArUmAmAmGmGrCrUmArGrUrCmCrGrUrUmAmUmCmAmAmCmUmUmGmAmAmAmAmAmGmUmGmGmCmAmCmCmGmAmGmUmCmGmGmUmGmC#mU#mU#mU |
| tracrRNA 5 | 59 | mA#mG#mC#mAmUmAmGmCmAmAmGrUrUmAmAmAmArUmAmAmGmGrCrUmArGrUrCmCrGrUrUmAmUmCmAmAmCmUmUmGmAmAmAmAmAmGmUmGmGmCmAmCmCmGmAmGmUmCmGmGmUmGmC#mU#mU#mU-TegChol |
| tracrRNA 6 | 16 | mA#mG#mC#mAmUmAmGmCmAmAmGrUrUmArAmAmAfUmAmAmGmGfCfUmArGfUfCmCrGrUrUmAmUmCmAmAmCmUmUmGmAmAmAmAmAmGmUmGmGmCmAmCmCmGmAmGmUmCmGmGmUmGmC#mU#mU#mU |
| tracrRNA 7 | 17 | mA#mG#mC#mAmUmAmGmCmAmAmGrUfUmArAmAmAfUmAmAmGmGfCfUmAfGfUfCmCrGrUrUmAmUmCmAmAmCmUmUmGmAmAmAmAmAmGmUmGmGmCmAmCmCmGmAmGmUmCmGmGmUmGmC#mU#mU#mU |

TABLE 1-continued

Exemplary chemical modification patterns for crRNAs and tracrRNAs

| Name | SEQ ID NO: | Sequence |
|---|---|---|
| tracrRNA 8 | 18 | mA#mG#mC#mAmUmAmGmCmAmAmGfUfUmAfAmAmA<br>fUmAmAmGmGfCfUmAfGfUfCmCfGfUfUmAmUmCmAmA<br>mCmUmUmGmAmAmAmAmAmGmUmGmGmCmAmCmC<br>mGmAmGmUmCmGmGmUmGmC#mU#mU#mU |
| tracrRNA 9 | 19 | mA#mG#mC#mAmUmAmGmCmAmAmGfUrUmArAmAmA<br>rUmAmAmGmGrCrUmArGrUrCmCrGrUrUmAmUmCmAmA<br>mCmUmUmGmAmAmAmAmAmGmUmGmGmCmAmCmC<br>mGmAmGmUmCmGmGmUmGmC#mU#mU#mU |
| tracrRNA 10 | 20 | mA#mG#mC#mAmUmAmGmCmAmAmGrUfUmArAmAmA<br>rUmAmAmGmGrCrUmArGrUrCmCrGrUrUmAmUmCmAmA<br>mCmUmUmGmAmAmAmAmAmGmUmGmGmCmAmCmC<br>mGmAmGmUmCmGmGmUmGmC#mU#mU#mU |
| tracrRNA 11 | 21 | mA#mG#mC#mAmUmAmGmCmAmAmGrUrUmAfAmAmA<br>rUmAmAmGmGrCrUmArGrUrCmCrGrUrUmAmUmCmAmA<br>mCmUmUmGmAmAmAmAmAmGmUmGmGmCmAmCmC<br>mGmAmGmUmCmGmGmUmGmC#mU#mU#mU |
| tracrRNA 12 | 22 | mA#mG#mC#mAmUmAmGmCmAmAmGrUrUmArAmAmA<br>fUmAmAmGmGrCrUmArGrUrCmCrGrUrUmAmUmCmAmA<br>mCmUmUmGmAmAmAmAmAmGmUmGmGmCmAmCmC<br>mGmAmGmUmCmGmGmUmGmC#mU#mU#mU |
| tracrRNA 13 | 23 | mA#mG#mC#mAmUmAmGmCmAmAmGrUrUmArAmAmA<br>rUmAmAmGmGfCrUmArGrUrCmCrGrUrUmAmUmCmAmA<br>mCmUmUmGmAmAmAmAmAmGmUmGmGmCmAmCmC<br>mGmAmGmUmCmGmGmUmGmC#mU#mU#mU |
| tracrRNA 14 | 24 | mA#mG#mC#mAmUmAmGmCmAmAmGrUrUmArAmAmA<br>rUmAmAmGmGrCfUmArGrUrCmCrGrUrUmAmUmCmAmA<br>mCmUmUmGmAmAmAmAmAmGmUmGmGmCmAmCmC<br>mGmAmGmUmCmGmGmUmGmC#mU#mU#mU |
| tracrRNA 15 | 25 | mA#mG#mC#mAmUmAmGmCmAmAmGrUrUmArAmAmA<br>rUmAmAmGmGrCrUmAfGrUrCmCrGrUrUmAmUmCmAmA<br>mCmUmUmGmAmAmAmAmAmGmUmGmGmCmAmCmC<br>mGmAmGmUmCmGmGmUmGmC#mU#mU#mU |
| tracrRNA 16 | 26 | mA#mG#mC#mAmUmAmGmCmAmAmGrUrUmArAmAmA<br>rUmAmAmGmGrCrUmArGfUrCmCrGrUrUmAmUmCmAmA<br>mCmUmUmGmAmAmAmAmAmGmUmGmGmCmAmCmC<br>mGmAmGmUmCmGmGmUmGmC#mU#mU#mU |
| tracrRNA 17 | 27 | mA#mG#mC#mAmUmAmGmCmAmAmGrUrUmArAmAmA<br>rUmAmAmGmGrCrUmArGrUfCmCrGrUrUmAmUmCmAmA<br>mCmUmUmGmAmAmAmAmAmGmUmGmGmCmAmCmC<br>mGmAmGmUmCmGmGmUmGmC#mU#mU#mU |
| tracrRNA 18 | 28 | mA#mG#mC#mAmUmAmGmCmAmAmGrUrUmArAmAmA<br>rUmAmAmGmGrCrUmArGrUrCmCfGrUrUmAmUmCmAmA<br>mCmUmUmGmAmAmAmAmAmGmUmGmGmCmAmCmC<br>mGmAmGmUmCmGmGmUmGmC#mU#mU#mU |
| tracrRNA 19 | 29 | mA#mG#mC#mAmUmAmGmCmAmAmGrUrUmArAmAmA<br>rUmAmAmGmGrCrUmArGrUrCmCrGfUrUmAmUmCmAmA<br>mCmUmUmGmAmAmAmAmAmGmUmGmGmCmAmCmC<br>mGmAmGmUmCmGmGmUmGmC#mU#mU#mU |
| tracrRNA 20 | 30 | mA#mG#mC#mAmUmAmGmCmAmAmGrUrUmArAmAmA<br>rUmAmAmGmGrCrUmArGrUrCmCrGrUfUmAmUmCmAmA<br>mCmUmUmGmAmAmAmAmAmGmUmGmGmCmAmCmC<br>mGmAmGmUmCmGmGmUmGmC#mU#mU#mU |

KEY: rN = RNA, mN = 2'-O-methyl RNA, fN = 2'-fluoro RNA N#N = phosphorothioate linkage It will be understood to those of skill in the art that the base sequence of the first 20 nucleotides of the exemplary crRNAs recited in Table 1 above are directed to a specific target. This 20 nucleotide base sequence may be changed based on the target nucleic acid, however the chemical modifications remain the same.

It will be further understood to those of skill in the art that the guide sequence may be 10-30 nucleotides in length, preferably 16-24 nucleotides in length (for example, 16, 17, 18, 19, 20, 21, 22, 23 or 24 nucleotides in length), and is at or near the 5' terminus of a Cas9 gRNA.

High-Affinity Repeat/Anti-Repeat Guide RNA Modifications

A crRNA and a tracrRNA hybridize together by forming a duplex between the repeat region of the crRNA and the anti-repeat region of the tracrRNA (see FIG. 1). In certain embodiments, modular, or dual RNA, guide RNAs are provided with modifications in the repeat region and the anti-repeat region to enhance the affinity between the two regions and form a stronger duplex.

The high-affinity interaction may be enhanced by increasing the GC nucleotide content in the duplex formed by the repeat regions and the anti-repeat region. Nucleotide modifications, such as 2'-Fluoro and 2'-O-Methyl modifications, may also be introduced, which increase the melting temperature (Tm) of the duplex. Further modifications include the use of orthogonal and non-naturally occurring nucleotides. The various repeat region/anti-repeat region modifications described herein enhance the stability of the duplex, helping to prevent the crRNA and tracrRNA from folding into sub-optimal structures and therefore promoting higher genome editing efficacy.

Figure 9:
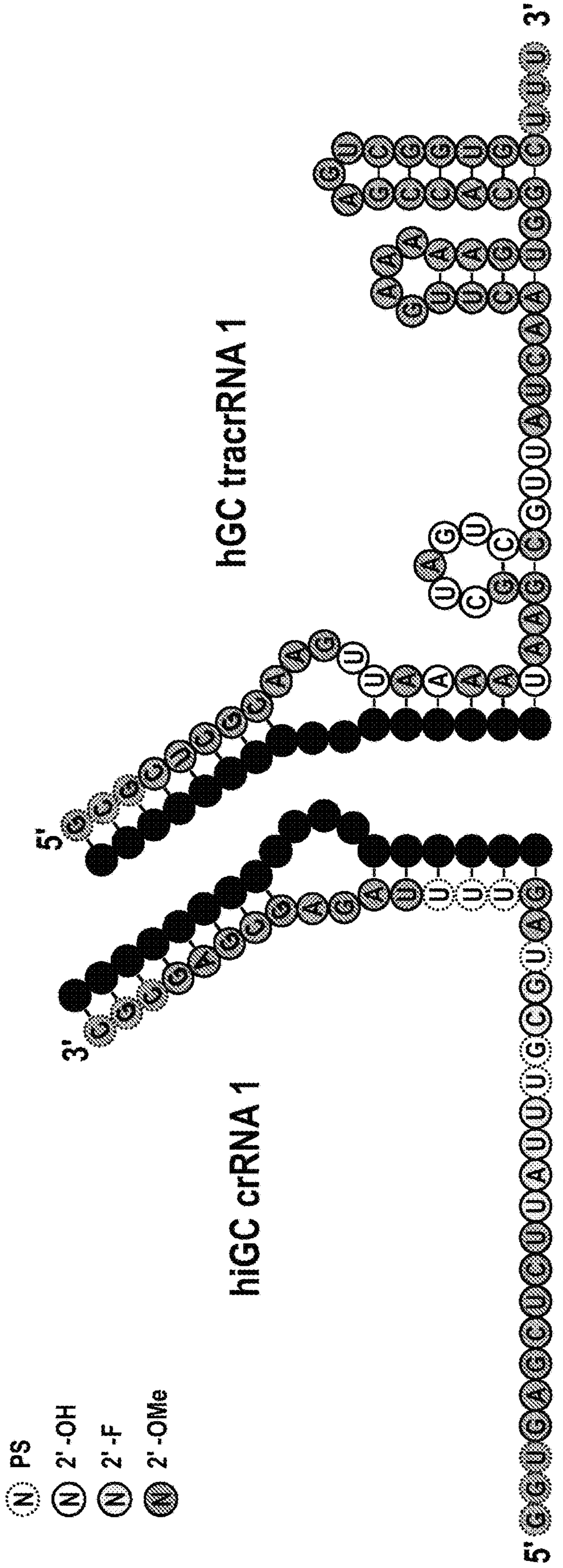
FIG. 9 depicts a schematic of a crRNA with modifications in the repeat region and tracrRNA with modifications in the anti-stem region, including increased GC content and ribose sugar modifications, such as 2'-Fluoro and 2'-O-methyl modifications.

The use of a modular, or dual RNA, guide RNA approach over a single guide RNA (sgRNA) approach has several advantages, including the ease of making the shorter crRNA and tracrRNA relative to a longer sgRNA, and the reduced cost of manufacturing the dual RNAs relative to the sgRNA. Exemplary crRNAs and tracrRNAs with modifications in the repeat and anti-repeat region, including a high GC content and 2'-Fluoro modifications, are shown in Table 2 and Table 3 below, and at FIG. 9.

TABLE 2

Exemplary modified repeat crRNAs.

| Name | SEQ ID NO: | Sequence |
|---|---|---|
| hiGC crRNA 1 | 60 | mG#mG#mU#mGmAmGmCmUmCmUfUfAfUfUrU#rG#fCfGrU#mAmGrU#rU#rU#fUfAmGmAmGmCmGmAmG#mC#mG#mC |
| hiGC crRNA 2 | 61 | mG#mG#mU#mGmAmGmCmUmCmUfUfAfUfUrU#rG#fCfGrU#mAmGrU#rU#rU#fUfAmGmAfGfCfGfAfG#fC#mG#mC |
| hiGC crRNA 3 | 62 | mG#mG#mU#mGmAmGmCmUmCmUfUfAfUfUrU#rG#fCfGrU#mAmGrU#rU#rU#fUfAmGmAfGmCfGmAfG#mC#mG#mC |
| hiGC crRNA 4 | 63 | mG#mG#mU#mGmAmGmCmUmCmUfUfAfUfUrU#rG#fCfGrU#mAfGrU#rU#rU#fUfAmGmAfGmCfGmAfG#mC#mG#mC |

KEY: rN = RNA, mN = 2'-O-methyl RNA, fN = 2'-fluoro RNA N#N = phosphorothioate linkage

TABLE 3

Exemplary modified repeat tracrRNAs

| Name | SEQ ID NO: | Sequence |
|---|---|---|
| hiGC tracrRNA 1 | 37 | mG#mC#mG#mCmUmCmGmCmAmAmGrUrUmArAmAmArUmAmAmGmGrCrUmArGrUrCmCrGrUrUmAmUmCmAmAmCmUmUmGmAmAmAmAmAmGmUmGmGmCmAmCmCmGmAmGmUmCmGmGmUmGmC#mU#mU#mU |
| hiGC tracrRNA 2 | 38 | mG#mC#fG#fCfUfCfGfCmAmAmGrUrUmArAmAmArUmAmAmGmGrCrUmArGrUrCmCrGrUrUmAmUmCmAmAmCmUmUmGmAmAmAmAmAmGmUmGmGmCmAmCmCmGmAmGmUmCmGmGmUmGmC#mU#mU#mU |
| hiGC tracrRNA 3 | 39 | mG#mC#fG#mCfUmCfGmCmAmAmGrUrUmArAmAmArUmAmAmGmGrCrUmArGrUrCmCrGrUrUmAmUmCmAmAmCmUmUmGmAmAmAmAmAmGmUmGmGmCmAmCmCmGmAmGmUmCmGmGmUmGmC#mU#mU#mU |
| hiGC tracrRNA 4 | 40 | mG#mC#fG#mCfUmCfGmCmAmAmGrUrUfArAfAfArUmAmAmGmGrCrUmArGrUrCmCrGrUrUmAmUmCmAmAmCmUmUmGmAmAmAmAmAmGmUmGmGmCmAmCmCmGmAmGmUmCmGmGmUmGmC#mU#mU#mU |

KEY: rN = RNA, mN = 2'-O-mcthyl RNA, fN = 2'-fluoro RNA N#N = phosphorothioate linkage Guide RNA Conjugates The chemically modified guide RNAs of the disclosure may be modified with terminally conjugated moieties. As used herein, a "terminally conjugated moiety" or "moiety" refers to a compound which may be linked or attached to the 5' and/or 3' end of the crRNA and/or tracrRNA of a guide RNA. Terminally conjugated moieties can provide increased stability, increased ability to penetrate cell membranes, increase cellular uptake, increase circulation time in vivo, act as a cell-specific directing reagent, and/or provide a means to monitor cellular or tissue-specific uptake.

Terminally conjugated moieties may be conjugated on the 5' end and/or the 3' end of a crRNA and/or a tracrRNA, as, for example, in FIGS. 14A-14D.

In certain exemplary embodiments, a terminally conjugated moiety includes, but is not limited to, fatty acid, steroid, secosteroid, lipid, ganglioside analog, nucleoside analogs, endocannabinoid, vitamin, receptor ligand, peptide, aptamer, alkyl chain, fluorophore, antibody, nuclear localization signal, and the like.

In certain exemplary embodiments, a terminally conjugated moiety includes, but is not limited to, cholesterol, cholesterol-triethylene glycol (TEGChol), docosahexaenoic acid (DHA), docosanoic acid (DCA), lithocholic acid (LA), GalNAc, amphiphilic block copolymer (ABC), hydrophilic block copolymer (HBC), poloxamer, Cy5, Cy3, and the like.

In certain exemplary embodiments, the at least one terminally conjugated moiety is a modified lipid, including a branched lipid (such as the structure shown in Formula I) or a headgroup-modified lipid (such as the structure shown in Formula II).

X-MC(═Y)M-Z-[L-MC(═Y)M-R]n    Formula I:

where X is a moiety that links the lipid to the guide RNA, each Y is independently oxygen or sulfur, each M is independently $CH_2$, NH, O or S, Z is a branching group which allows two or three ("n") chains to be joined to the rest of the structure, L is an optional linker moiety, and each R is independently a saturated, monounsaturated or polyunsaturated linear or branched moiety from 2 to 30 atoms in length, a sterol, or other hydrophobic group.

X-MC(═Y)M-Z-[L-MC(═Y)M-R]n-L-K-J    Formula II:

where X is a moiety that links the lipid to the guide RNA, each Y is independently oxygen or sulfur, each M is independently $CH_2$, NH, N-alkyl, O or S, Z is a branching group which allows two or three ("n") chains to be joined to the rest of the structure, each L is independently an optional linker moiety, and R is a saturated, monounsaturated or polyunsaturated linear or branched moiety from 2 to 30 atoms in length, a sterol, or other hydrophobic group, K is a phosphate, sulfate, or amide and J is an aminoalkane or quaternary aminoalkane group.

The moieties may be attached to the terminal nucleotides of the guide RNA via a linker. Exemplary linkers include, but are not limited to, an ethylene glycol chain, an alkyl chain, a polypeptide, a polysaccharide, a block copolymer, and the like.

Exemplary crRNAs and tracrRNAs with conjugated moieties may be found in Table 4 below.

TABLE 4

Exemplary crRNAs and tracrRNAs with conjugated moieties.

| Name | SEQ ID NO: | Sequence |
|---|---|---|
| crRNA 12 | 64 | Cy3-mG#mG#mU#mGmAmGmCmUmCmUfUfAfUfUrU#rG#fCfGrU#mAmGrU#rU#rU#mUmAmGmAmGmCmUmAmU#mG#mC#mU |
| crRNA 13 | 65 | Cy3-mG#mG#mU#mGmAmGmCmUmCmUfUfAfUfUrU#rG#rC#rG#rU#mAmGrU#rU#rU#mUmAmGmAmGmCmUmAmU#mG#mC#mU |
| crRNA 14 | 66 | Cy3-mG#mG#mU#mGmAmGmCmUmCmUfUfAfUfUrU#rG#fCfGrU#mAmGrU#rU#rU#mUmAmGmAmGmCmUmAmU#mG#mC#mU-TegChol |
| crRNA 15 | 67 | Cy3-mG#mG#mU#mGmAmGmCmUmCmUfUfAfUfUrU#rG#rC#rG#rU#mAmGrU#rU#rU#mUmAmGmAmGmCmUmAmU#mG#mC#mU-TegChol |
| crRNA 16 | 68 | Cy3-mG#mG#mU#mGmAmGmCmUmCmUfUfAfUfUrU#rG#fCfGrU#mAmGrU#rU#rU#mUmAmGmAmGmCmUmAmU#mG#mC#mU-GalNAc |
| tracrRNA 5 | 59 | mA#mG#mC#mAmUmAmGmCmAmAmGrUrUmAmAmAmArUmAmAmGmGrCrUmArGrUrCmCrGrUrUmAmUmCmAmAmCmUmUmGmAmAmAmAmAmGmUmGmGmCmAmCmCmGmAmGmUmCmGmGmUmGmC#mU#mU#mU-TegChol |
| hiGC tracrRNA 1-5'chol | 69 | Chol-linker-mG#mC#mG#mCmUmCmGmCmAmAmGrUrUmArAmAmArUmAmAmGmGrCrUmArGrUrCmCrGrUrUmAmUmCmAmAmCmUmUmGmAmAmAmAmAmGmUmGmGmCmAmCmCmGmAmGmUmCmGmGmUmGmC#mU#mU#mU |
| hiGC tracrRNA 1-2xchol | 70 | chol-linker-mG#mC#mG#mCmUmCmGmCmAmAmGrUrUmArAmAmArUmAmAmGmGrCrUmArGrUrCmCrGrUrUmAmUmCmAmAmCmUmUmGmAmAmAmAmAmGmUmGmGmCmAmCmCmGmAmGmUmCmGmGmUmGmC#mU#mU#mU-linker-chol |
| hiGC tracrRNA 1-3'chol | 71 | mG#mC#mG#mCmUmCmGmCmAmAmGrUrUmArAmAmArUmAmAmGmGrCrUmArGrUrCmCrGrUrUmAmUmCmAmAmCmUmUmGmAmAmAmAmAmGmUmGmGmCmAmCmCmGmAmGmUmCmGmGmUmGmC#mU#mU#mU-linker-chol |
| hiGC tracrRNA 1-5'galnac | 72 | galnac-linker-mG#mC#mG#mCmUmCmGmCmAmAmGrUrUmArAmAmArUmAmAmGmGrCrUmArGrUrCmCrGrUrUmAmUmCmAmAmCmUmUmGmAmAmAmAmAmGmUmGmGmCmAmCmCmGmAmGmUmCmGmGmUmGmC#mU#mU#mU |
| hiGC tracrRNA 1-2xgalnac | 73 | galnac-linker-mG#mC#mG#mCmUmCmGmCmAmAmGrUrUmArAmAmArUmAmAmGmGrCrUmArGrUrCmCrGrUrUmAmUmCmAmAmCmUmUmGmAmAmAmAmAmGmUmGmGmCmAmCmCmGmAmGmUmCmGmGmUmGmC#mU#mU#mU-linker-galnac |

TABLE 4-continued

| Exemplary crRNAs and tracrRNAs with conjugated moieties. | | |
|---|---|---|
| Name | SEQ ID NO: | Sequence |
| hiGC tracrRNA 1-3'galnac | 74 | mG#mC#mG#mCmUmCmGmCmAmAmGrUrUmArAmAmAr UmAmAmGmGrCrUmArGrUrCmCrGrUrUmAmUmCmAmA mCmUmUmGmAmAmAmAmAmGmUmGmGmCmAmCmC mGmAmGmUmCmGmGmUmGmC#mU#mU#mU-linker-galnac |
| hiGC tracrRNA 1-5'DHA | 75 | DHA-linker-mG#mC#mG#mCmUmCmGmCmAmAmGrUrUmArAmAmAr UmAmAmGmGrCrUmArGrUrCmCrGrUrUmAmUmCmAmA mCmUmUmGmAmAmAmAmAmGmUmGmGmCmAmCmC mGmAmGmUmCmGmGmUmGmC#mU#mU#mU |
| hiGC tracrRNA 1-2x DHA | 76 | DHA-linker-mG#mC#mG#mCmUmCmGmCmAmAmGrUrUmArAmAmAr UmAmAmGmGrCrUmArGrUrCmCrGrUrUmAmUmCmAmA mCmUmUmGmAmAmAmAmAmGmUmGmGmCmAmCmC mGmAmGmUmCmGmGmUmGmC#mU#mU#mU-linker-DHA |
| hiGC tracrRNA 1-3' DHA | 77 | mG#mC#mG#mCmUmCmGmCmAmAmGrUrUmArAmAmAr UmAmAmGmGrCrUmArGrUrCmCrGrUrUmAmUmCmAmA mCmUmUmGmAmAmAmAmAmGmUmGmGmCmAmCmC mGmAmGmUmCmGmGmUmGmC#mU#mU#mU-linker-DHA |
| hiGC tracrRNA 1-5'DCA | 78 | DCA-linker-mG#mC#mG#mCmUmCmGmCmAmAmGrUrUmArAmAmAr UmAmAmGmGrCrUmArGrUrCmCrGrUrUmAmUmCmAmA mCmUmUmGmAmAmAmAmAmGmUmGmGmCmAmCmC mGmAmGmUmCmGmGmUmGmC#mU#mU#mU |
| hiGC tracrRNA 1-2xc DCA | 79 | DCA-linker-mG#mC#mG#mCmUmCmGmCmAmAmGrUrUmArAmAmAr UmAmAmGmGrCrUmArGrUrCmCrGrUrUmAmUmCmAmA mCmUmUmGmAmAmAmAmAmGmUmGmGmCmAmCmC mGmAmGmUmCmGmGmUmGmC#mU#mU#mU-linker-DCA |
| hiGC tracrRNA 1-3' DCA | 80 | mG#mC#mG#mCmUmCmGmCmAmAmGrUrUmArAmAmAr UmAmAmGmGrCrUmArGrUrCmCrGrUrUmAmUmCmAmA mCmUmUmGmAmAmAmAmAmGmUmGmGmCmAmCmC mGmAmGmUmCmGmGmUmGmC#mU#mU#mU-linker-DCA |
| hiGC tracrRNA 1-5'LA | 81 | LA-linker-mG#mC#mG#mCmUmCmGmCmAmAmGrUrUmArAmAmAr UmAmAmGmGrCrUmArGrUrCmCrGrUrUmAmUmCmAmA mCmUmUmGmAmAmAmAmAmGmUmGmGmCmAmCmC mGmAmGmUmCmGmGmUmGmC#mU#mU#mU |
| hiGC tracrRNA 1-2x LA | 82 | LA-linker-mG#mC#mG#mCmUmCmGmCmAmAmGrUrUmArAmAmAr UmAmAmGmGrCrUmArGrUrCmCrGrUrUmAmUmCmAmA mCmUmUmGmAmAmAmAmAmGmUmGmGmCmAmCmC mGmAmGmUmCmGmGmUmGmC#mU#mU#mU-linker-LA |
| hiGC tracrRNA 1-3' LA | 83 | mG#mC#mG#mCmUmCmGmCmAmAmGrUrUmArAmAmAr UmAmAmGmGrCrUmArGrUrCmCrGrUrUmAmUmCmAmA mCmUmUmGmAmAmAmAmAmGmUmGmGmCmAmCmC mGmAmGmUmCmGmGmUmGmC#mU#mU#mU-linker-LA |
| hiGC tracrRNA 1-5'ABC | 84 | ABC-linker-mG#mC#mG#mCmUmCmGmCmAmAmGrUrUmArAmAmAr UmAmAmGmGrCrUmArGrUrCmCrGrUrUmAmUmCmAmA mCmUmUmGmAmAmAmAmAmGmUmGmGmCmAmCmC mGmAmGmUmCmGmGmUmGmC#mU#mU#mU |
| hiGC tracrRNA 1-2x ABC | 85 | ABC-linker-mG#mC#mG#mCmUmCmGmCmAmAmGrUrUmArAmAmAr UmAmAmGmGrCrUmArGrUrCmCrGrUrUmAmUmCmAmA mCmUmUmGmAmAmAmAmAmGmUmGmGmCmAmCmC mGmAmGmUmCmGmGmUmGmC#mU#mU#mU-linker-ABC |
| hiGC tracrRNA 1-3' ABC | 86 | mG#mC#mG#mCmUmCmGmCmAmAmGrUrUmArAmAmAr UmAmAmGmGrCrUmArGrUrCmCrGrUrUmAmUmCmAmA mCmUmUmGmAmAmAmAmAmGmUmGmGmCmAmCmC mGmAmGmUmCmGmGmUmGmC#mU#mU#mU-linker-ABC |
| hiGC tracrRNA 1-5'HBC | 87 | HBC-linker-mG#mC#mG#mCmUmCmGmCmAmAmGrUrUmArAmAmAr UmAmAmGmGrCrUmArGrUrCmCrGrUrUmAmUmCmAmA mCmUmUmGmAmAmAmAmAmGmUmGmGmCmAmCmC mGmAmGmUmCmGmGmUmGmC#mU#mU#mU |

TABLE 4-continued

| Exemplary crRNAs and tracrRNAs with conjugated moieties. | | |
|---|---|---|
| Name | SEQ ID NO: | Sequence |
| hiGC tracrRNA 1-2x HBC | 88 | HBC-linker-mG#mC#mG#mCmUmCmGmCmAmAmGrUrUmArAmAmArUmAmAmGmGrCrUmArGrUrCmCrGrUrUmAmUmCmAmAmCmUmUmGmAmAmAmAmAmGmUmGmGmCmAmCmCmGmAmGmUmCmGmGmUmGmC#mU#mU#mU-linker-HBC |
| hiGC tracrRNA 1-3' HBC | 89 | mG#mC#mG#mCmUmCmGmCmAmAmGrUrUmArAmAmArUmAmAmGmGrCrUmArGrUrCmCrGrUrUmAmUmCmAmAmCmUmUmGmAmAmAmAmAmGmUmGmGmCmAmCmCmGmAmGmUmCmGmGmUmGmC#mU#mU#mU-linker-HBC |
| hiGC tracrRNA 1-5'Pol | 90 | Pol-linker-mG#mC#mG#mCmUmCmGmCmAmAmGrUrUmArAmAmArUmAmAmGmGrCrUmArGrUrCmCrGrUrUmAmUmCmAmAmCmUmUmGmAmAmAmAmAmGmUmGmGmCmAmCmCmGmAmGmUmCmGmGmUmGmC#mU#mU#mU |
| hiGC tracrRNA 1-2xPol | 91 | Pol-linker-mG#mC#mG#mCmUmCmGmCmAmAmGrUrUmArAmAmArUmAmAmGmGrCrUmArGrUrCmCrGrUrUmAmUmCmAmAmCmUmUmGmAmAmAmAmAmGmUmGmGmCmAmCmCmGmAmGmUmCmGmGmUmGmC#mU#mU#mU-linker-Pol |
| hiGC tracrRNA 1-3'Pol | 92 | mG#mC#mG#mCmUmCmGmCmAmAmGrUrUmArAmAmArUmAmAmGmGrCrUmArGrUrCmCrGrUrUmAmUmCmAmAmCmUmUmGmAmAmAmAmAmGmUmGmGmCmAmCmCmGmAmGmUmCmGmGmUmGmC#mU#mU#mU-linker-Pol |
| hiGC crRNA 1 1-5'chol | 93 | Chol-linker-mG#mG#mU#mGmAmGmCmUmCmUfUfAfUfUrU#rG#fCfGrU#mAmGrU#rU#rU#fUfAmGmAmGmCmGmAmG#mC#mG#mC |
| hiGC crRNA 1 1-2xchol | 94 | chol-linker-mG#mG#mU#mGmAmGmCmUmCmUfUfAfUfUrU#rG#fCfGrU#mAmGrU#rU#rU#fUfAmGmAmGmCmGmAmG#mC#mG#mC -linker-chol |
| hiGC crRNA 1 1-3'chol | 95 | mG#mG#mU#mGmAmGmCmUmCmUfUfAfUfUrU#rG#fCfGrU#mAmGrU#rU#rU#fUfAmGmAmGmCmGmAmG#mC#mG#mC -linker-chol |
| hiGC crRNA 1 1-5'galnac | 96 | galnac-linker-mG#mG#mU#mGmAmGmCmUmCmUfUfAfUfUrU#rG#fCfGrU#mAmGrU#rU#rU#fUfAmGmAmGmCmGmAmG#mC#mG#mC |
| hiGC crRNA 1 1-2xgalnac | 97 | galnac-linker-mG#mG#mU#mGmAmGmCmUmCmUfUfAfUfUrU#rG#fCfGrU#mAmGrU#rU#rU#fUfAmGmAmGmCmGmAmG#mC#mG#mC -linker-galnac |
| hiGC crRNA 1 1-3'galnac | 98 | mG#mG#mU#mGmAmGmCmUmCmUfUfAfUfUrU#rG#fCfGrU#mAmGrU#rU#rU#fUfAmGmAmGmCmGmAmG#mC#mG#mC -linker-galnac |
| hiGC crRNA 1 1-5'DHA | 99 | DHA-linker-mG#mG#mU#mGmAmGmCmUmCmUfUfAfUfUrU#rG#fCfGrU#mAmGrU#rU#rU#fUfAmGmAmGmCmGmAmG#mC#mG#mC |
| hiGC crRNA 1 1-2x DHA | 100 | DHA-linker-mG#mG#mU#mGmAmGmCmUmCmUfUfAfUfUrU#rG#fCfGrU#mAmGrU#rU#rU#fUfAmGmAmGmCmGmAmG#mC#mG#mC -linker-DHA |
| hiGC crRNA 1 1-3' DHA | 101 | mG#mG#mU#mGmAmGmCmUmCmUfUfAfUfUrU#rG#fCfGrU#mAmGrU#rU#rU#fUfAmGmAmGmCmGmAmG#mC#mG#mC -linker-DHA |
| hiGC crRNA 1 1-5'DCA | 102 | DCA-linker-mG#mG#mU#mGmAmGmCmUmCmUfUfAfUfUrU#rG#fCfGrU#mAmGrU#rU#rU#fUfAmGmAmGmCmGmAmG#mC#mG#mC |
| hiGC crRNA 1 1-2xc DCA | 103 | DCA-linker-mG#mG#mU#mGmAmGmCmUmCmUfUfAfUfUrU#rG#fCfGrU#mAmGrU#rU#rU#fUfAmGmAmGmCmGmAmG#mC#mG#mC -linker-DCA |
| hiGC crRNA 1 1-3' DCA | 104 | mG#mG#mU#mGmAmGmCmUmCmUfUfAfUfUrU#rG#fCfGrU#mAmGrU#rU#rU#fUfAmGmAmGmCmGmAmG#mC#mG#mC -linker-DCA |
| hiGC crRNA 1 1-5'LA | 105 | LA-linker-mG#mG#mU#mGmAmGmCmUmCmUfUfAfUfUrU#rG#fCfGrU#mAmGrU#rU#rU#fUfAmGmAmGmCmGmAmG#mC#mG#mC |

TABLE 4-continued

Exemplary crRNAs and tracrRNAs with conjugated moieties.

| Name | SEQ ID NO: | Sequence |
|---|---|---|
| hiGC crRNA 1 1-2x LA | 106 | LA-linker-mG#mG#mU#mGmAmGmCmUmCmUfUfAfUfUrU#rG#fCfG rU#mAmGrU#rU#rU#fUfAmGmAmGmCmGmAmG#mC#mG #mC -linker-LA |
| hiGC crRNA 1 1-3' LA | 107 | mG#mG#mU#mGmAmGmCmUmCmUfUfAfUfUrU#rG#fCfG rU#mAmGrU#rU#rU#fUfAmGmAmGmCmGmAmG#mC#mG #mC -linker-LA |
| hiGC crRNA 1 1-5'ABC | 108 | ABC-linker-mG#mG#mU#mGmAmGmCmUmCmUfUfAfUfUrU#rG#fCfG rU#mAmGrU#rU#rU#fUfAmGmAmGmCmGmAmG#mC#mG #mC |
| hiGC crRNA 1 1-2x ABC | 109 | ABC-linker-mG#mG#mU#mGmAmGmCmUmCmUfUfAfUfUrU#rG#fCfG rU#mAmGrU#rU#rU#fUfAmGmAmGmCmGmAmG#mC#mG #mC -linker-ABC |
| hiGC crRNA 1 1-3' ABC | 110 | mG#mG#mU#mGmAmGmCmUmCmUfUfAfUfUrU#rG#fCfG rU#mAmGrU#rU#rU#fUfAmGmAmGmCmGmAmG#mC#mG #mC -linker-ABC |
| hiGC crRNA 1 1-5'HBC | 111 | HBC-linker-mG#mG#mU#mGmAmGmCmUmCmUfUfAfUfUrU#rG#fCfG rU#mAmGrU#rU#rU#fUfAmGmAmGmCmGmAmG#mC#mG #mC |
| hiGC crRNA 1 1-2x HBC | 112 | HBC-linker-mG#mG#mU#mGmAmGmCmUmCmUfUfAfUfUrU#rG#fCfG rU#mAmGrU#rU#rU#fUfAmGmAmGmCmGmAmG#mC#mG #mC -linker-HBC |
| hiGC crRNA 1 1-3' HBC | 113 | mG#mG#mU#mGmAmGmCmUmCmUfUfAfUfUrU#rG#fCfG rU#mAmGrU#rU#rU#fUfAmGmAmGmCmGmAmG#mC#mG #mC -linker-HBC |
| hiGC crRNA 1 1-5'Pol | 114 | Pol-linker-mG#mG#mU#mGmAmGmCmUmCmUfUfAfUfUrU#rG#fCfG rU#mAmGrU#rU#rU#fUfAmGmAmGmCmGmAmG#mC#mG #mC |
| hiGC crRNA 1 1-2xPol | 115 | Pol-linker-mG#mG#mU#mGmAmGmCmUmCmUfUfAfUfUrU#rG#fCfG rU#mAmGrU#rU#rU#fUfAmGmAmGmCmGmAmG#mC#mG #mC -linker-Pol |
| hiGC crRNA 1 1-3'Pol | 116 | mG#mG#mU#mGmAmGmCmUmCmUfUfAfUfUrU#rG#fCfG rU#mAmGrU#rU#rU#fUfAmGmAmGmCmGmAmG#mC#mG #mC -linker-Pol |

KEY: rN = RNA, mN = 2'-O-methyl RNA, fN = 2'-fluoro RNA N#N = phosphorothioate linkage Where: Chol-cholesterol; GalNAc—(N-Acetylgalactosamine) 3-40 moieties; DHA-Docosahexaenoic Acid; DCA-Docosanoic Acid; LA-lithocholic Acid; ABC-Amphiphilic block copolymer (PK modifier); HBC-Hydrophilic block copolymer (PK modifier); and Pol-poloxamers (PK modifier).

Chemically Modified Single Guide RNA

Figure 15:
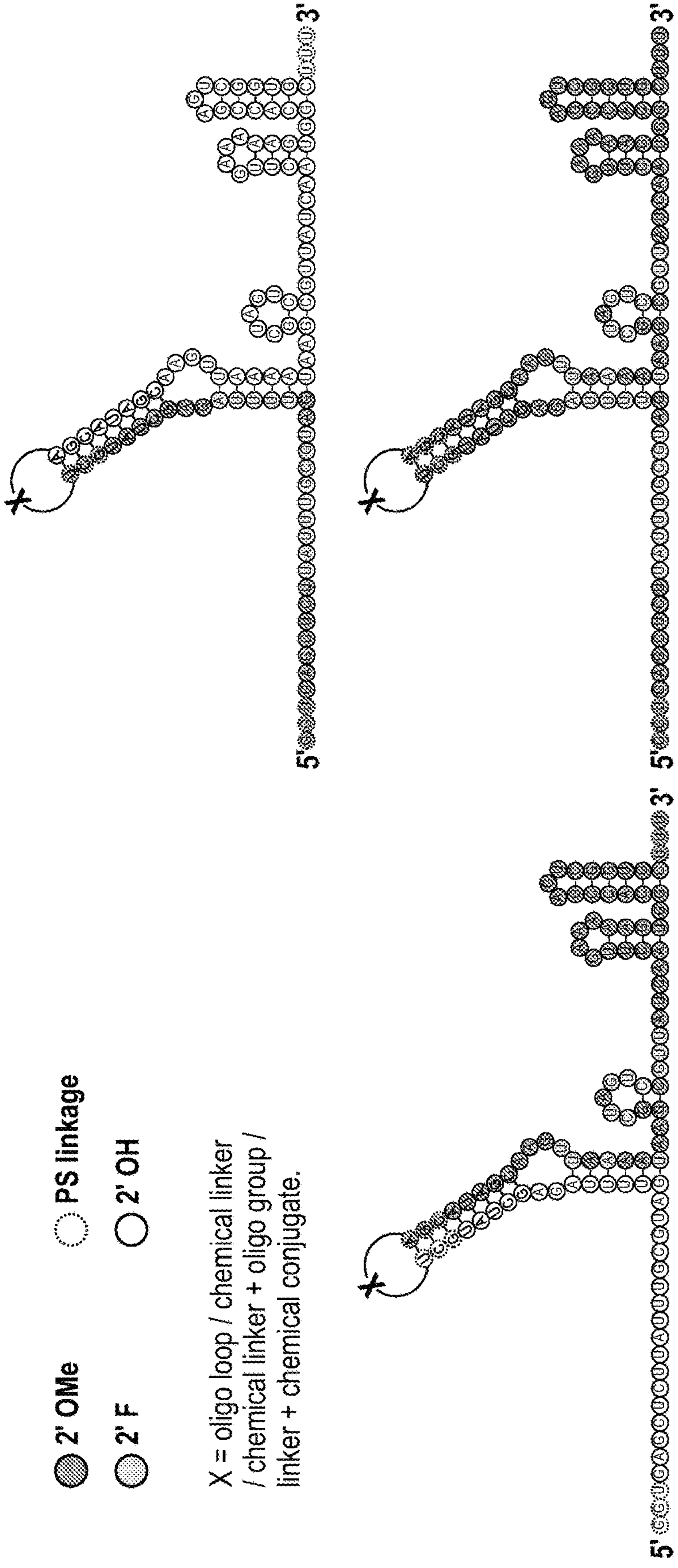
FIG. 15 depicts a schematic of crRNAs and tracrRNAs linked at the 3' end of the crRNA and the 5' end of the tracrRNA to form a single guide RNA (sgRNA).

As described herein, the chemically modified guide RNAs of the disclosure may be constructed as single guide RNAs (sgRNAs) by linking the 3' end of a crRNA to the 5' end of a tracrRNA. The linker may be an oligonucleotide loop, including a chemically modified oligonucleotide loop. The linker may be a non-nucleotide chemical linker, including, but not limited to, ethylene glycol oligomers (see, e.g., Pils et al. Nucleic Acids Res. 28 (9): 1859-1863 (2000)). FIG. 15 of the disclosure depicts a schematic of the chemically modified crRNAs and tracrRNAs linked to form a chemically modified sgRNA.

RNA-Guided Nucleases

RNA-guided nucleases according to the present disclosure include, without limitation, naturally-occurring Type II CRISPR nucleases such as Cas9, as well as other nucleases derived or obtained therefrom. Exemplary Cas9 nucleases that may be used in the present disclosure include, but are not limited to, *S. pyogenes* Cas9 (SpCas9), *S. aureus* Cas9 (SaCas9), *N. meningitidis* Cas9 (NmCas9), *C. jejuni* Cas9 (CjCas9), and *Geobacillus* Cas9 (GeoCas9). In functional terms, RNA-guided nucleases are defined as those nucleases that: (a) interact with (e.g., complex with) a gRNA; and (b) together with the gRNA, associate with, and optionally cleave or modify, a target region of a DNA that includes (i) a sequence complementary to the targeting domain of the gRNA and, optionally, (ii) an additional sequence referred to as a "protospacer adjacent motif," or "PAM," which is described in greater detail below. As the following examples will illustrate, RNA-guided nucleases can be defined, in broad terms, by their PAM specificity and cleavage activity, even though variations may exist between individual RNA-guided nucleases that share the same PAM specificity or cleavage activity. Skilled artisans will appreciate that some aspects of the present disclosure relate to systems, methods and compositions that can be implemented using any suitable RNA-guided nuclease having a certain PAM specificity and/or cleavage activity. For this reason, unless otherwise specified, the term RNA-guided nuclease should be understood as a generic term, and not limited to any particular type (e.g., Cas9 vs. Cpf1), species (e.g., *S. pyogenes* vs. *S. aureus*) or variation (e.g., full-length vs. truncated or split; naturally-occurring PAM specificity vs. engineered PAM specificity).

Various RNA-guided nucleases may require different sequential relationships between PAMs and protospacers. In general, Cas9s recognize PAM sequences that are 5' of the protospacer as visualized relative to the top or complementary strand.

In addition to recognizing specific sequential orientations of PAMs and protospacers, RNA-guided nucleases generally recognize specific PAM sequences. *S. aureus* Cas9, for example, recognizes a PAM sequence of NNGRRT, wherein the N sequences are immediately 3' of the region recognized by the gRNA targeting domain. *S. pyogenes* Cas9 recognizes NGG PAM sequences. It should also be noted that engineered RNA-guided nucleases can have PAM specificities that differ from the PAM specificities of similar nucleases (such as the naturally occurring variant from which an RNA-guided nuclease is derived, or the naturally occurring variant having the greatest amino acid sequence homology to an engineered RNA-guided nuclease). Modified Cas9s that recognize alternate PAM sequences are described below.

RNA-guided nucleases are also characterized by their DNA cleavage activity: naturally-occurring RNA-guided nucleases typically form DSBs in target nucleic acids, but engineered variants have been produced that generate only SSBs (discussed above; see also Ran 2013, incorporated by reference herein), or that do not cut at all.

The RNA-guided nuclease Cas9 may be a variant of Cas9 with altered activity. Exemplary variant Cas9 nucleases include, but are not limited to, a Cas9 nickase (nCas9), a catalytically dead Cas9 (dCas9), a hyper accurate Cas9 (HypaCas9) (Chen et al. Nature, 550 (7676), 407-410 (2017)), a high fidelity Cas9 (Cas9-HF) (Kleinstiver et al. Nature 529 (7587), 490-495 (2016)), an enhanced specificity Cas9 (eCas9) (Slaymaker et al. Science 351 (6268), 84-88 (2016)), and an expanded PAM Cas9 (xCas9) (Hu et al. Nature doi: 10.1038/nature26155 (2018)).

The RNA-guided nucleases may be combined with the chemically modified guide RNAs of the present disclosure to form a genome-editing system. The RNA-guided nucleases may be combined with the chemically modified guide RNAs to form an RNP complex that may be delivered to a cell where genome-editing is desired. The RNA-guided nucleases may be expressed in a cell where genome-editing is desired with the chemically modified guide RNAs delivered separately. For example, the RNA-guided nucleases may be expressed from a polynucleotide such as a vector or a synthetic mRNA. The vector may be a viral vector, including, be not limited to, an adeno-associated virus (AAV) vector or a lentivirus (LV) vector.

It will be readily apparent to those skilled in the art that other suitable modifications and adaptations of the methods described herein may be made using suitable equivalents without departing from the scope of the embodiments disclosed herein. Having now described certain embodiments in detail, the same will be more clearly understood by reference to the following examples, which are included for purposes of illustration only and are not intended to be limiting.

EXAMPLES

Example 1—Synthesis of Chemically Modified Crrna and Tracrrna crRNAs and tracrRNAs were synthesized at 1 μmole scale on an Applied Biosystems 394 DNA synthesizer. BTT (0.25 M in acetonitrile, ChemGenes) was used as activator. 0.05 M iodine in pyridine:water (9:1) (TEDIA) was used as oxidizer. DDTT (0.1 M, ChemGenes) was used as sulfurizing agent. 3% TCA in DCM (TEDIA) was used as deblock solution. RNAs were grown on 1000 Å CPG functionalized with Unylinker (~42 μmol/g). RNA and 2'-OMe phosphoramidites (ChemGenes) were dissolved in acetonitrile to 0.15 M; the coupling time was 10 min for each base. The nucleobases were deprotected with a 3:1 $NH_4OH$:EtOH solution for 48 hours at room temperature. Deprotection of the TBDMS group was achieved with DMSO:NEt3·3HF (4:1) solution (500 μL) at 65° C. for 3 hours. RNA oligonucleotides were then recovered by precipitation in 3M NaOAc (25 μL) and n-BuOH (1 mL), and the pellet was washed with cold 70% EtOH and resuspended in 1 mL RNase-free water.

Purification of the crRNAs and tracrRNAs were carried out by high performance liquid chromatography using a 1260 infinity system with an Agilent PL-SAX 1000 Å column (150×7.5 mm, 8 μm). Buffer A: 30% acetonitrile in water; Buffer B: 30% acetonitrile in IM NaCl04 (aq). Excess salt was removed with a Sephadex Nap-10 column.

crRNAs and tracrRNAs were analyzed on an Agilent 6530 Q-TOF LC/MS system with electrospray ionization and time of flight ion separation in negative ionization mode. The data were analyzed using Agilent Mass Hunter software. Buffer A: 100 mM hexafluoroisopropanol with 9 mM triethylamine in water; Buffer B: 100 mM hexafluoroisopropanol with 9 mM trimethylamine in methanol.

Example 2—Genome Editing Efficiency of Chemically Modified crRNA and tracrRNA crRNA and tracrRNA were extensively modified while retaining the efficacy of SpyCas9-based genome editing in cultured human cells. Structure-guided and systematic approaches were used to introduce 2'-OMe-RNA, 2'-F-RNA and PS modifications throughout guide RNAs (Table 5 and Table 6). The strategy described herein yielded active RNP complexes with both extensively and fully modified versions of crRNAs and tracrRNAs.

TABLE 5

Heavily and fully chemically modified crRNAs and tracrRNAs.

| Name | SEQ ID NO: | Sequence | Extinction Coefficient | MW (Observed/ Calculated) |
|---|---|---|---|---|
| C1 | 41 | mG#mG#mU#mGmAmGmCmUmCmUrUrA rUrUrUmGmCmGrUmAmGrUrUrUmUmA mGmAmGmCmUmAmU#mG#mCmU | 352710 | 11942.8/11942.8 |
| C2 | 42 | rGrGrUrGrArGmCmUmCmUrUrArUrUrG rCrGrUmAmGrUrUrUrUrAmGmAmGmCm UmAmU#mG#mCmU | 352710 | 11739.6/11740.3 |

TABLE 5-continued

| Name | SEQ ID NO: | Sequence | Extinction Coefficient | MW (Observed/ Calculated) |
|---|---|---|---|---|
| | | Heavily and fully chemically modified crRNAs and tracrRNAs. | | |
| C3 | 43 | rG#rG#rU#rGrArGmCmUmCmUrUrArUrUrUrGrCrGrUmAmGrUrUrUrAmGmAmGmCmUmAmU#mG#mCmU | 352710 | 11788.5/11788.5 |
| C4 | 44 | mG#mG#mU#mGmAmGmCmUmCmUrUrArUrUrUrGrCrGrUmAmGrUrUrUrAmGmAmGmCmUmAmU#mG#mC#mU | 352710 | 11888.6/11888.7 |
| C5 | 45 | rG#rG#rU#rGrArGmCmUmCmUrUrArUrUrUrGmCmGrUmAmGrUrUrUrAmGmAmGmCmUmAmU#mG#mC#mU | 352710 | 11832.6/11832.6 |
| C6 | 46 | rG#rG#rU#rGrArGmCmUmCmUrUrArUrUrUrGrCrGrUmAmGrUrUrUmUmAmGmAmGmCmUmAmU#mG#mC#mU | 352710 | 11832.6/11832.6 |
| C7 | 47 | mG#mG#mU#mGmAmGmCmUmCmUrUrArUrUrUrGmCmGrUmAmGrUrUrUrAmGmAmGmCmUmAmU#mG#mC#mU | 352710 | 11916.7/11916.8 |
| C8 | 48 | mG#mG#mU#mGmAmGmCmUmCmUrUrArUrUrUrGrCrGrUmAmGrUrUrUmUmAmGmAmGmCmUmAmU#mG#mC#mU | 352710 | 11916.6/11916.8 |
| C9 | 49 | mG#mG#mU#mGmAmGmCmUmCmUrUrArUrUrU#rG#rCrGrU#mAmGrU#rU#rU#mUmAmGmAmGmCmUmAmU#mG#mC#mU | 352710 | 12012.5/12013.2 |
| C10 | 50 | mG#mG#mU#mGmAmGmCmUmCmUfUfAfUfUrU#rG#fCfGrU#mAmGrU#rU#rU#mUmAmGmAmGmCmUmAmU#mG#mC#mU | 352710 | 12024.5/12025.1 |
| C11 | 51 | mG#mG#mU#mGmAmGmCmUmCmUfUfAfUfUrU#rG#rC#rG#rU#mAmGrU#rU#rU#mUmAmGmAmGmCmUmAmU#mG#mC#mU | 352710 | 12052.4/12053.3 |
| C12 | 64 | Cy3-mG#mG#mU#mGmAmGmCmUmCmUfUfAfUfUrU#rG#fCfGrU#mAmGrU#rU#rU#mUmAmGmAmGmCmUmAmU#mG#mC#mU | 357610 | 12654.8/12655.5 |
| C13 | 65 | Cy3-mG#mG#mU#mGmAmGmCmUmCmUfUfAfUfUrU#rG#rC#rG#rU#mAmGrU#rU#rU#mUmAmGmAmGmCmUmAmU#mG#mC#mU | 357610 | 12682.8/12683.6 |
| C14 | 66 | Cy3-mG#mG#mU#mGmAmGmCmUmCmUfUfAfUfUrU#rG#fCfGrU#mAmGrU#rU#rU#mUmAmGmAmGmCmUmAmU#mG#mC#mU-TegChol | 399190 | 14488.5/14489.3 |
| C15 | 67 | Cy3-mG#mG#mU#mGmAmGmCmUmCmUfUfAfUfUrU#rG#rC#rG#rU#mAmGrU#rU#rU#mUmAmGmAmGmCmUmAmU#mG#mC#mU-TegChol | 399190 | 14516.4/14517.5 |
| C16 | 68 | Cy3-mG#mG#mU#mGmAmGmCmUmCmUfUfAfUfUrU#rG#fCfGrU#mAmGrU#rU#rU#mUmAmGmAmGmCmUmAmU#mG#mC#mU-GalNAc | 399190 | 15522.2/15520.2 |
| C17 | 52 | mG#mG#mU#mGmAmGmCmUmCmUfUfAfUfUrU#rG#fCfGrU#mAmGrU#rU#rU#mUrA#mGmAmGmCmUmAmU#mG#mC#mU | 352710 | 12027.4/12027.2 |
| C18 | 53 | mG#mG#mU#mGmAmGmCmUmCmUfUfAfUfUrU#rG#fCfGrU#mAmGrU#rU#rU#mAmGmAmGmCmUmAmU#mG#mC#mU | 352710 | 12026.4/12027.2 |
| C19 | 54 | mG#mG#mU#mGmAmGmCmUmCmUfUfAfUfUrU#rG#fCfGrU#mAmGrU#rU#rU#rA#mGmAmGmCmUmAmU#mG#mC#mU | 352710 | 12029.4/12029.2 |
| C20 | 55 | mG#mG#mU#mGmAmGmCmUmCmUfUfAfUfUrU#rG#fCfGrU#mAmGrU#rU#fUfAmGmAmGmCmUmAmU#mG#mC#mU | 352710 | 12000.4/12001.1 |
| C21 | 56 | mG#mG#mU#mGmAmGmCmUmCmUfUfAfUfUfUfGfCfGfUmAmGfUfUfUfUfAmGmAmGmCmUmAmU#mG#mC#mU | 352710 | 11916.6/11916.6 |
| C22 | 57 | mG#mG#mU#mGmAmGmCmUmCmUfUfAfUfUrU#rG#fCfGrU#mAmGfUrU#fUfUfAmGmAmGmCmUmAmU#mG#mC#mU | 352710 | 11972.5/11972.9 |
| hiGC C1 | 60 | mG#mG#mU#mGmAmGmCmUmCmUfUfAfUfUrU#rG#fCfGrU#mAmGrU#rU#rU#fUfAmGmAmGmCmGmAmG#mC#mG#mC | 353160 | 12077.5/12078.1 |

TABLE 5-continued

Heavily and fully chemically modified crRNAs and tracrRNAs.

| Name | SEQ ID NO: | Sequence | Extinction Coefficient | MW (Observed/ Calculated) |
|---|---|---|---|---|
| hiGC C2 | 61 | mG#mG#mU#mGmAmGmCmUmCmUfUfAfUfUrU#rG#fCfGrU#mAmGrU#rU#rU#fUfAmGmAfGfCfGfAfG#fC#mG#mC | 353160 | 12005.4/12005.9 |
| hiGC C3 | 62 | mG#mG#mU#mGmAmGmCmUmCmUfUfAfUfUrU#rG#fCfGrU#mAmGrU#rU#rU#fUfAmGmAfGmCfGmAfG#mC#mG#mC | 353160 | 12041.4/12042 |
| hiGC C4 | 63 | mG#mG#mU#mGmAmGmCmUmCmUfUfAfUfUrU#rG#fCfGrU#mAfGrU#rU#rU#fUfAmGmAfGmCfGmAfG#mC#mG#mC | 353160 | 12029.4/12030 |
| T1 | 58 | mA#mG#mC#mAmUmAmGrCrArArGrUrUmArArArArUrArArGmGrCrUmArGrUrCmCrGrUrUrArUrCrAmAmCmUmUmGmAmAmAmAmAmGmUrGrGrCrAmCmCmGrArGrUrCrGmGmUmGmC#mU#mU#mU | 699750 | 22130.8/22130.2 |
| T2 | 13 | mA#mG#mC#mAmUmAmGmCmAmAmGrUrUmArAmAmArUmAmAmGmGrCrUmArGrUrCmCrGrUrUmAmUmCmAmAmCmUmUmGmAmAmAmAmAmGmUmGmGmCmAmCmCmGmAmGmUmCmGmGmUmGmC#mU#mU#mU | 699750 | 22439.6/22438.8 |
| T3 | 14 | mA#mG#mC#mAmUmAmGmCmAmAmGrU#rU#mArA#mAmArU#mAmAmGmGrC#rU#mArG#rU#rC#mCrG#rU#rU#mAmUmCmAmAmCmUmUmGmAmAmAmAmAmGmUmGmGmCmAmCmCmGmAmGmUmCmGmGmUmGmC#mU#mU#mU | 699750 | 22632.5/22631.6 |
| T4 | 15 | mA#mG#mC#mAmUmAmGmCmAmAmGrUrUmAmAmAmArUmAmAmGmGrCrUmArGrUrCmCrGrUrUmAmUmCmAmAmCmUmUmGmAmAmAmAmAmGmUmGmGmCmAmCmCmGmAmGmUmCmGmGmUmGmC#mU#mU#mU | 699750 | 22453.6/22452.8 |
| T5 | 59 | mA#mG#mC#mAmUmAmGmCmAmAmGrUrUmAmAmAmArUmAmAmGmGrCrUmArGrUrCmCrGrUrUmAmUmCmAmAmCmUmUmGmAmAmAmAmAmGmUmGmGmCmAmCmCmGmAmGmUmCmGmGmUmGmC#mU#mU#mU-TegChol | 741330 | 24287.4/24286.7 |
| T6 | 16 | mA#mG#mC#mAmUmAmGmCmAmAmGrUrUmArAmAmAfUmAmAmGmGfCfUmArGfUfCmCrGrUrUmAmUmCmAmAmCmUmUmGmAmAmAmAmAmGmUmGmGmCmAmCmCmGmAmGmUmCmGmGmUmGmC#mU#mU#mU | 699750 | 22449.2/22448.7 |
| T7 | 17 | mA#mG#mC#mAmUmAmGmCmAmAmGrUfUmArAmAmAfUmAmAmGmGfCfUmAfGfUfCmCrGrUrUmAmUmCmAmAmCmUmUmGmAmAmAmAmAmGmUmGmGmCmAmCmCmGmAmGmUmCmGmGmUmGmC#mU#mU#mU | 699750 | 22453.1/22452.7 |
| T8 | 18 | mA#mG#mC#mAmUmAmGmCmAmAmGfUfUmAfAmAmAfUmAmAmGmGfCfUmAfGfUfCmCfGfUfUmAmUmCmAmAmCmUmUmGmAmAmAmAmAmGmUmGmGmCmAmCmCmGmAmGmUmCmGmGmUmGmC#mU#mU#mU | 699750 | 22463.3/22462.7 |
| hiGC T1 | 37 | mG#mC#mG#mCmUmCmGmCmAmAmGrUrUmArAmAmArUmAmAmGmGrCrUmArGrUrCmCrGrUrUmAmUmCmAmAmCmUmUmGmAmAmAmAmAmGmUmGmGmCmAmCmCmGmAmGmUmCmGmGmUmGmC#mU#mU#mU | 681480 | 22407.4/22406.7 |
| hiGC T2 | 38 | mG#mC#fG#fCfUfCfGfCmAmAmGrUrUmArAmAmArUmAmAmGmGrCrUmArGrUrCmCrGrUrUmAmUmCmAmAmCmUmUmGmAmAmAmAmAmGmUmGmGmCmAmCmCmGmAmGmUmCmGmGmUmGmC#mU#mU#mU | 681480 | 22335/22334.5 |
| hiGC T3 | 39 | mG#mC#fG#mCfUmCfGmCmAmAmGrUrUmArAmAmArUmAmAmGmGrCrUmArGrUrCmCrGrUrUmAmUmCmAmAmCmUmUmGmAmAmAmAmAmGmUmGmGmCmAmCmCmGmAmGmUmCmGmGmUmGmC#mU#mU#mU | 681480 | 22371.3/22370.6 |

TABLE 5-continued

Heavily and fully chemically modified crRNAs and tracrRNAs.

| Name | SEQ ID NO: | Sequence | Extinction Coefficient | MW (Observed/ Calculated) |
|---|---|---|---|---|
| hiGC T4 | 40 | mG#mC#fG#mCfUmCfGmCmAmAmGrUrUfArAfAfArUmAmAmGmGrCrUmArGrUrCmCrGrUrUmAmUmCmAmAmCmUmUmGmAmAmAmAmAmGmUmGmGmCmAmCmCmGmAmGmUmCmGmGmUmGmC#mU#mU#mU | 681480 | 22335/22334.5 |
| HTT-C10 | 117 | mU#mG#mA#mAmGmUmGmCmAmCfAfCfAfGrU#rA#fGfArU#mGmGrU#rU#rU#mUmAmGmAmGmCmUmAmU#mG#mC#mU | 372510 | 12092.5/12093.2 |
| HTT-hiGC 1 | 118 | mU#mG#mA#mAmGmUmGmCmAmCfAfCfAfGrU#rA#fGfArU#mGmGrU#rU#rU#fUfAmGmAmGmCmGmAmG#mC#mG#mC | 372960 | 12121.5/12122.2 |
| HTT C0 | 119 | rU#rG#rA#rArGrUrGrCrArCrArCrArGrUrArGrArUrGrGrUrUrUrArGrArGrCrUrArU#rG#rC#rU | 372510 | 11679.3/11672.3 |
| C0 | 120 | rG#rG#rU#rGrArGrCrUrCrUrUrArUrUrUrGrCrGrUrArGrUrUrUrUrArGrArGrCrUrArU#rG#rCrU | 352710 | 11563.3/11564.1 |
| T0 | | Edit-R tracrRNA (Dharmacon) | — | — |

KEY: rN = RNA, mN = 2'-O-methyl RNA, fN = 2'-fluoro RNA N#N = phosphorothioate linkage

TABLE 6

Additional heavily and fully chemically modified crRNAs and tracrRNAs targeting endogenous loci, as depicted in FIGS. 13A-13F.

| Name | SEQ ID NO: | Sequence |
|---|---|---|
| HBB-C0 | 121 | rC#rU#rU#rGrCrCrCrCrArCrArGrGrGrCrArGrUrArArGrUrUrUrUrArGrArGrCrUrArU#rG#rCrU |
| HBB-C20 | 122 | mC#mC#mU#mGmCmCmCmCmAmCfAfGfGfGrC#rA#fGfUrA#mAmGrU#rU#rU#fUfAmGmAmGmCmUmAmU#mG#mC#mU |
| HTT-C20 | 123 | mU#mG#mA#mAmGmUmGmCmAmCfAfCfAfGrU#rA#fGfArU#mGmGrU#rU#rU#fUfAmGmAmGmCmUmAmU#mG#mC#mU |
| HTT-C21 | 124 | mU#mG#mA#mAmGmUmGmCmAmCfAfCfAfGfUfAfGfAfUmGmGfUfUfUfUfAmGmAmGmCmUmAmU#mG#mC#mU |
| VEGFA-C0 | 125 | rG#rG#rU#rGrArGrUrGrArGrUrGrUrGrUrGrCrGrUrGrGrUrUrUrUrArGrArGrCrUrArU#rG#rCrU |
| VEGFA-C20 | 126 | mG#mG#mU#mGmAmGmUmGmAmGfUfGfUfGrU#rG#fCfGrU#mGmGrU#rU#rU#fUfAmGmAmGmCmUmAmU#mG#mC#mU |
| VEGFA-C21 | 127 | mG#mG#mU#mGmAmGmUmGmAmGfUfGfUfGfUfGfCfGfUmGmGfUfUfUfUfAmGmAmGmCmUmAmU#mG#mC#mU |

KEY: rN = RNA, mN = 2'-O-methyl RNA, fN = 2'-fluoro RNA N#N = phosphorothioate linkage Crystal structures of SpyCas9 have been solved as the RNP alone or bound to one or both strands of target DNA (Nishimasu et al. Cell 156:935-949 (2014); Anders al. Nature 513:569 (2014); Jiang et al. Science 351:867-871 (2016); Jiang et al, Science 348:1477-1481 (2015)). These structures provide detailed information regarding the interactions between the Cas9 protein and the crRNA:tracrRNA complex. These structures were used to identify sites where Cas9 protein makes no contacts with the crRNA or tracrRNA.

Chemically Modified crRNA and tracrRNA Screening Methods

Cell Culture

Screening was performed in a HEK293T stable cell line expressing the traffic light reporter (TLR) system. The HEK293T cells were cultured in Dulbecco-modified Eagle's Minimum Essential Medium (DMEM; Life Technologies). DMEM was also supplemented with 10% Fetal Bovine Serum (FBS; Sigma). Cells were grown in a humidified 37° C., 5% $CO_2$ incubator.

Expression and Purification of Spy-Cas9

The pMCSG7 vector expressing the Cas9 from *Streptococcus pyogenes* was used. In this construct, the Cas9 also contains three nuclear localization signals (NLSs). Rosetta DE3 strain of *Escherichia coli* was transformed with the 3×NLS-SpyCas9 construct. For expression and purification of 3×NLS-SpyCas9, a previously described protocol was used (Jinek et al. Science, 337:816 (2012)). The bacterial culture was grown at 37° C. until an OD600 of 0.6 was reached. Then, the bacterial culture was cooled to 18° C., and 1 mM Isopropyl β-D-1-thiogalactopyranoside (IPTG; Sigma) was added to induce protein expression. Cells were grown overnight for 16-20 hours.

The bacterial cells were harvested and resuspended in Lysis Buffer [50 mM Tris-HCl (pH 8.0), 5 mM imidazole]. 10 μg/mL of Lysozyme (Sigma) was then added to the mixture and incubated for 30 minutes at 4° C. This was followed by the addition of 1×HALT Protease Inhibitor Cocktail (ThermoFisher). The bacterial cells were then sonicated and centrifuged for 30 minutes at 18,000 rpm. The supernatant was then subjected to Nickel affinity chromatography. The elution fractions containing the SpyCas9 were then further purified using cation exchange chromatography using a 5 mL HiTrap S HP column (GE). This was followed by a final round of purification by size-exclusion chromatography using a Superdex-200 column (GE). The purified protein was concentrated and flash frozen for subsequent use.

Transfection of HEK293T Cells

The HEK293T cells were nucleofected using the Neon transfection system (ThermoFisher) according to the manufacturer's protocol. Briefly, 20 picomoles of 3×NLS-SpyCas9 was mixed with 25 picomoles of crRNA:tracrRNA in buffer R (ThermoFisher) and incubated at room temperature for 20-30 minutes. This Cas9 RNP complex was then mixed with approximately 100,000 cells which were already resuspended in buffer R. This mixture was nucleofected with a 10 μL Neon tip and then plated in 24-well plates containing 500 μL of DMEM and 10% FBS. The cells were stored in a humidified 37° C. and 5% $CO_2$ incubator for 2-3 days.

Flow Cytometry Analysis

The nucleofected HEK293T cells were analyzed on MACSQuant® VYB from Miltenyi Biotec. For mCherry detection, the yellow laser (561 nm) was used for excitation and 615/20 nm filter used to detect emission. At least 20,000 events were recorded and the subsequent analysis was performed using FlowJo® v10.4.1. Cells were first sorted based on forward and side scattering (FSC-A vs SSC-A) to eliminate debris. Cells were then gated using FSC-A and FSC-H to select single cells. Finally, mCherry signal was used to select for mCherry-expressing cells. The percent of cells expressing mCherry was calculated and reported in this application as a measure of Cas9-based genome editing.

Indel Analysis by TIDE

The genomic DNA from HEK293T cells was harvested using DNeasy Blood and Tissue kit (Qiagen) as recommended by the manufacturer. Approximately 50 ng of genomic DNA was used to PCR-amplify a ~700 base pair fragment that was subsequently purified using a QIAquick PCR Purification kit (Qiagen). The PCR fragment was then sequenced by Sanger sequencing and the trace files were subjected to indel analysis using the TIDE web tool (Brinkman et al. Nucleic Acids Research, 42: e168 (2014)). Results are reported as % Indel rate.

In Vitro DNA Cleavage Assays

The traffic light reporter plasmid (Addgene: 31482) was linearized with restriction enzyme EcoRI (N.E.B.) for 1 hour, 37° C. in NEB buffer 3, followed by heat inactivation for 20 minutes at 65° C. For the Cas9 digest, 200 ng of linearized plasmid DNA was added to pre-formed RNP complexes (8 μmol or 0.8 μmol) and incubated for 1 hour at 37° C. in 25 μl NEB buffer 3. Cut DNA was purified using Zymo DNA purification columns and separated on a 1% agarose gel run at 100 V. Relative intensities of full length and Cas9-cut DNA fragments were determined using Image J software.

Serum Stability Assays

A 10 μM Cas9 RNP complex was first assembled in cleavage buffer mM HEPES (pH 7.5), 250 mM KCl and 10 mM $MgCl_2$]. Then 2 μM Cas9 RNP was incubated with 8% FBS in a 50 μL reaction at 37° C. Then at time points of 0 hours, 1 hour and 20 hours, 10 uLs of the reaction mixture was treated with Proteinase K and then 10 L of quench buffer (90% formamide and 25 mM EDTA) was added to the solution. The reaction mixture was resolved on a 10% denaturing polyacrylamide gel containing 6 M Urea. The gel was stained with SYBR Safe and visualized on Typhoon FLA imager.

Initial Screening

Figure 2A:
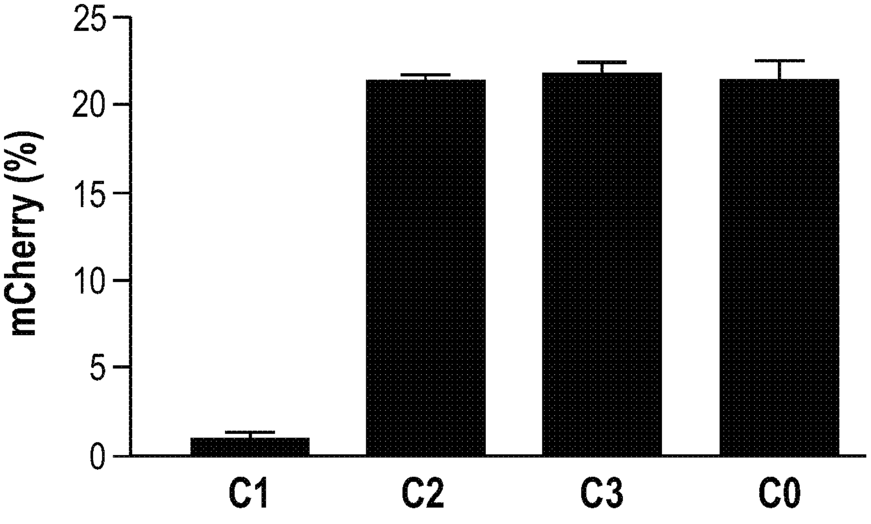
FIG. 2A-FIG. 2B depict genome editing efficiency of several chemically modified crRNAs (C1-C3) used in a HEK293T Traffic Light Reporter (TLR) assay. C0 represents an unmodified crRNA. In vitro-reconstituted RNP complexes of recombinant 3×NLS-SpyCas9, crRNA and tracrRNA were transfected into cells by nucelofection (FIG. 2A) or by lipid-based transfection (FIG. 2B).
Figure 2B:
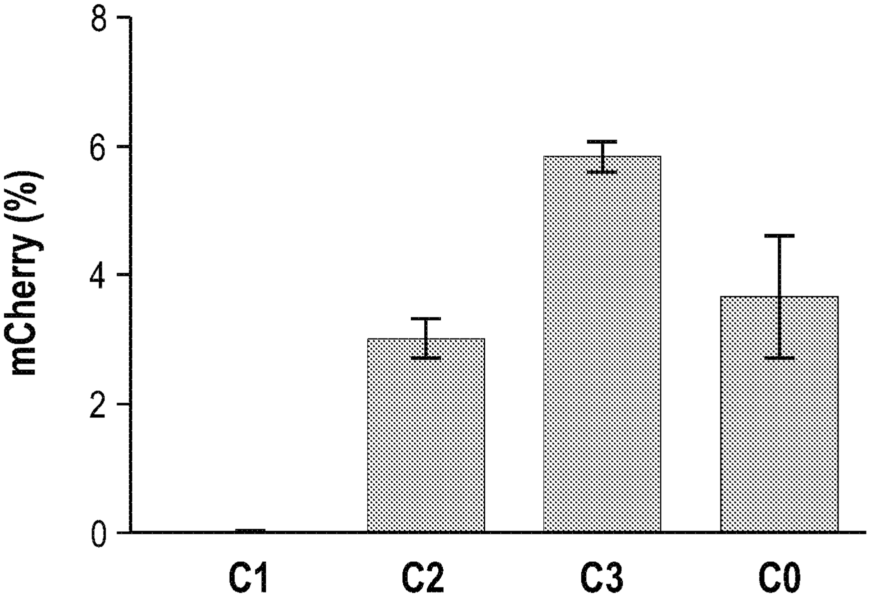

2'-OMe modifications were introduced at guide positions 7-10 and 20 (C2, FIG. 2A and FIG. 2B). Similarly, positions 21 and 27-36 in the crRNA repeat region were also modified using 2'-OMe. To improve nuclease stability, PS modifications were also introduced at the 5' end of the crRNA, yielding the C3 design (FIG. 2A and FIG. 2B and Table 5). In parallel, a crRNA was tested that was more aggressively modified to leave only nine nucleotides (nt) unprotected (C1). Similarly, 2'-OMe modifications were also introduced into the tracrRNA at all positions where no protein contact with the RNA is observed. This gave rise to T1 that is 50% chemically modified (FIG. 3B and Table 5).

Chemically modified crRNAs C2 and C3 retain complete activity relative to the unmodified crRNA C0, suggesting that the modifications introduced in crRNAs C2 and C3 are well tolerated by Cas9 (FIG. 2A). Lipid-based delivery of Cas9 RNP complex showed that C3 was even more efficacious than C0 and C2 (FIG. 2B), which demonstrates the importance of PS linkages at the 5' terminus of the crRNA. Similarly, T1 did not hinder Cas9 activity. On the other hand, the extra modifications introduced in C1 almost completely abolished Cas9 activity in cells. It was reasoned that the 2'-OMe modifications (especially at positions 16-18 in the crRNA) are most likely to compromise Cas9 RNP activity since the nucleotide at position 16 and 18 were shown to make base-specific contacts with Arg447 and Arg71 (Nishimasu, supra). The 2'-OH of the nucleotide at position 16 in the TLR crRNA is also predicted to make a hydrogen bond with Arg447. C3 and T1 were chosen as a basis for further optimization.

Screening of Further Optimized crRNAs

Figure 3A:
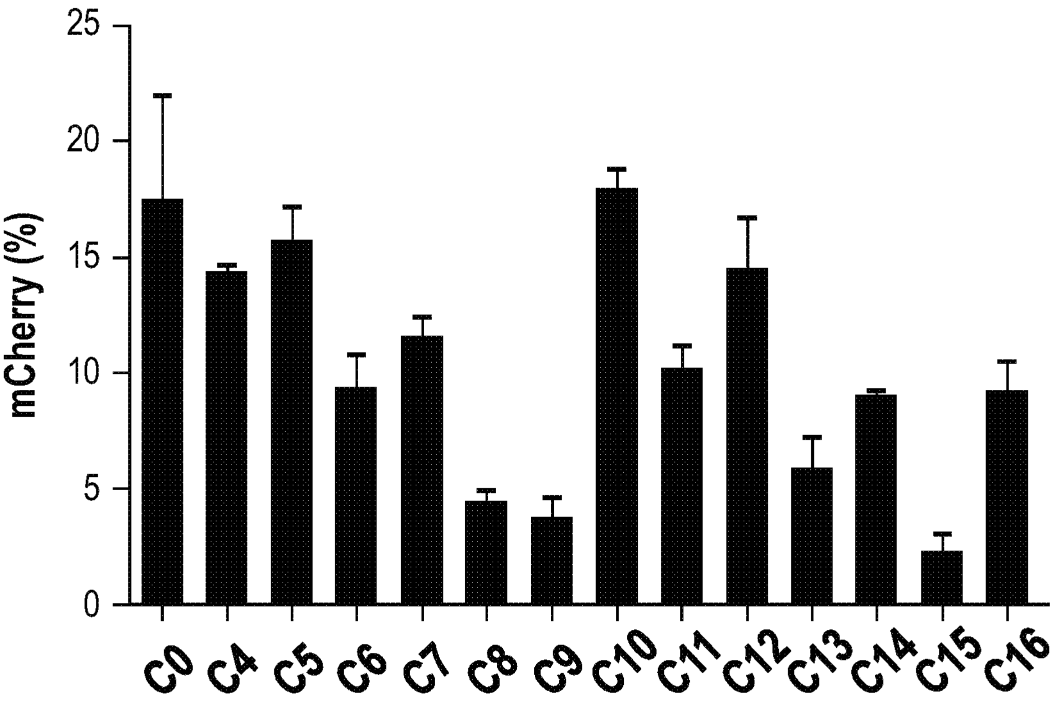
FIG. 3A-FIG. 3B depict genome editing efficiency of several additional chemically modified crRNAs (C4-C16) (FIG. 3A) and several chemically modified tracrRNAs (T1-T5) (FIG. 3B) used in a HEK293T TLR assay. C0 and T0 represent an unmodified crRNA and an unmodified tracrRNA, respectively.
Figure 3B:
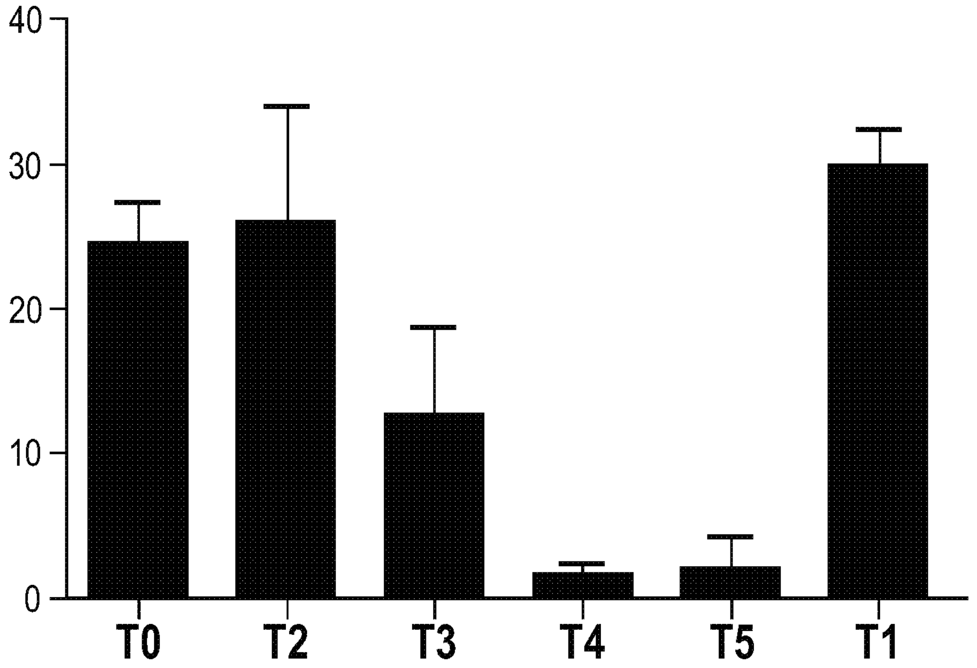

2'-OMe modifications were introduced into the first 6 nucleotides of C3 to yield C4 (FIG. 3A). In another design, 2'-OMe modifications were incorporated at positions 17 and 18 (C5). The nucleotide at position 16 was left unmodified because it makes base- and backbone-specific contacts with Cas9 and likely contributed to the low efficacy of C1. In C6, the importance of 2'—OH groups at positions 25 and 26 was tested. The 2'-OH of these nucleotides contacts the protein in the crystal structure; however, they do not pair with the target DNA, and 2'-OMe substitution at these positions may therefore be more tolerable. C7 and C8 were identical to C5 and C6, respectively, except that they also contained 2'-OMe modifications in the first six positions. All of these crRNAs (C4-C8) were designed to identify modifications responsible for the lower activity of C1 relative to C3.

Figure 4:
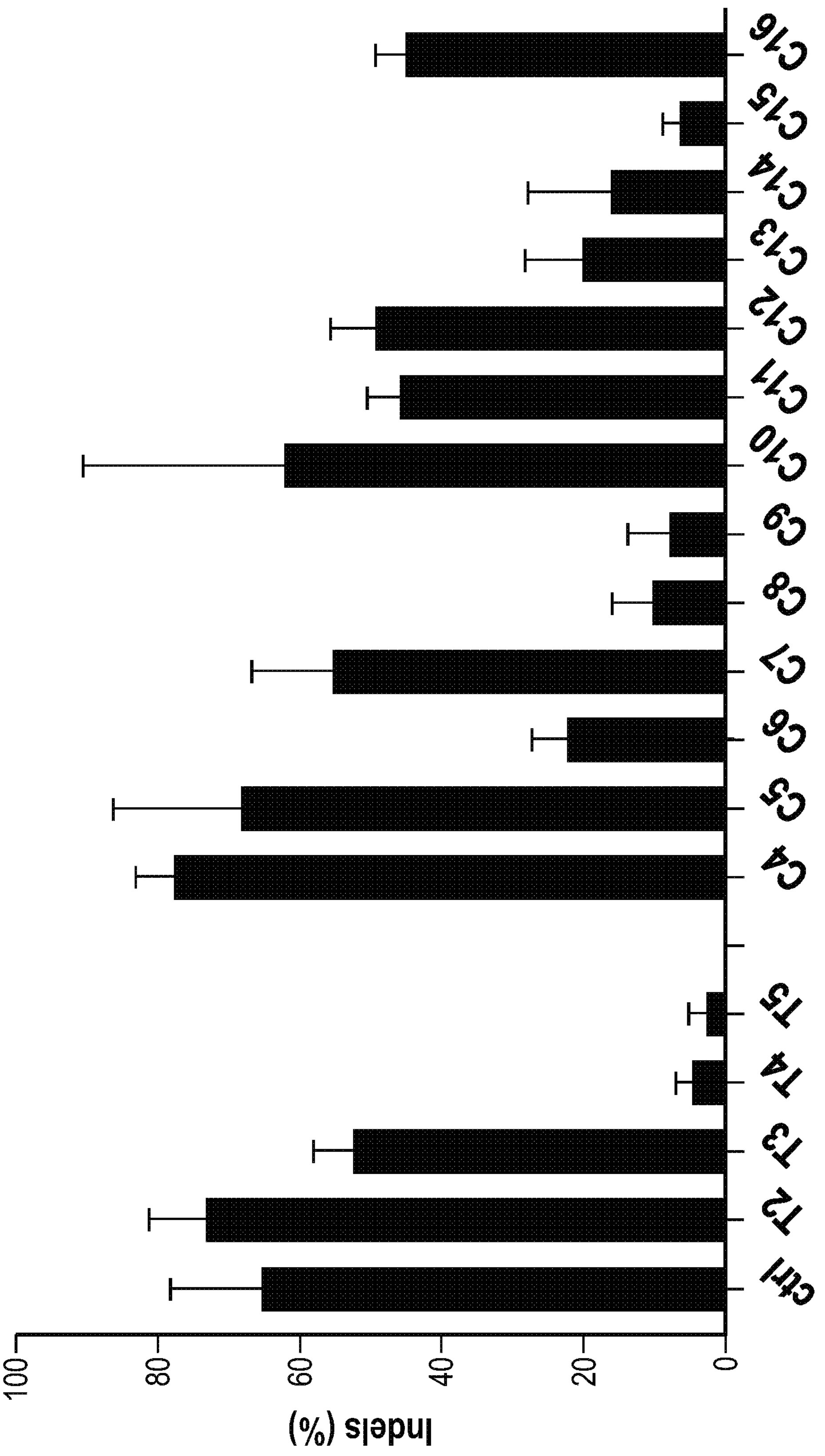
FIG. 4 depicts % indel rate in HEK293T TLR cells with several chemically modified crRNAs (C4-C16) and several chemically modified tracrRNAs (T2-T5). % indel rate was determined using TIDE analysis. The ctrl refers to an unmodified crRNA:tracrRNA pair.
Figure 5:
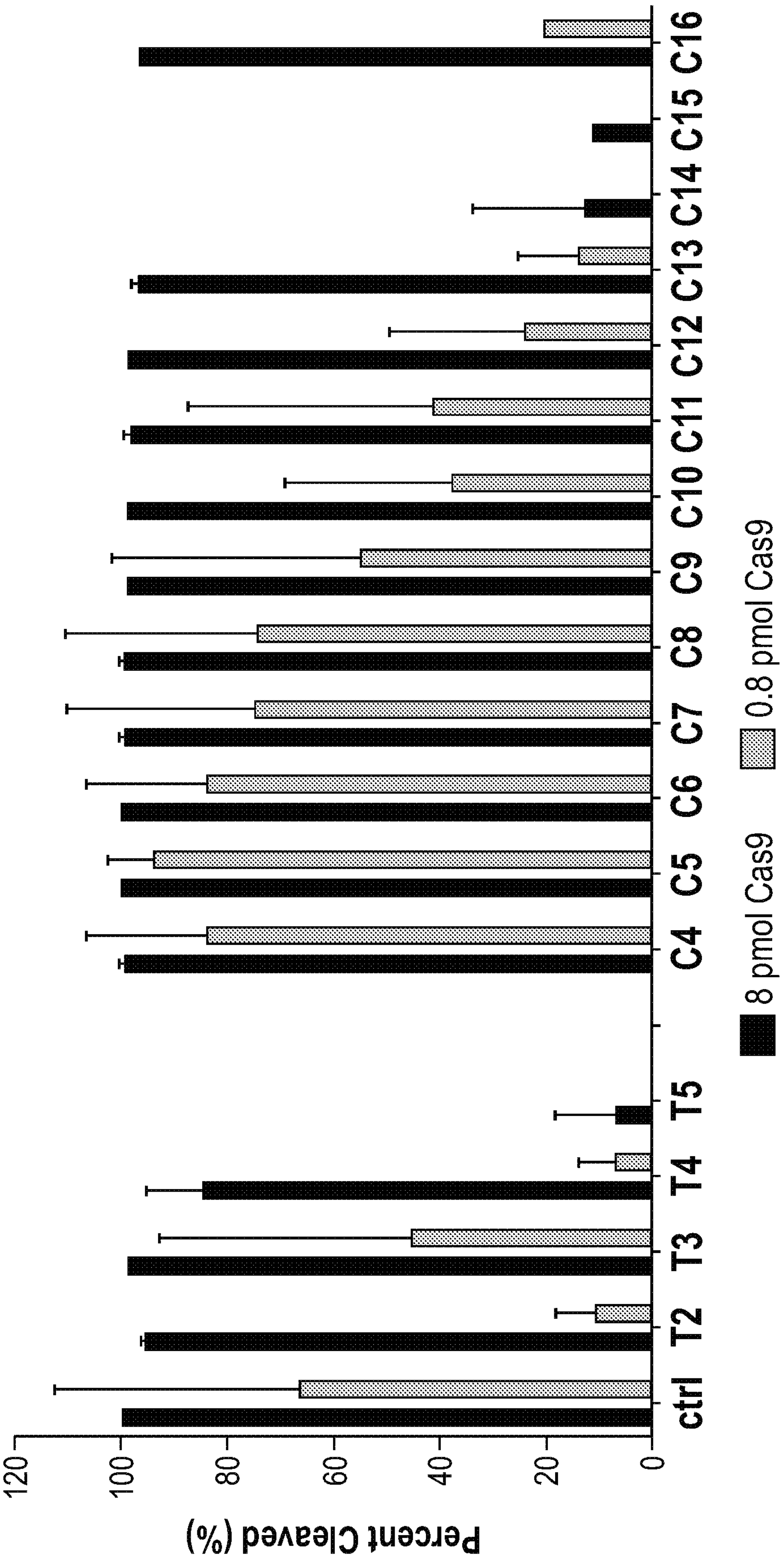
FIG. 5 depicts an in vitro DNA cleavage assay with several chemically modified crRNAs (C4-C16) and several chemically modified tracrRNAs (T2-T5). DNA cleavage assays were performed using saturating (8 pmols) and sub-saturating (0.8 pmols) amounts of Cas9 RNP complex. The ctrl refers to an unmodified crRNA:tracrRNA pair.

C4-C7 retain almost the same efficacy as C0, but C8 activity was strongly reduced. These results indicated that nucleotides at positions 1-6 and 17-18 tolerate 2'-OH substitutions. 2'-OMe modifications at positions 25 and 26 were tolerated in C6 but not in C8. A version of C8 that contained PS linkages at several unprotected positions including 15-16, 19 and 21-23 (C9) was also synthesized. This design also exhibited reduced editing efficiency by Cas9 (FIG. 3A and FIG. 4). When tested for DNA cleavage activity in vitro, C8 and C9 were fully active even at low RNP concentrations (FIG. 5). These results suggest structural perturbations in C8 and C9 that are particularly acute under intracellular conditions.

2'-F-RNAs were also incorporated in this round of optimization since they can increase thermal and nuclease stability of RNA:RNA or RNA:DNA duplexes, and they also interfere minimally with C3'-endo sugar puckering (Patra et al. Angewandte Chemie International Edition 51:11863-11866 (2012); Manoharan et al. Angewandte Chemie International Edition 50:2284-2288 (2011)). 2'-F may be better tolerated than 2'-OMe at positions where the 2'-OH is important for RNA:DNA duplex stability. For these reasons, two crRNAs were synthesized based on C9 but with 2'-F modifications at positions 11-14 and/or 17-18 (C10-C11). These modifications rescued some of C9's diminished activity. In fact, C10 (which contained 2'-F substitutions at positions 11-14 and 17-18) performed better than C11, in which positions 17-18 were unmodified. The results suggest that 2'-F substitutions can compensate for lost efficacy resulting from high 2'-OMe content. It is especially noteworthy that C10 retains the same activity as the unmodified C0 but contains at least one backbone modification at every single phosphodiester linkage. This represents a significant breakthrough for Cas9-based therapeutics because C10 has great potential to provide increased stability, and therefore more efficient editing, in vivo.

Screening of Further Optimized tracrRNAs

T1 was further modified by introducing 2'-OMe substitutions at most positions where the 2'—OH groups do not make crystal contacts with the protein. In addition, some nucleotides that interact with Cas9 were also modified, given that the crRNA tolerated substitutions at many such positions. This approach produced tracrRNAs T2-T5, which contain modifications in at least 55 out of 67 nucleotides. The nucleotide at position 15 (A15) is the only position that differs between T2 and T4 whereas T3 contains additional stabilizing PS linkages at unprotected positions relative to T2. These tracrRNAs were tested in HEK293T-TLR cells, and the majority of 2'-OMe chemical modifications were tolerated by the tracrRNA except at position A15 (FIG. 3B). In the crystal structure, the 2'-OH of A15 interacts with Ser104. The best-performing tracrRNA from this round was T2, which contains 12 unmodified positions. Furthermore, the inclusion of PS linkages at these 12 positions reduced but did not abolish activity. This design (T3) contains at least one chemical modification at every position (either a PS or ribose modification). This also represents an important advance for therapeutic applications of Cas9.

The mCherry signal only results from indels producing a +1 frameshift, and therefore underestimates true editing efficiencies. To ensure that crRNA:tracrRNA combinations do not yield false negatives by favoring TLR indels that are out of the mCherry reading frame, Tracking of Indels by Decomposition (TIDE) analysis was also performed to analyze overall editing efficiencies. As shown in FIG. 4, editing efficiencies measured using TIDE correlate well with the mCherry signal.

Screening of Further Optimized crRNA:TracrRNA Pairs

Chemically modified C10 and T2 were further modified to attempt to define combined crRNA:tracrRNA modification patterns that are compatible with SpyCas9 RNP function. Because crRNA 2'-F substitutions were largely tolerated (FIG. 3A), and in some cases even compensated for the loss of efficacy caused by 2'-OMe substitutions, several 2'-F modifications were added to C10 and T2. In addition, because simultaneous 2'-OMe modification at positions 25 and 26 negatively affected genome editing efficacies in some cases (e.g. C8), the two positions were tested for their sensitivities to 2'-F or individual 2'-OMe substitutions. Additional 2'-F modifications were incorporated in the tracrRNAs. In positions where the nucleobases interact with Cas9, two approaches to modification were taken. While it was suspected that protein-interacting sites would be less tolerant of modification, it was difficult to predict whether steric constraints or charge interactions were more important. To address this issue, three different tracrRNAs were synthesized: one where all protein interacting sites were left as 2'-OH (T6), another where all protein interacting sites were converted to 2'-F (T8), and another where only the nucleobases that interact with nonpolar amino acids were converted to 2'-F (T7). Using this systematic approach, crRNAs C17-C22 and tracrRNAs T6-T8 were synthesized and tested (FIG. 6A-6C).

Figure 6A:
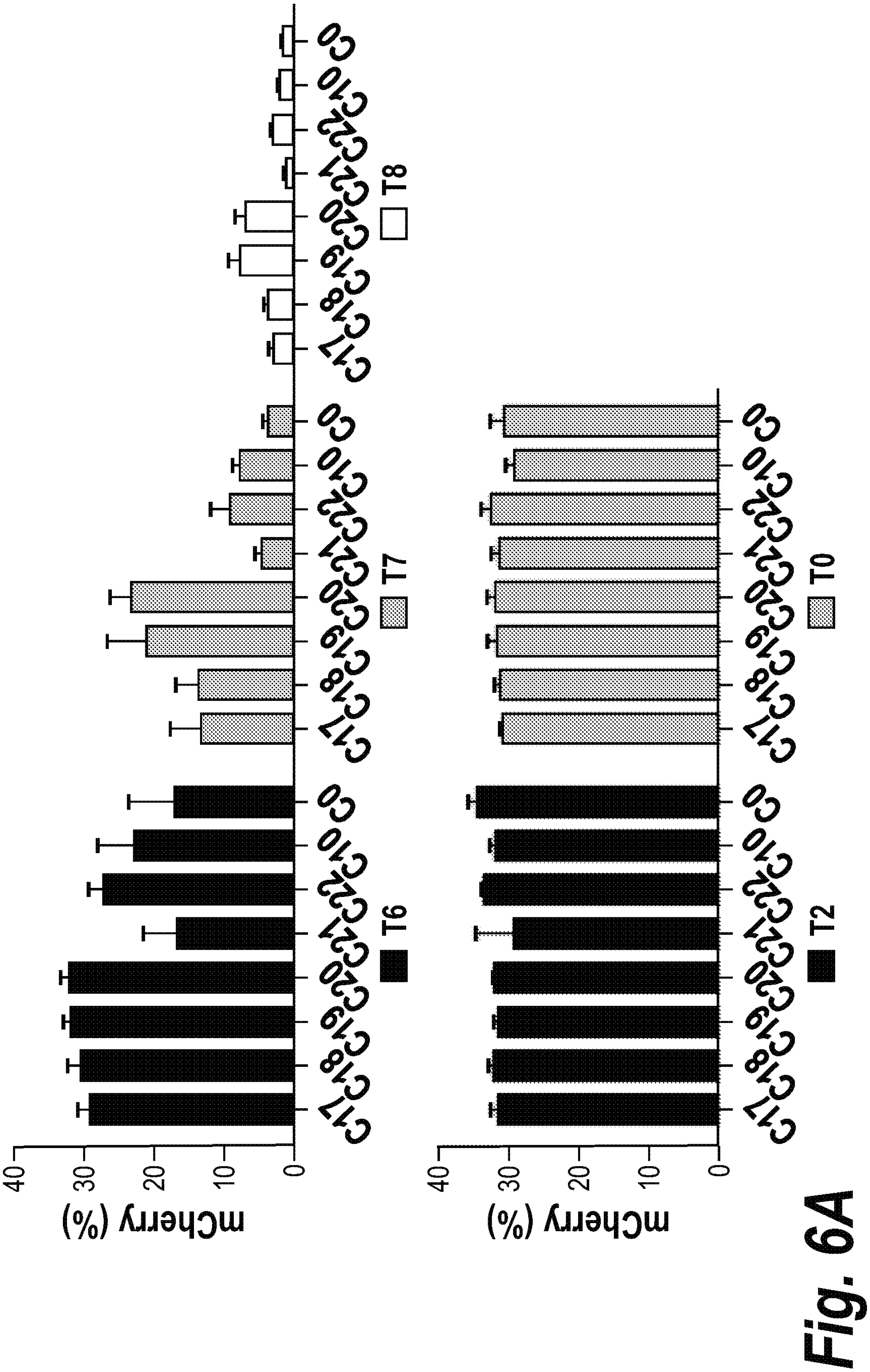
FIG. 6A-FIG. 6C depict several additional chemically modified crRNAs (C10, C17-C22) tested in combination with several chemically modified tracrRNAs (T2, T6-T8) to form chemically modified crRNA:tracrRNA pairs. The various crRNA:tracrRNA pairs were used in a HEK293T TLR assay to determine genome editing efficiency. C0 and T0 represent an unmodified crRNA and an unmodified tracrRNA, respectively. Cells were transfected with 20 μmol (FIG. 6A), 100 μmol (FIG. 6B), and 8 μmol (FIG. 6C) of Cas9, crRNA, tracrRNA RNPs.
Figure 6B:
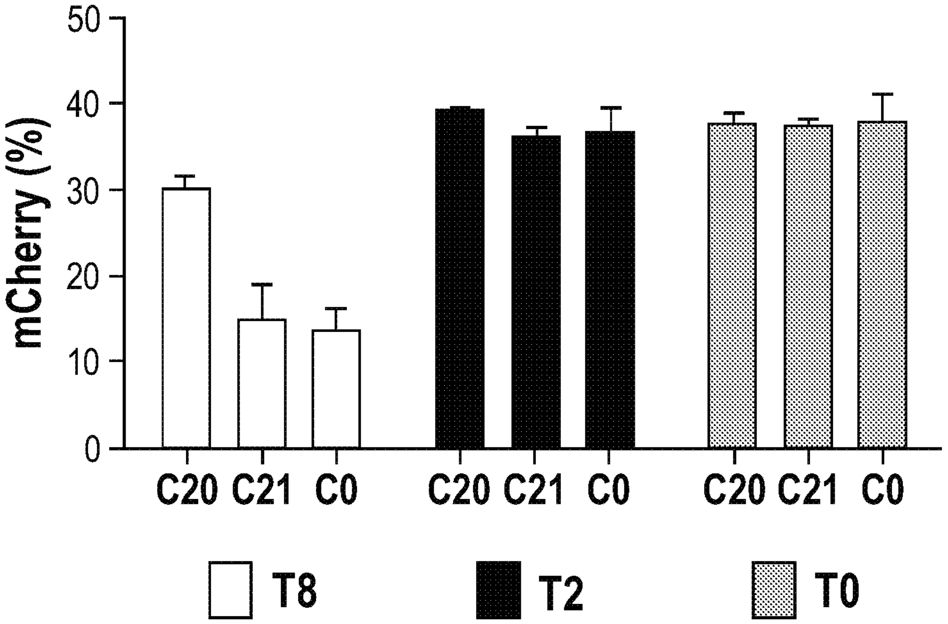
Figure 6C:
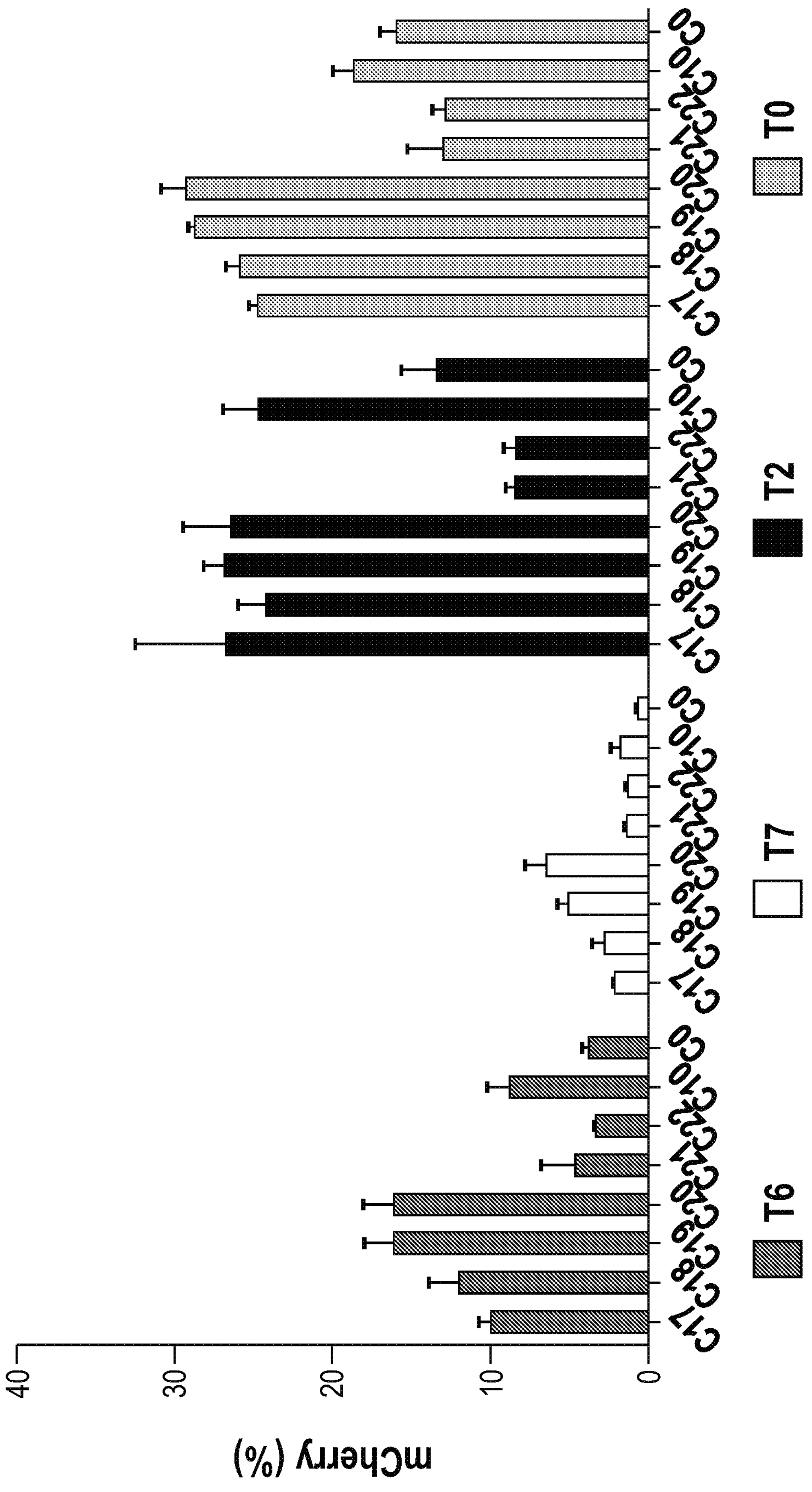

When C17-C22 were used with either T2 or the TO control (20 μmol RNP), all showed comparable efficacy as the C0 and C10 crRNAs (FIG. 6A). This includes the fully modified C21 that is either 2'-F- or 2'-OMe-substituted at every position. This represents the first time a completely modified and fully functional crRNA has been reported. C21 loses some efficacy when combined with T6-T8, and is also less potent than C0 when lower (3 pmole) doses of RNP are delivered (FIG. 6C). These losses may be due to compromised base pairing between the heavily modified repeat: anti-repeat duplexes. Across all tracrRNAs tested, C20 exhibits the highest editing efficiency. In addition, at 3 μmol RNP, C20 is more potent than unmodified C0, suggesting enhanced stability in cells (FIG. 6C). Although C20 includes six ribose sugars, each is adjacent to a PS modification, leaving no unmodified linkages in the crRNA.

Figure 7B:
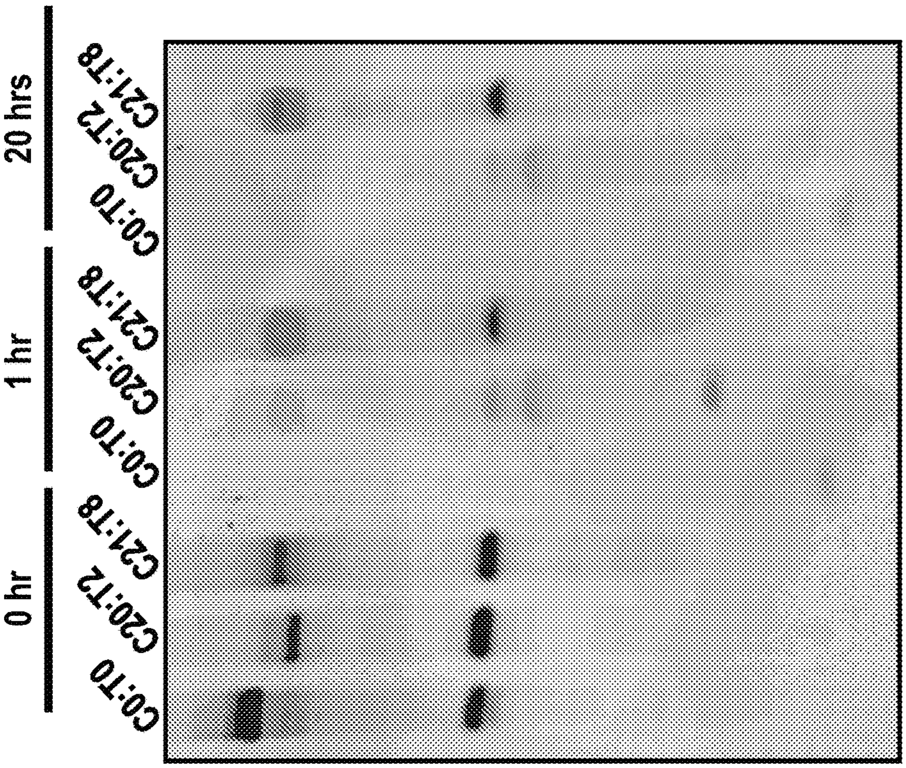
FIG. 7A-FIG. 7B depict serum stability of crRNAs C21, C0, C20 and tracrRNAs TO, T2, T8. The indicated crRNA: tracrRNA combinations were used to make Cas9 RNP complexes that were then incubated with cleavage buffer (FIG. 7A) or 8% FBS (FIG. 7B) for 0, 1 and 20 hours.
Figure 7A:
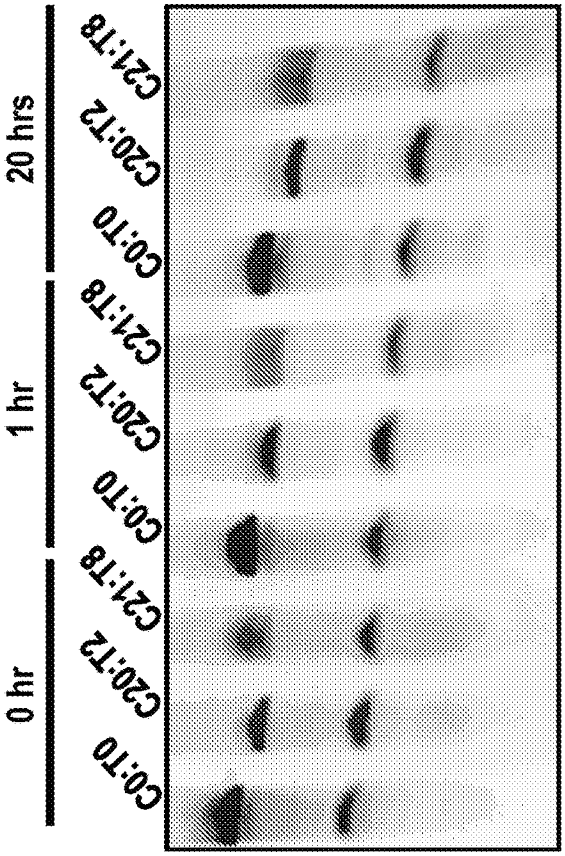

Among T6-T8, the best-performing tracrRNA was T6, especially with modified crRNAs including C20. The fully-modified tracrRNA (T8) compromised the potency of all crRNAs tested, but retains some function (~5% editing with 20 μmol RNP) with C19 and C20 (FIG. 6A). To test whether the T8 activity improves at higher doses, 100 μmol Cas9 RNP was nucleofected into cells. By using a higher amount of Cas9 RNP, the editing efficiency of T8 in combination with C0 or C20 is rescued to the same level as observed using 20 μmol of Cas9 RNP with C0: TO (FIG. 6B). Furthermore, at higher doses, the efficacy of C20:T8 is almost as high as that of C20: TO. Lastly, the editing efficiency of the fully-modified pair (C21:T8) is within about 2-fold of the unmodified (C0: TO) crRNA:tracrRNA pair. This represents the first demonstration of efficient editing activity with a fully modified crRNA:tracrRNA combination. While the editing efficiency is not as high as that of the unmodified RNAs in cells, the increased serum stability afforded by the fully chemically modified C21:T8 combination (FIG. 7A and FIG. 7B) would likely provide significant benefits in vivo, as observed for fully modified siRNAs and ASOs.

Figure 8A:
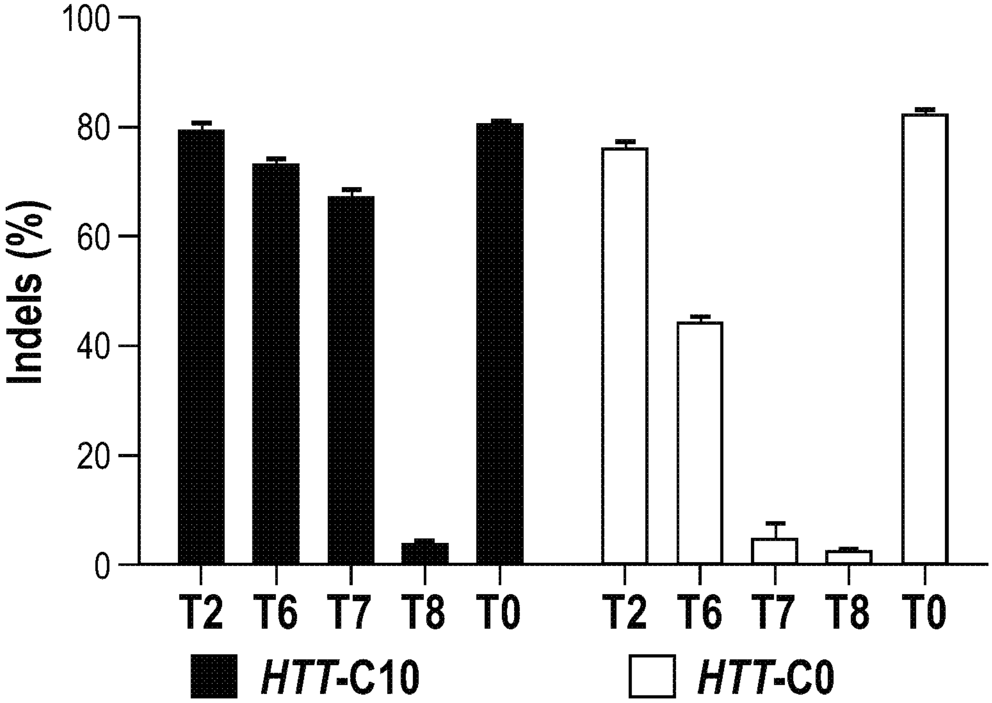
FIG. 8A-FIG. 8B depict targeting of exon 50 of the HTT gene with the C10 chemically modified crRNA paired with T2, and T6-T8 chemically modified tracrRNAs. HEK293T cells were transfected with 20 μmol (FIG. 8A) and 3 μmol (FIG. 8B) of Cas9, crRNA, tracrRNA RNPs.
Figure 8B:
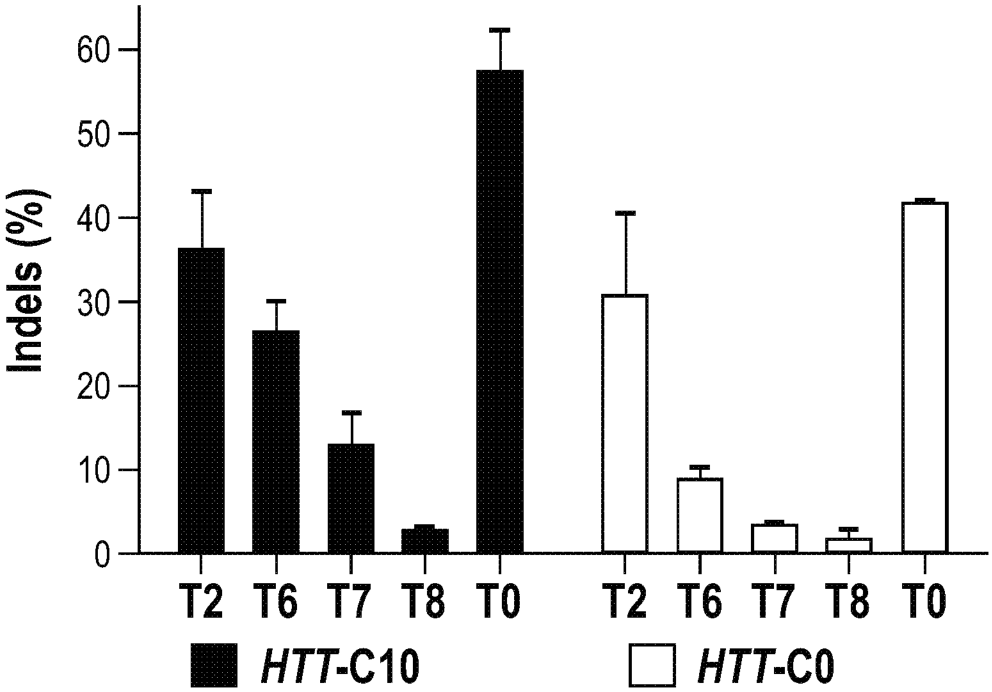

Example 3—Chemically Modified crRNA:TracrRNA Pairs Targeting Endogenous Human Genes To verify that the crRNA designs of the disclosure are compatible with different guide sequences, including those targeting endogenous human genes, the C10 design was tested by targeting exon 50 of the huntingtin (HTT) gene (FIG. 8A and FIG. 8B), a potential polymorphic target for Huntington's disease. The results show that HTT-C10 performs as well as the minimally modified HTT-C0 when paired with T2 and TO. T6 and T7 are more efficacious with the modified C10 compared to unmodified C0. Hence, modifications within both tracrRNA and the crRNA are needed. Furthermore, nucleofections performed using 3 μmol of RNP suggested that C10 may be more efficacious than the unmodified crRNA (FIG. 8B), similar to what was observed in FIG. 6C.

Additional endogenous targets with several different modification patterns were test. Specifically, the genes HBB, HTT, and VEGFA were targeted with the C20 and C21 modification pattern, paired with the T2 and T8 modified tracrRNA (FIG. 13A-FIG. 13F).

These results demonstrate that the modified crRNA and tracrRNA designs are also applicable to endogenous target sites.

Figure 10A:
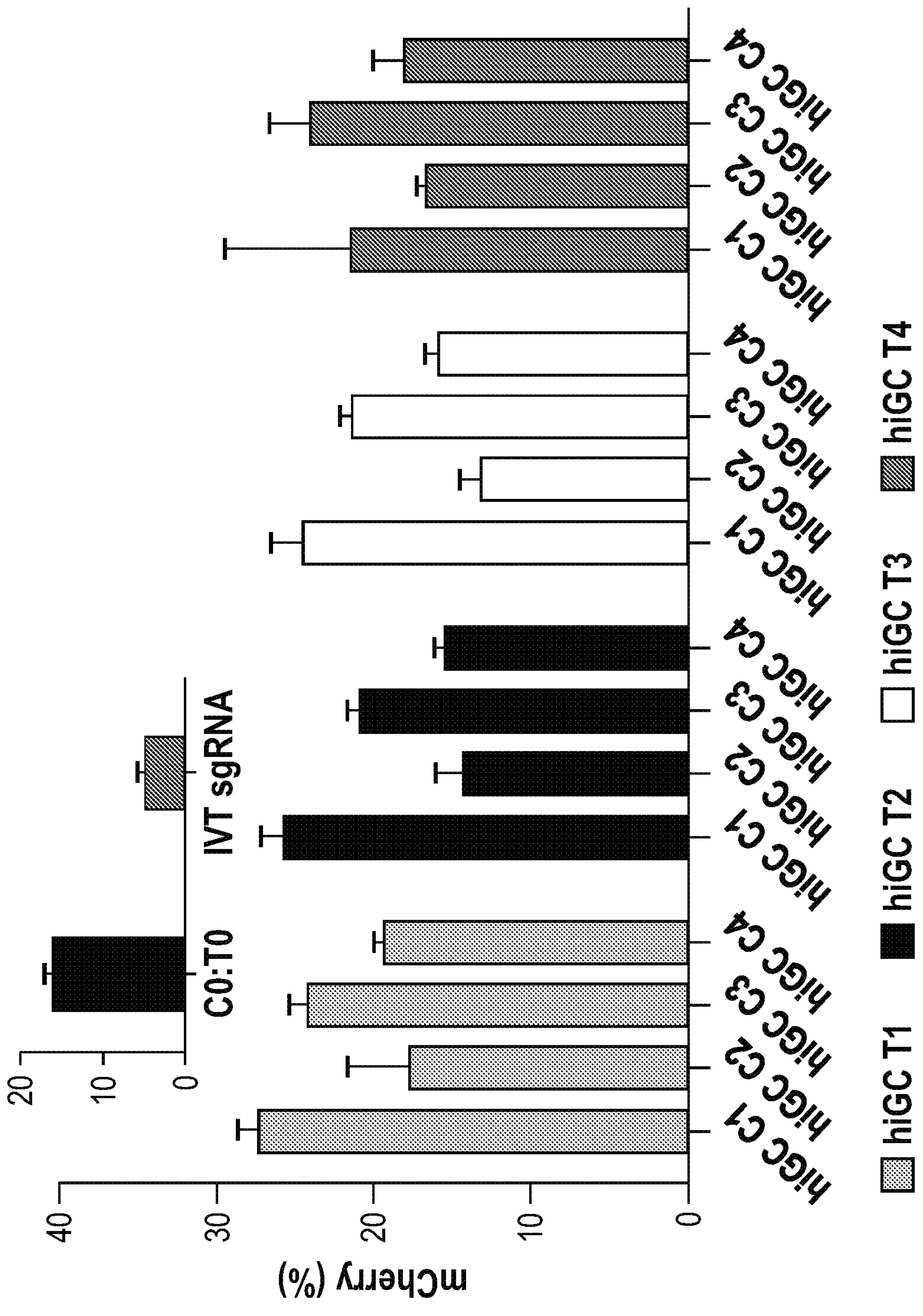
FIG. 10A-FIG. 10B depict various crRNA:tracrRNA pairs with high GC content in the stem region of the crRNA and the anti-stem region of the tracrRNA. The various crRNA:tracrRNA pairs were used in a HEK293T TLR assay to determine genome editing efficiency. Cells were transfected with 3 μmol (FIG. 10A) and 20 μmol (FIG. 10B) of Cas9, crRNA, tracrRNA RNPs.
Figure 10B:
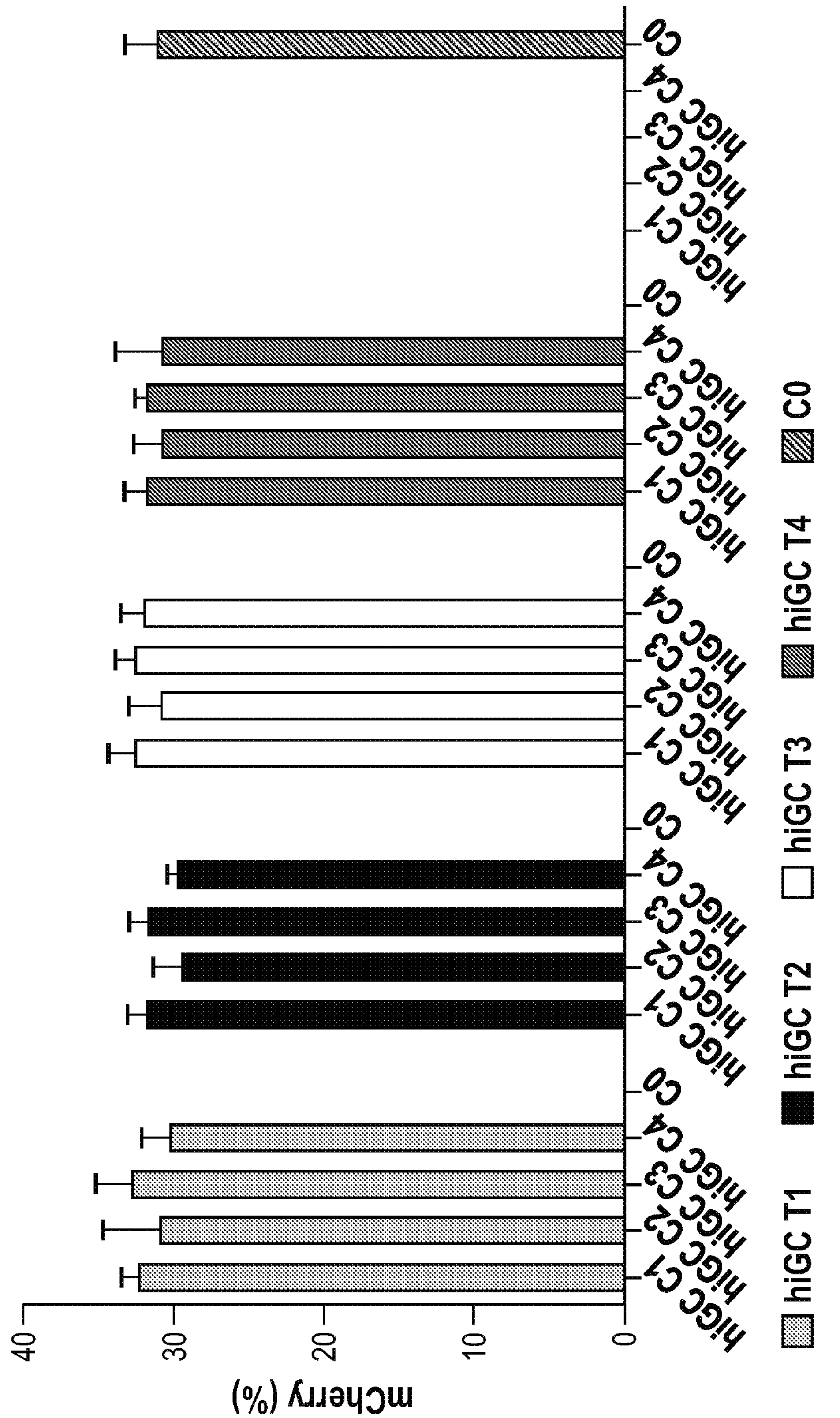
Figure 11:
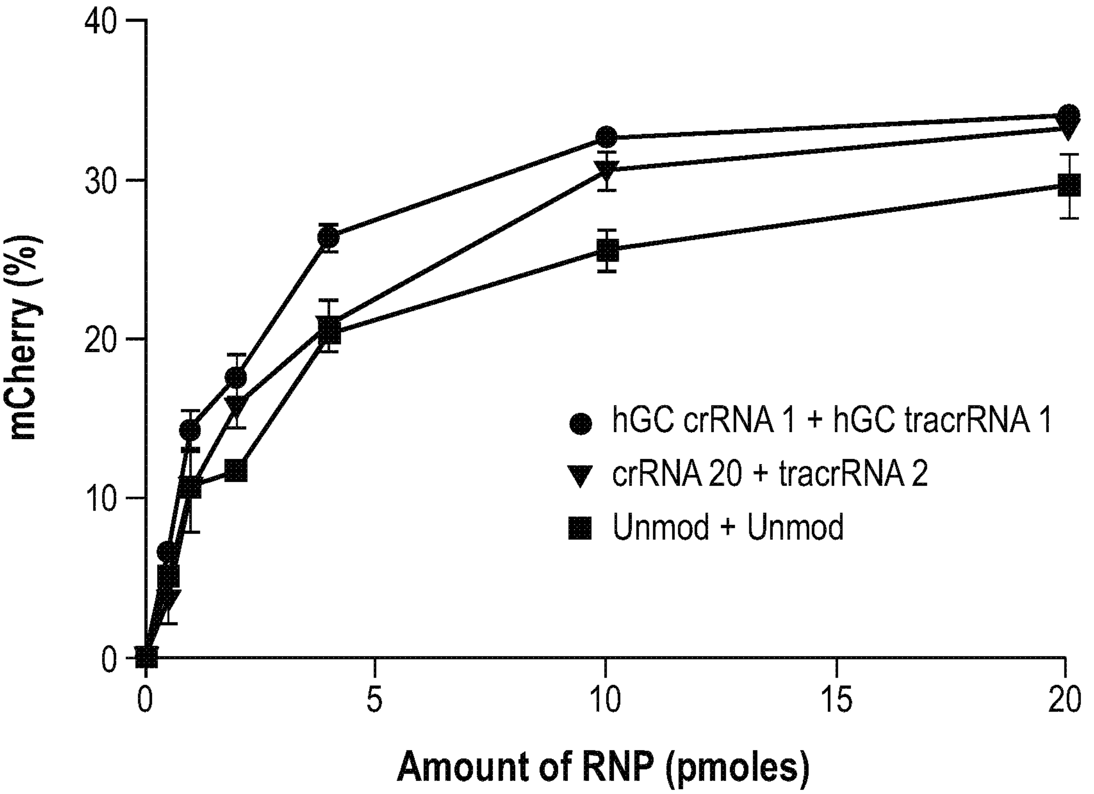
FIG. 11 depicts genome editing efficiency in the HEK293T TLR assay using the hiGC crRNA 1: hiGC tracrRNA 1 pair and the crRNA 20:tracrRNA 2 pair. The two crRNA:tracrRNA pairs were tested at various RNP amounts (in pmol).
Figure 12A:
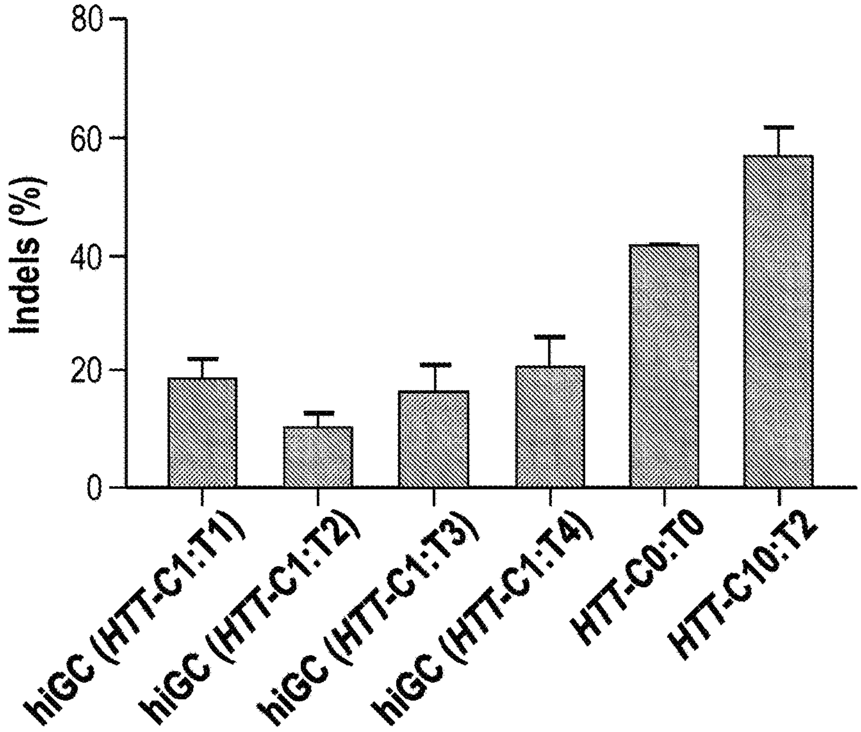
FIG. 12A-FIG. 12B depict targeting of the HTT gene with several crRNA:tracrRNA pairs with high GC content in the stem region of the crRNA and the anti-stem region of the tracrRNA. The % indel frequency in HEK293T cells was measured with the TIDE assay. Cells were transfected with 3 μmol (FIG. 12A) and 20 pmol (FIG. 12B) of Cas9, crRNA, tracrRNA RNPs.
Figure 12B:
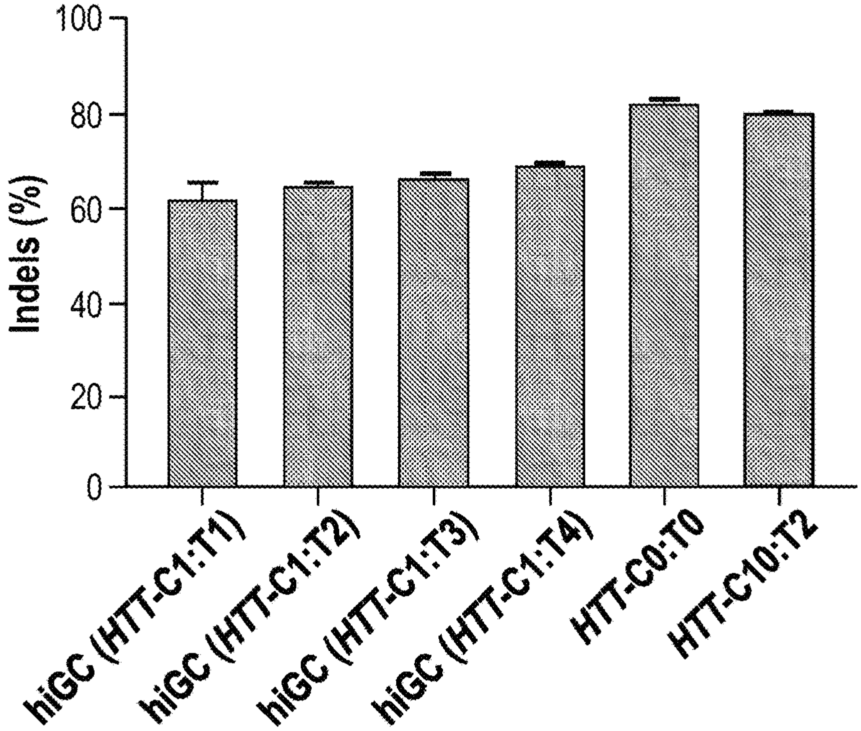
Figures 13A, 13B, 13C, 13D, 13E, 13F:
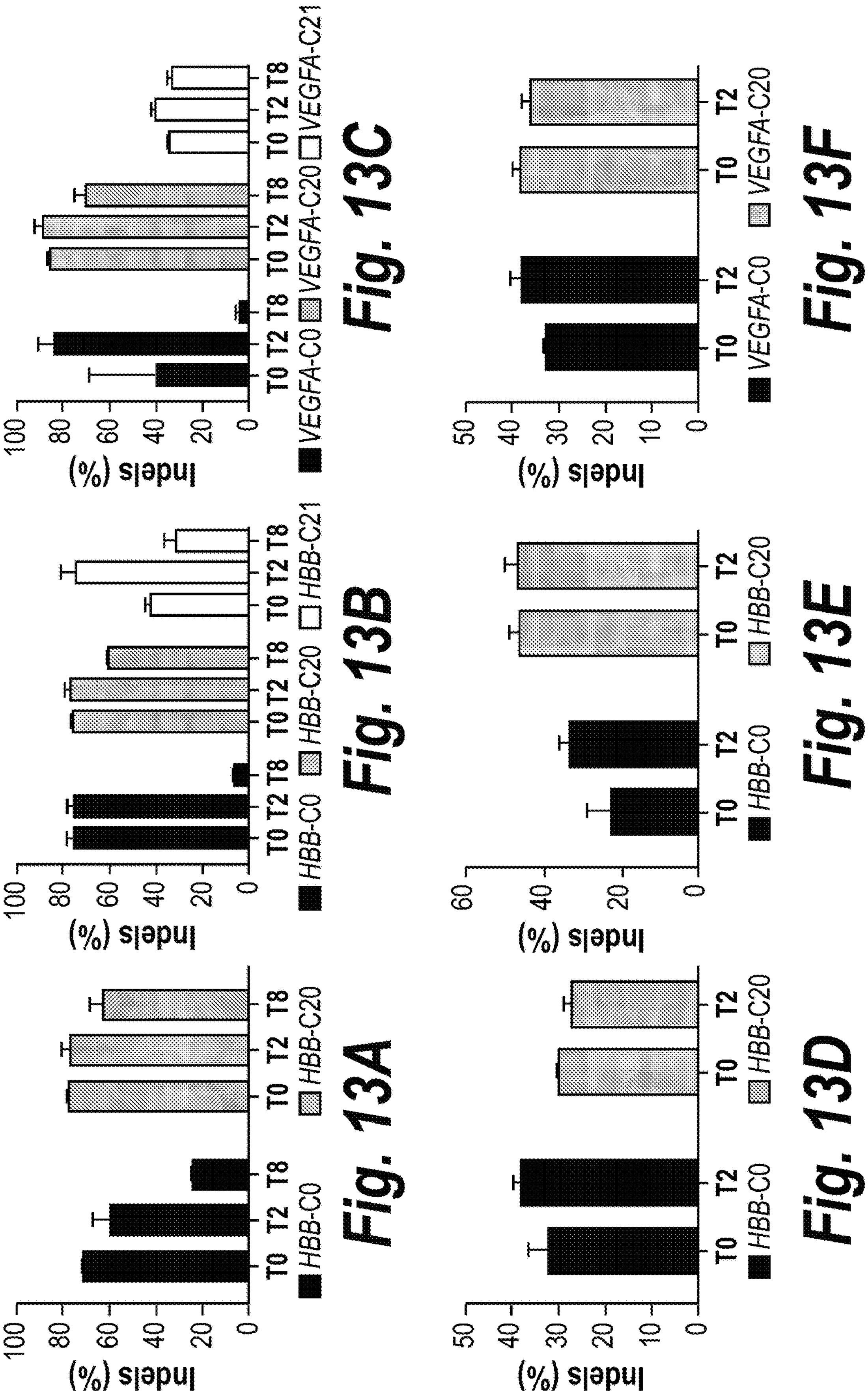
FIG. 13A-FIG. 13F depict targeting of the HBB (FIG. 13A and FIG. 13D), HTT (FIG. 13B and FIG. 13E), and VEGFA (FIG. 13C and FIG. 13F) genes with several crRNA:tracrRNA pairs. The % indel frequency in HEK293T cells was measured with the TIDE assay. Cells were transfected with 80 μmol (FIG. 13A-FIG. 13C) and 3 μmol (FIG. 13D-FIG. 13F) of Cas9, crRNA, tracrRNA RNPs
Figure 14A:
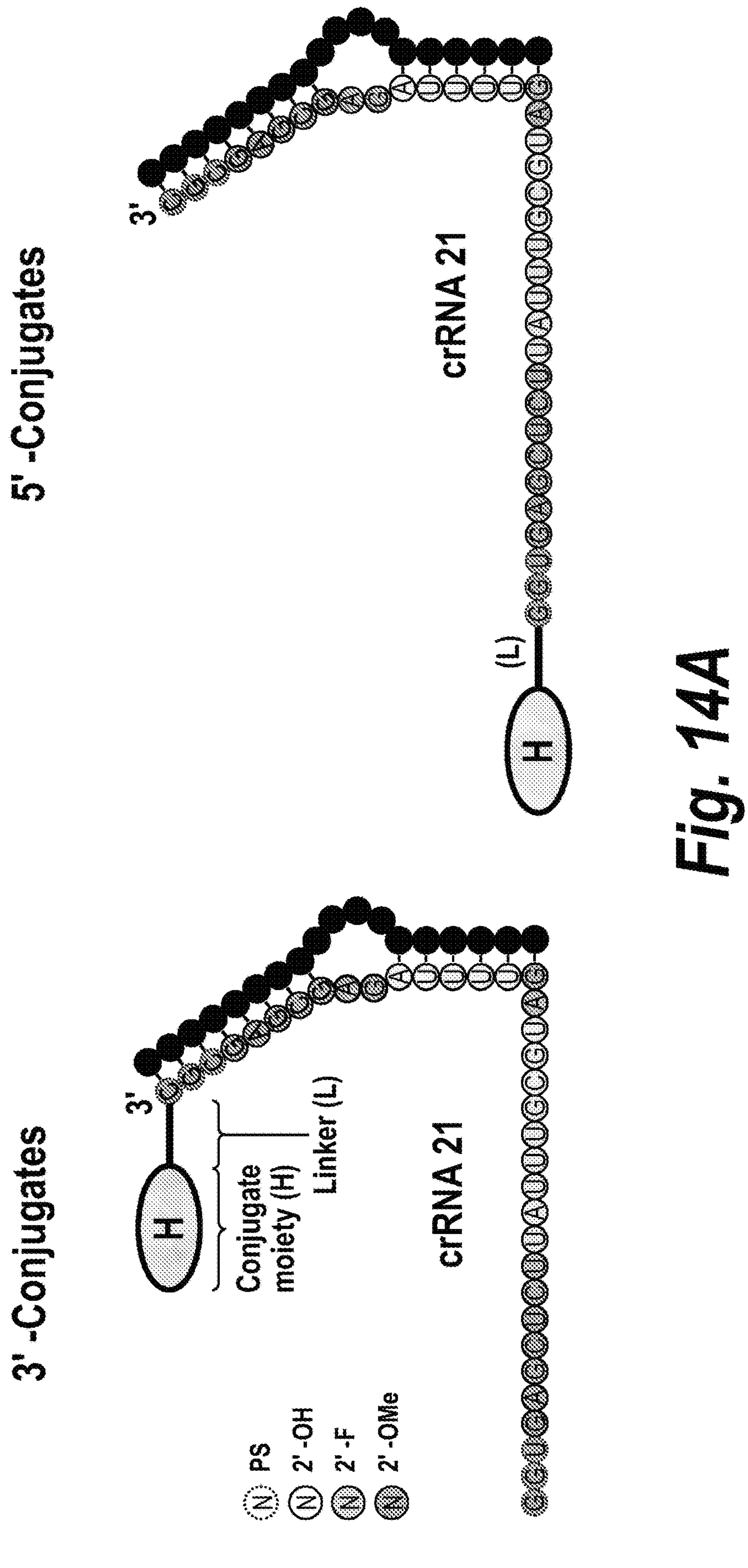
FIG. 14A-FIG. 14D depict schematics of chemically modified crRNAs and tracrRNAs with conjugates. The crRNA conjugates may be on the 5' or 3' end (FIG. 14A). The tracrRNA conjugates may be on the 5' or 3' end (FIG. 14B). The conjugates may be on both the 5' and the 3' end of the crRNA and the tracrRNA (FIG. 14C and FIG. 14D).
Figure 14B:
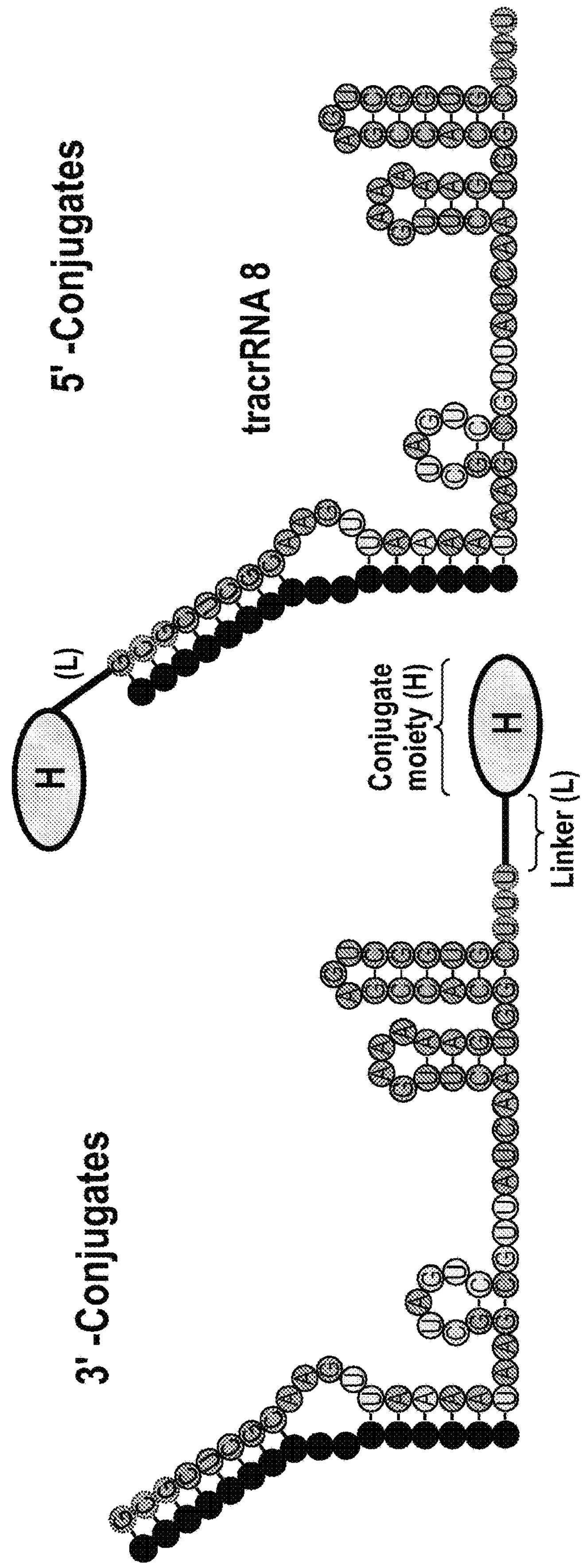
Figure 14C:
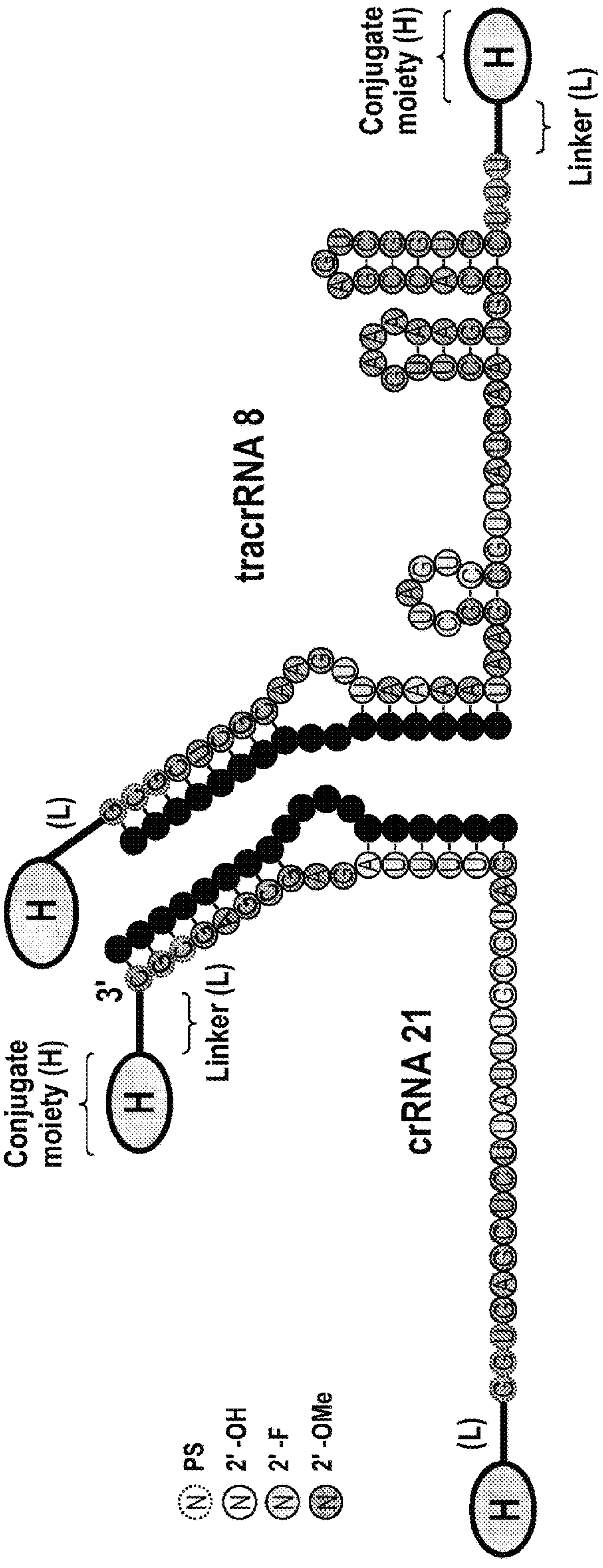
Figure 14D:
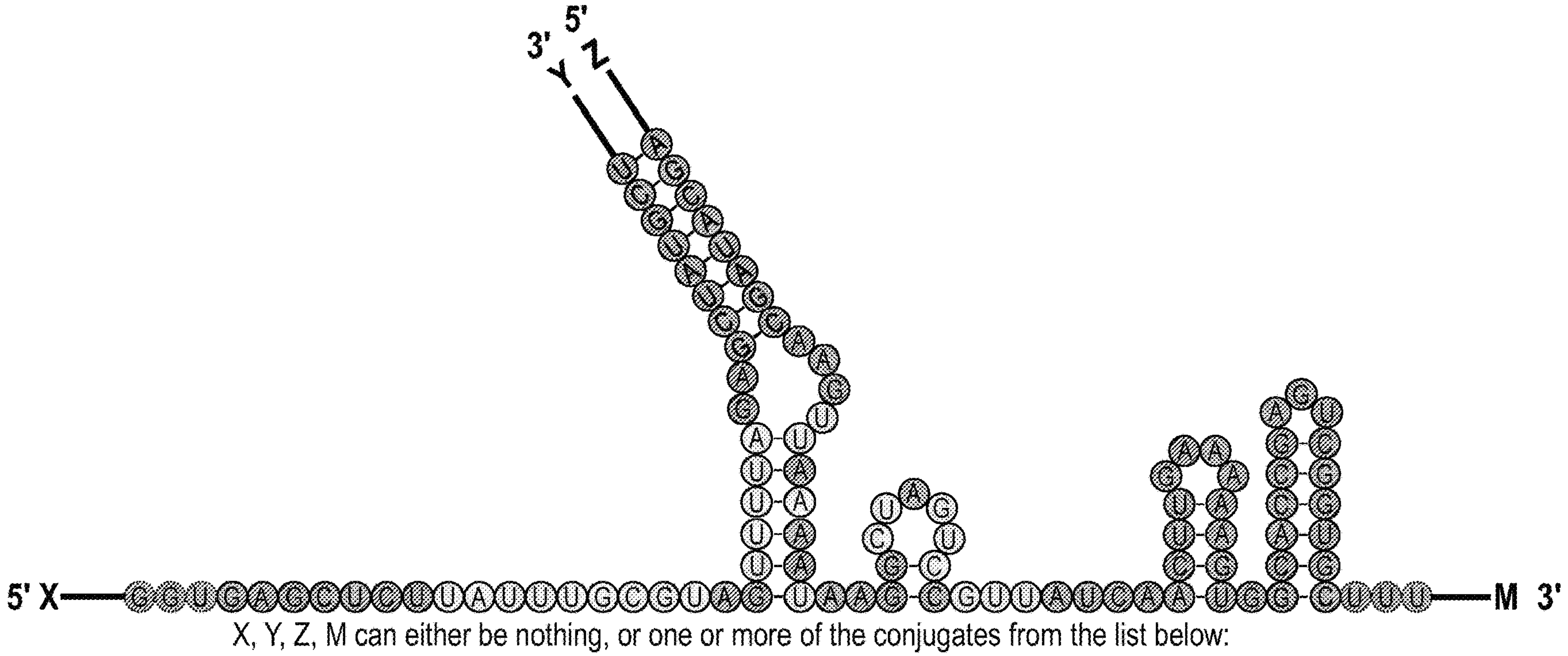

Example 4—Chemically Modified crRNA:TracrRNA Pairs with Modifications in the Repeat/Anti-Repeat Region It has previously been shown that crRNA and tracrRNA can be fused with a GAAA tetraloop to yield a single guide RNA (sgRNA) with enhanced efficacy. Given the possibility that repeat: anti-repeat interactions could affect efficacy, the pairing between the repeat and anti-repeat of crRNA and tracrRNA was explored. Modifications were made to the repeat and anti-repeat regions, including increasing the GC nucleotide content and using 2'-Fluoro modifications. Repeat/Anti-Repeat modified crRNAs (hiGC C1-C4) and tracrRNAs (hiGC T1-T4) were designed to improve pairing between crRNA and tracrRNA (Table 5). All of the modified RNAs outperformed in vitro-transcribed sgRNA as well as synthetic, unmodified dual RNAs (FIG. 10A and FIG. 10B). Furthermore, at lower concentrations, hiGC-C1 exhibit increased potency relative to non-optimized versions of unmodified or modified RNAs (FIG. 10A). However, this trend does not hold true in HTT-hiGC C1 at 3 μmol of the RNP (FIG. 12A), but does at 20 μmol of the RNP (FIG. 12B).

Example 5—Conjugation of Functional Moieties on Chemically Modified crRNAs and tracrRNAs Terminally (5' or 3' end) conjugated moieties such as fluorophores, N-Acetylgalactosamine (GalNAc), or Cholesterol-Triethylene glycol (TEGChol) were added to the crRNAs and the tracrRNAs to determine if the terminally conjugated moieties could be tolerated. Such modifications can be useful for microscopy, and for monitoring cellular or tissue-specific RNA uptake. 5'-Cy3 modifications were introduced on crRNAs C10 and C11 to yield C12 and C13, respectively (Table 5). TegChol or GalNAc was also covalently attached to the 3' end of C12 or C13 to obtain C14 and C15, respectively. Most crRNA conjugated moieties were tolerated on both ends, though some loss of function was observed with C13, C14 and C16 (FIG. 4). In contrast, C15 was essentially inactive. T5 containing a 3'-TegChol was also nonfunctional, not surprisingly given the 2'-OMe substitution at A15.

Terminally conjugated moieties may be placed on the 5' end, the 3' end, or both ends of a crRNA or tracrRNA as depicted in FIGS. 14A-14D and Table 4.

The terminally conjugated moieties may be used to increase cellular uptake of the RNAs. The conjugates may also be used to promote specific tissue distribution of the RNAs.

The terminally conjugated moieties may be selected from fatty acids, steroids, secosteroids, lipids, gangliosides and nucleoside analogs, endocannabinoids, vitamins, receptor ligands, peptides, aptamers, alkyl chains, fluorophores, antibodies, and nuclear localization signals.

The terminally conjugated moieties may be selected from cholesterol, docosahexaenoic acid (DHA), docosanoic acid (DCA), lithocholic acid (LA), GalNAc, amphiphilic block copolymer (ABC), hydrophilic block copolymer (HBC), poloxamer, Cy5, and Cy3.

Example 6—Modification Scanning of Heavily Modified tracrRNA T2

Figure 16A:
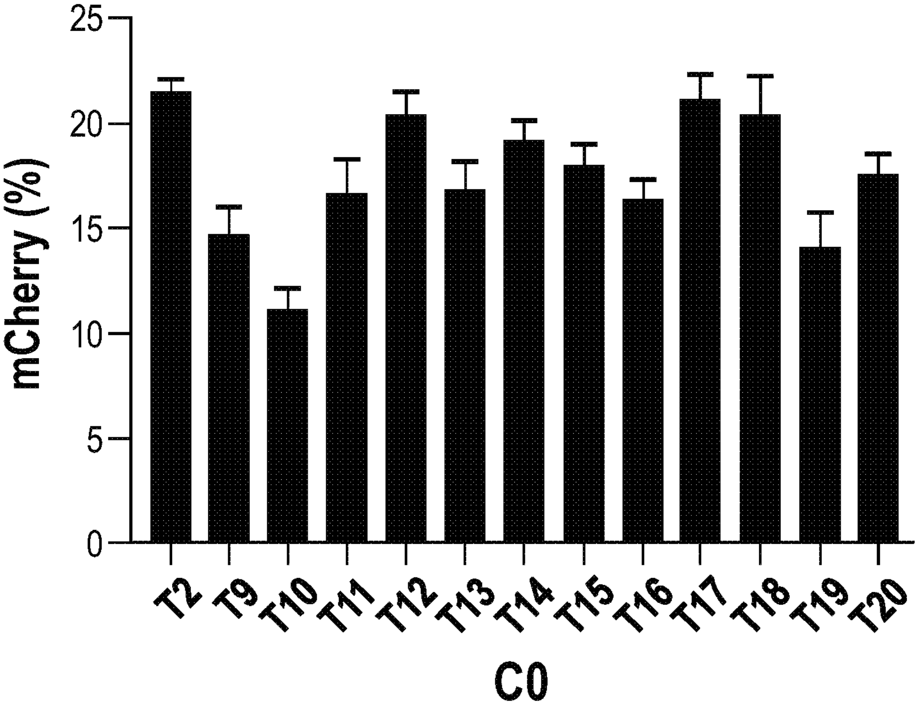
FIG. 16A-FIG. 16C depict several additional chemically modified tracrRNAs (T9-T20) tested in combination with the minimally modified crRNA C0 (FIG. 16A), the heavily modified crRNA C20 (FIG. 16B), and the fully modified crRNA C21 (FIG. 16C), to form chemically modified crRNA:tracrRNA pairs. The various crRNA:tracrRNA pairs were used in a HEK293T TLR assay to determine genome editing efficiency. Cells were transfected with 20 μmol of Cas9, crRNA, tracrRNA RNPs.
Figure 16B:
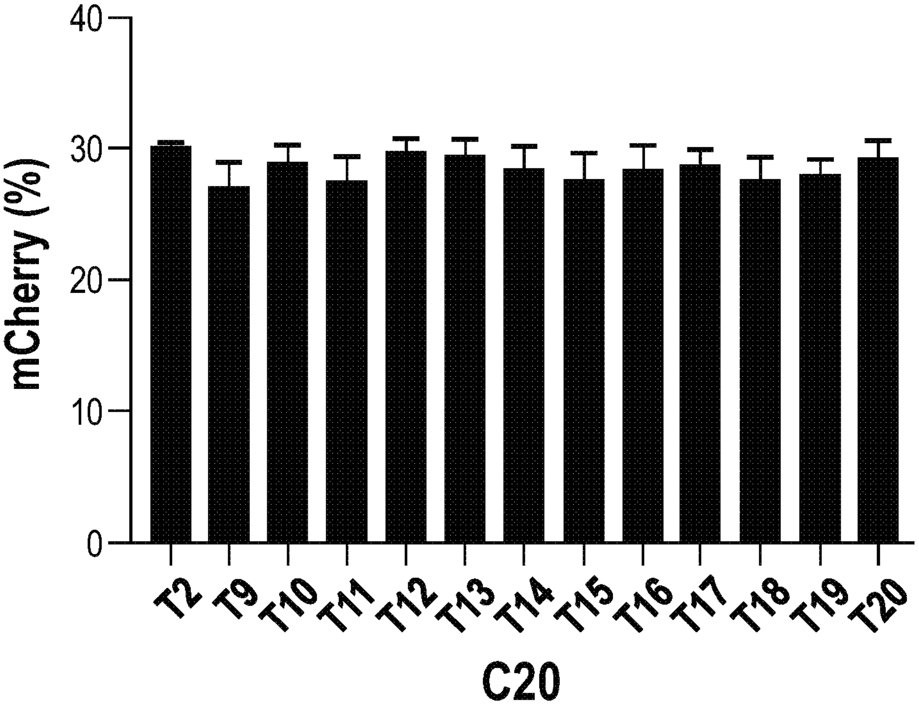
Figure 16C:
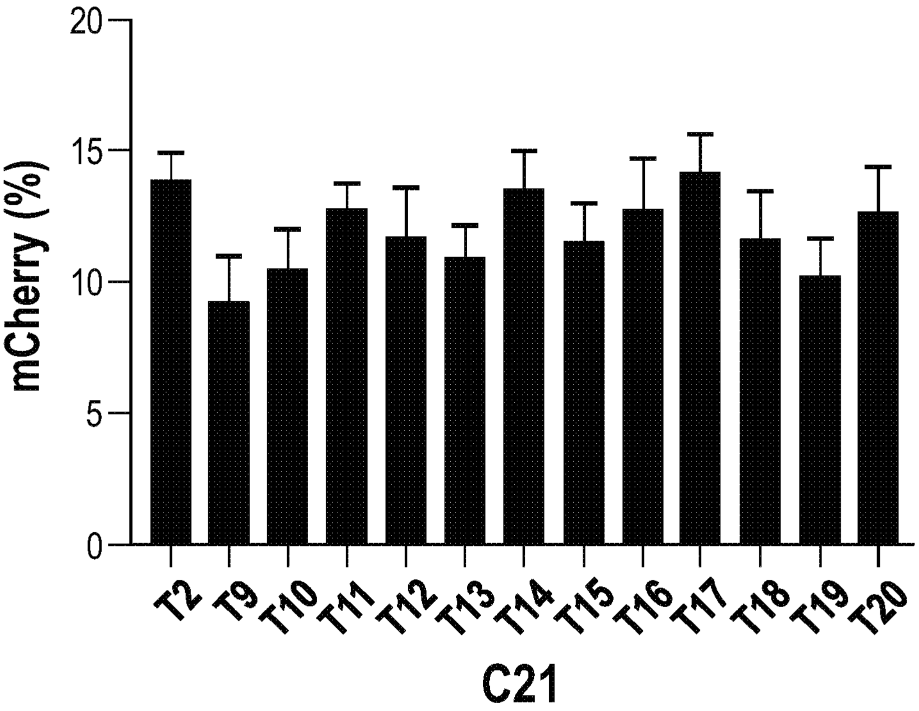

The tracrRNA T2 described above is heavily modified but still contains 12 unmodified (ribose) residues. The tracrRNA T8 described above replaces those 12 unmodified residues with 2'-Fluoro modifications to create a fully modified tracrRNA. Although both T2 and T8 are functional, T2 possess higher activity, indicating that one or more of the 12 2'-Fluoro modifications in T8, relative to T2, is causing the reduced activity in T8. In an effort to determine the one or more sites at which the 2'-Fluoro modification is deleterious, individual ribose residues from T2 where changed to 2'-Fluoro, one at a time. These 12 tracrRNAs (T9-T20) are shown in Table 1 above. T9-T20 were used with crRNAs C0, C20, C21 described above. The same HEK293T traffic light reporter (TLR) system was used as described above. As demonstrated in FIG. 16A-16C, no single ribose from among the 12 that remain in T2 is truly critical, suggesting that the reduction in activity in going from T2 to T8 is due to synergistic effects of multiple substitutions. Of note, the data of FIG. 16A-16C demonstrate that T9-T20 retain activity and provide additional support that the modifications are tolerated.

What is claimed:

1. A chemically modified guide RNA comprising:

(a) a CRISPR RNA (crRNA) portion comprising a 3' end, a 5' end, a guide sequence capable of hybridizing to a target polynucleotide sequence, and a repeat nucleotide sequence; and (b) a trans-activating CRISPR RNA (tracrRNA) portion comprising a 3' end, a 5' end, and an anti-repeat nucleotide sequence that is complementary to the repeat nucleotide sequence, wherein at least 80% of the nucleotides of the chemically modified guide RNA comprise a chemical modification, wherein in the crRNA portion:

the nucleotides at positions 1 and 4 and at least two nucleotides selected from the group consisting of the nucleotides at positions 2, 3, 5-10, 20, 21, and 27-36 from the 5' end comprise a 2'-O-methyl chemical modification, the nucleotides at positions 11 and 12 from the 5' end comprise a 2'-fluoro chemical modification, and at least two nucleotides selected from the group consisting of the nucleotides at positions 13, 14, 17, 18, 25, and 26 from the 5' end comprise a chemical modification that is not a 2'-O-methyl chemical modification; and wherein at least two nucleotides selected from the group consisting of the nucleotides at positions 1-11, 14, 16, 17, 19-22, 25, 29, and 33-67 from the 5' end of the tracrRNA portion comprise a 2'-O-methyl chemical modification.

2. The chemically modified guide RNA of claim 1, wherein the at least two nucleotides selected from the group consisting of the nucleotides at positions 13, 14, 17, 18, 25, and 26 from the 5' end and comprising the chemical modification that is not 2'-O-methyl independently comprise a modification of a ribose group, a phosphate group, or a nucleobase, or a combination thereof.

3. The chemically modified guide RNA of claim 2, wherein the modification of the ribose group is selected from the group consisting of 2'-fluoro, 2'-deoxy, 2'-O-(2-methoxyethyl) (MOE), 2'-$NH_2$, and a bicyclic nucleotide selected from the group consisting of a locked nucleic acid (LNA), a 2'-(S)-constrained ethyl (S-cEt), a constrained MOE, and a 2'-0,4'-C-aminomethylene bridged nucleic acid (2',4'-$BNA^{NC}$).

4. The chemically modified guide RNA of claim 2, wherein:

at least 80% of the ribose groups of the chemically modified guide RNA are chemically modified;

the modification of the phosphate group is selected from the group consisting of a phosphorothioate, a phosphonoacetate (PACE), a thiophosphonoacetate (thioPACE), an amide, a triazole, a phosphonate, and a phosphotriester modification; or the modification of the nucleobase is selected from the group consisting of 2-thiouridine, 4-thiouridine, $N^6$-methyladenosine, pseudouridine, 2,6-diaminopurine, inosine, thymidine, 5-methylcytosine, 5-substituted pyrimidine, isoguanine, isocytosine, and a halogenated aromatic group.

5. The chemically modified guide RNA of claim 1, wherein at least 90% or 100% of the nucleotides present in the crRNA and tracrRNA portions comprise a chemical modification.

6. The chemically modified guide RNA of claim 1, wherein:

at least two nucleotides selected from the group consisting of the nucleotides at positions 13, 14, 17, 18, 25, and 26 from the 5' end of the crRNA portion comprise a 2'-fluoro chemical modification; or at least two nucleotides selected from the group consisting of the nucleotides at positions 18, 23, 24, 27, and 28 from the 5' end of the tracrRNA portion comprise a 2'-fluoro chemical modification.

7. The chemically modified guide RNA of claim 6, wherein all the nucleotides at positions 11-14, 17, 18, 25, and 26 from the 5' end of the crRNA portion are 2'-fluoro modified nucleotides.

8. The chemically modified guide RNA of claim 6, wherein all the nucleotides at positions 18, 23, 24, 27, and 28 from the 5' end of the tracrRNA portion are 2'-fluoro modified nucleotides.

9. The chemically modified guide RNA of claim 1, wherein the crRNA portion has a modification pattern of:

mN#mN#mN#mNmNmNmNmNmNmNfNfNfNfNrN#rN#fNfNrN#mNmGrU#rU#rU#fUfAmG mAmGmCmUmAmU#mG#mC#mU (crRNA 20) (SEQ ID NO: 10);

mN#mN#mN#mNmNmNmNmNmNmNfNfNfNfNfNfNfNfNmNmGfUfUfUfUfAmGmAmG mCmUmAmU#mG#mC#mU (crRNA 21) (SEQ ID NO: 11); or mN#mN#mN#mNmNmNmNmNmNmNfNfNfNfNrN#rN#fNfNrN#mNmGfUrU#fUfUfAmGm AmGmCmUmAmU#mG#mC#mU (crRNA 22) (SEQ ID NO: 12); and the tracrRNA portion has a modification pattern of:

mA#mG#mC#mAmUmAmGmCmAmAmGrUrUmAr AmAmArUmAmAmGmGrCrUmArGrUr CmCrGrU-rUmAmUmCmAmAmCmUmUmGmAmAmAmA-mAmGmUmGmGmCmAmCmCm GmAmGmUmCmGmGmUmGmC#mU#mU#mU (tracrRNA 2) (SEQ ID NO: 13);

mA#mG#mC#mAmUmAmGmCmAmAmGrU#rU#m ArA#mAmArU#mAmAmGmGrC#rU#m ArG#rU#rC#mCrG#rU#rU#mAmUmCmAmAmCm UmUmGmAmAmAmAmAmGmUmGmG mCmAm-CmCmGmAmGmUmCmGmGmUmGmC# mU#mU#mU (tracrRNA 3) (SEQ ID NO: 14);

mA#mG#mC#mAmUmAmGmCmAmAmGrUrUmAm AmAmArUmAmAmGmGrCrUmArGrU rCmCrGrU-rUmAmUmCmAmAmCmUmUmGmAmAmAmA-mAmGmUmGmGmCmAmCmC mGmAmGmUmCmGmGmUmGmC#mU#mU#mU (tracrRNA 4) (SEQ ID NO: 15);

mA#mG#mC#mAmUmAmGmCmAmAmGrUrUmAr AmAmAfUmAmAmGmGfCfUmArGfUf CmCrGrU-rUmAmUmCmAmAmCmUmUmGmAmAmAmA-mAmGmUmGmGmCmAmCmCm GmAmGmUmCmGmGmUmGmC#mU#mU#mU (tracrRNA 6) (SEQ ID NO: 16);

mA#mG#mC#mAmUmAmGmCmAmAmGrUfUmAr AmAmAfUmAmAmGmGfCfUmAfGfUf CmCrGrU-rUmAmUmCmAmAmCmUmUmGmAmAmAmA-mAmGmUmGmGmCmAmCmCm GmAmGmUmCmGmGmUmGmC#mU#mU#mU (tracrRNA 7) (SEQ ID NO: 17);

mA#mG#mC#mAmUmAmGmCmAmAmGfUfUmA fAmAmAfUmAmAmGmGfCfUmAfGfUf CmCfGfU-fUmAmUmCmAmAmCmUmUmGmAmAmAmA-mAmGmUmGmGmCmAmCmCm GmAmGmUmCmGmGmUmGmC#mU#mU#mU (tracrRNA 8) (SEQ ID NO: 18);

mA#mG#mC#mAmUmAmGmCmAmAmGfUrUmAr AmAmArUmAmAmGmGrCrUmArGrUr CmCrGrU-rUmAmUmCmAmAmCmUmUmGmAmAmAmA-mAmGmUmGmGmCmAmCmCm GmAmGmUmCmGmGmUmGmC#mU#mU#mU (tracrRNA 9) (SEQ ID NO: 19);

mA#mG#mC#mAmUmAmGmCmAmAmGrUfUmAr AmAmArUmAmAmGmGrCrUmArGrUr CmCrGrU-rUmAmUmCmAmAmCmUmUmGmAmAmAmA-mAmGmUmGmGmCmAmCmCm GmAmGmUmCmGmGmUmGmC#mU#mU#mU (tracrRNA 10) (SEQ ID NO: 20);

mA#mG#mC#mAmUmAmGmCmAmAmGrUrUmAf AmAmArUmAmAmGmGrCrUmArGrUr CmCrGrU-rUmAmUmCmAmAmCmUmUmGmAmAmAmA-mAmGmUmGmGmCmAmCmCm GmAmGmUmCmGmGmUmGmC#mU#mU#mU (tracrRNA 11) (SEQ ID NO: 21);

mA#mG#mC#mAmUmAmGmCmAmAmGrUrUmAr AmAmAfUmAmAmGmGrCrUmArGrUr CmCrGrU-rUmAmUmCmAmAmCmUmUmGmAmAmAmA-mAmGmUmGmGmCmAmCmCm GmAmGmUmCmGmGmUmGmC#mU#mU#mU (tracrRNA 12) (SEQ ID NO: 22);

mA#mG#mC#mAmUmAmGmCmAmAmGrUrUmAr AmAmArUmAmAmGmGfCrUmArGrUr CmCrGrU-rUmAmUmCmAmAmCmUmUmGmAmAmAmA-mAmGmUmGmGmCmAmCmCm GmAmGmUmCmGmGmUmGmC#mU#mU#mU (tracrRNA 13) (SEQ ID NO: 23);

mA#mG#mC#mAmUmAmGmCmAmAmGrUrUmAr AmAmArUmAmAmGmGrCfUmArGrUr CmCrGrU-rUmAmUmCmAmAmCmUmUmGmAmAmAmA-mAmGmUmGmGmCmAmCmCm GmAmGmUmCmGmGmUmGmC#mU#mU#mU (tracrRNA 14) (SEQ ID NO: 24);

mA#mG#mC#mAmUmAmGmCmAmAmGrUrUmAr AmAmArUmAmAmGmGrCrUmAfGrUr CmCrGrU-rUmAmUmCmAmAmCmUmUmGmAmAmAmA-mAmGmUmGmGmCmAmCmCm GmAmGmUmCmGmGmUmGmC#mU#mU#mU (tracrRNA 15) (SEQ ID NO: 25);

mA#mG#mC#mAmUmAmGmCmAmAmGrUrUmAr AmAmArUmAmAmGmGrCrUmArGfUr CmCrGrU-rUmAmUmCmAmAmCmUmUmGmAmAmAmA-mAmGmUmGmGmCmAmCmCm GmAmGmUmCmGmGmUmGmC#mU#mU#mU (tracrRNA 16) (SEQ ID NO: 26);

mA#mG#mC#mAmUmAmGmCmAmAmGrUrUmAr AmAmArUmAmAmGmGrCrUmArGrUf CmCrGrU-rUmAmUmCmAmAmCmUmUmGmAmAmAmA-mAmGmUmGmGmCmAmCmCm GmAmGmUmCmGmGmUmGmC#mU#mU#mU (tracrRNA 17) (SEQ ID NO: 27);

mA#mG#mC#mAmUmAmGmCmAmAmGrUrUmAr AmAmArUmAmAmGmGrCrUmArGrUr CmCfGrU-rUmAmUmCmAmAmCmUmUmGmAmAmAmA-mAmGmUmGmGmCmAmCmCm GmAmGmUmCmGmGmUmGmC#mU#mU#mU (tracrRNA 18) (SEQ ID NO: 28);

mA#mG#mC#mAmUmAmGmCmAmAmGrUrUmAr AmAmArUmAmAmGmGrCrUmArGrUr CmCrGfU-rUmAmUmCmAmAmCmUmUmGmAmAmAmA-mAmGmUmGmGmCmAmCmCm GmAmGmUmCmGmGmUmGmC#mU#mU#mU (tracrRNA 19) (SEQ ID NO: 29); or mA#mG#mC#mAmUmAmGmCmAmAmGrUrUmAr AmAmArUmAmAmGmGrCrUmArGrUr CmCrGrU-fUmAmUmCmAmAmCmUmUmGmAmAmAmA-mAmGmUmGmGmCmAmCmCm GmAmGmUmCmGmGmUmGmC#mU#mU#mU (tracrRNA 20) (SEQ ID NO: 30), wherein rN=RNA, mN=2'-O-methyl RNA, fN=2'-fluoro RNA, N#N=phosphorothioate linkage, and N=any nucleotide.

10. The chemically modified guide RNA of claim 1, wherein the chemically modified guide RNA binds to a Cas9 nuclease selected from the group consisting of *S. pyogenes* Cas9 (SpCas9), *S. aureus* Cas9 (SaCas9), *N. meningitidis* Cas9 (NmCas9), *C. jejuni* Cas9 (CjCas9), and *Geobacillus* Cas9 (GeoCas9).

11. The chemically modified guide RNA of claim 1, further comprising a nucleotide or non-nucleotide loop or linker linking the 3' end of the crRNA portion to the 5' end of the tracrRNA portion.

12. The chemically modified guide RNA of claim 1, wherein all the nucleotides at positions 1-12, 20, 21, and 27-36 from the 5' end of the crRNA portion each independently comprises a chemical modification.

13. The chemically modified guide RNA of claim 1, wherein all the nucleotides at positions 1-11, 14, 16, 17, 19-22, 25, 29, and 33-67 from the 5' end of the tracrRNA portion are 2'-O-methyl chemical modified nucleotides.

14. The chemically modified guide RNA of claim 1, wherein the crRNA portion is 36 nucleotides long and the tracrRNA portion is 67 nucleotides long.

15. A modified guide RNA comprising:

(a) a CRISPR RNA (crRNA) portion comprising a 3' end, a 5' end, a guide sequence capable of hybridizing to a target polynucleotide sequence, and a repeat nucleotide sequence; and (b) a trans-activating CRISPR RNA (tracrRNA) portion comprising an anti-repeat nucleotide sequence that is complementary to the repeat nucleotide sequence, wherein the modified guide RNA comprises an increased GC nucleotide content in the repeat nucleotide sequence and the anti-repeat nucleotide sequence relative to an unmodified guide RNA, wherein in the crRNA portion:

the nucleotides at positions 1 and 4 and at least two nucleotides selected from the group consisting of the nucleotides at positions 2, 3, 5-10, 20, 21, and 27-36 from the 5' end comprise a 2'-O-methyl chemical modification, the nucleotides at positions 11 and 12 from the 5' end comprise a 2'-fluoro chemical modification, and at least two nucleotides selected from the group consisting of the nucleotides at positions 13, 14, 17, 18, 25, and 26 from the 5' end comprise a chemical modification that is not a 2'-O-methyl chemical modification; and wherein at least two nucleotides selected from the group consisting of the nucleotides at positions 1-11, 14, 16, 17, 19-22, 25, 29, and 33-67 from the 5' end of the tracrRNA portion comprise a 2'-O-methyl chemical modification.

16. The modified guide RNA of claim 15, comprising:

ribose modifications in the repeat nucleotide sequence and the anti-repeat nucleotide sequence; or the modified guide RNA wherein the modifications of the repeat nucleotide sequence and the anti-repeat nucleotide sequence enhance the stability of pairing between the crRNA portion and the tracrRNA portion.

17. The modified guide RNA of claim 15, wherein the crRNA portion comprises the nucleotide sequence NNNNNNNNNNNNNNNNNNNNGUUUUA-GAGCGAGCGC (SEQ ID NO: 31) and the tracrRNA portion comprises the nucleotide sequence GCG-CUCGCAAGUUAAAAUAAGGCUAGUCCGUUAU-CAACUUGAAAAAGUGGCACC GAGUCGGUGCUUU (SEQ ID NO: 32), wherein N=any nucleotide.

18. The modified guide RNA of claim 15, wherein the at least two chemical modifications that are not 2'-O-methyl chemical modifications independently comprise a modification of a ribose group, a phosphate group, or a nucleobase, or a combination thereof, wherein the modification of the ribose group is selected from the group consisting of 2'-fluoro, 2'-deoxy, 2'-O-(2-methoxyethyl) (MOE), 2'-$NH_2$, and a bicyclic nucleotide selected from the group consisting of a locked nucleic acid (LNA), 2'-(S)-constrained ethyl (S-cEt), constrained MOE, and a 2'-0,4'-C-aminomethylene bridged nucleic acid (2',4'-$BNA^{NC}$).

19. A modified guide RNA comprising:

(a) a CRISPR RNA (crRNA) portion comprising (i) a guide sequence capable of hybridizing to a target polynucleotide sequence, and (ii) a repeat nucleotide sequence; and (b) a trans-activating CRISPR RNA (tracrRNA) portion comprising an anti-repeat nucleotide sequence that is complementary to the repeat nucleotide sequence, wherein the repeat nucleotide sequence and the anti-repeat nucleotide sequence increase binding affinity between the repeat nucleotide sequence and the anti-repeat nucleotide sequence relative to an unmodified guide RNA, and wherein the crRNA portion has modified guide RNA comprises a modification pattern of mN#mN#mN#mNmNmNmNmNmNmNfNfNfNfN rN#rN#fNfNrN#mNmGrU#rU#rU#fUfAmG mAmGmCmGmAmG#mC#mG#mC (hiGC crRNA 1) (SEQ ID NO: 33); and/or wherein the tracrRNA portion has a modification pattern of mG#mC#mG#mCmUmCmGmCmAmAmGrUrUm ArAmAmArUmAmAmGmGrCrUmArGrUr CmCr-GrUrUmAmUmCmAmAmCmUmUmGmAmAmA-mAmAmGmUmGmGmCmAmCmCm GmAmGmUmCmGmGmUmGmC#mU#mU#mU (hiGC tracrRNA 1) (SEQ ID NO: 37), wherein rN=RNA, mN=2'-O-methyl RNA, fN=2'-fluoro RNA, N#N=phosphorothioate linkage, and N=any nucleotide.

20. A method of altering expression of a target gene in a cell, comprising contacting the cell with a genome editing system comprising:

an RNA-guided nuclease or a polynucleotide encoding an RNA-guided nuclease; and a chemically modified guide RNA comprising:

(a) a CRISPR RNA (crRNA) portion comprising a 3' end, a 5' end, a guide sequence capable of hybridizing to a target polynucleotide sequence, and a repeat nucleotide sequence; and (b) a trans-activating CRISPR RNA (tracrRNA) portion comprising a 3' end, a 5' end, and an anti-repeat nucleotide sequence that is complementary to the repeat nucleotide sequence; wherein at least 80% of the nucleotides of the chemically modified guide RNA comprise a chemical modification, wherein in the crRNA portion:

the nucleotides at positions 1 and 4 and at least two nucleotides selected from the group consisting of the nucleotides at positions 2, 3, 5-10, 20, 21, and 27-36 from the 5' end comprise a 2'-O-methyl chemical modification, the nucleotides at positions 11 and 12 from the 5' end comprise a 2'-fluoro chemical modification, and at least two nucleotides selected from the group consisting of the nucleotides at positions 13, 14, 17, 18, 25, and 26 from the 5' end comprise a chemical modification that is not a 2'-O-methyl chemical modification; and wherein at least two nucleotides selected from the group consisting of the nucleotides at positions 1-11, 14, 16, 17, 19-22, 25, 29, and 33-67 from the 5' end of the tracrRNA portion each comprise a 2'-O-methyl chemical modification.

21. The method of claim 20, wherein:

expression of the target gene is knocked out or knocked down;

a sequence of the target gene is modified, edited, corrected, or enhanced;

the polynucleotide encoding an RNA-guided nuclease comprises a synthetic mRNA or a vector;

the chemically modified guide RNA and the RNA-guided nuclease comprise a ribonucleoprotein (RNP) complex; or the RNA-guided nuclease is selected from the group consisting of *S. pyogenes* Cas9 (SpCas9), *S. aureus* Cas9 (SaCas9), *N. meningitidis* Cas9 (NmCas9), *C. jejuni* Cas9 (CjCas9), and *Geobacillus* Cas9 (GeoCas9).

22. A CRISPR genome editing system comprising:

an RNA-guided nuclease or a polynucleotide encoding an RNA-guided nuclease; and a chemically modified guide RNA comprising:

(a) a CRISPR RNA (crRNA) portion comprising a 3' end, a 5' end, a guide sequence capable of hybridizing to a target polynucleotide sequence, and a repeat nucleotide sequence; and (b) a trans-activating CRISPR RNA (tracrRNA) portion comprising a 3' end, a 5' end, and an anti-repeat nucleotide sequence that is complementary to the repeat nucleotide sequence; and wherein at least 80% of the nucleotides of the chemically modified guide RNA comprise a chemical modification, wherein in the crRNA portion:

the nucleotides at positions 1 and 4 and at least two nucleotides selected from the group consisting of the nucleotides at positions 2, 3, 5-10, 20, 21, and 27-36 from the 5' end comprise a 2'-O-methyl chemical modification, the nucleotides at positions 11 and 12 from the 5' end comprise a 2'-fluoro chemical modification, and at least two nucleotides selected from the group consisting of the nucleotides at positions 13, 14, 17, 18, 25, and 26 from the 5' end comprise a chemical modification that is not a 2'-O-methyl chemical modification; and wherein at least two nucleotides selected from the group consisting of the nucleotides at positions 1-11, 14, 16, 17, 19-22, 25, 29, and 33-67 from the 5' end of the tracrRNA portion each comprise a 2'-O-methyl chemical modification.

23. The CRISPR genome editing system of claim 22, wherein:

at least 80% of ribose groups of the chemically modified guide RNA are chemically modified; or the at least two chemical modifications that are not 2'-O-methyl chemical modifications each independently comprises a modification in a ribose group, a phosphate group, or a nucleobase, or a combination thereof, wherein the modification of the ribose group is selected from the group consisting of 2'-fluoro, 2'-deoxy, 2'-O-(2-methoxyethyl) (MOE), 2'-$NH_2$, and a bicyclic nucleotide selected from the group consisting of a locked nucleic acid (LNA), a 2'-(S)-constrained ethyl (S-cEt), a constrained MOE, and a 2'-0,4'-C-aminomethylene bridged nucleic acid (2',4'-$BNA^{NC}$).

24. The CRISPR genome editing system of claim 22, wherein at least 90% or 100% of the nucleotides present in the crRNA and tracrRNA portions are chemically modified.

25. The CRISPR genome editing system of claim 22, wherein the RNA-guided nuclease is selected from the group consisting of *S. pyogenes* Cas9 (SpCas9), *S. aureus* Cas9 (SaCas9), *N. meningitidis* Cas9 (NmCas9), *C. jejuni* Cas9 (CjCas9), and *Geobacillus* Cas9 (GeoCas9).

26. A chemically modified guide RNA comprising:

(a) a CRISPR RNA (crRNA) portion comprising a 3' end, a 5' end, a guide sequence capable of hybridizing to a target polynucleotide sequence, and a repeat nucleotide sequence; and (b) a trans-activating CRISPR RNA (tracrRNA) portion comprising a 3' end, a 5' end, and an anti-repeat nucleotide sequence that is complementary to the repeat nucleotide sequence, wherein the chemically modified guide RNA comprises fully chemically modified nucleotides, wherein in the crRNA portion:

the nucleotides at positions 1 and 4 from the 5' end and at least two nucleotides selected from the group consisting of the nucleotides at positions 2, 3, 5-10, 20, 21, and 27-36 from the 5' end comprise a 2'-O-methyl chemical modification, and the nucleotides at positions 11 and 12 from the 5' end comprise a 2'-fluoro chemical modification; and wherein in the tracrRNA portion:

at least two nucleotides selected from the group consisting of the nucleotides at positions 1-11, 14, 16, 17, 19-22, 25, 29, and 33-67 from the 5' end comprise a 2'-O-methyl chemical modification, and at least two nucleotides selected from the group consisting of the nucleotides at positions 18, 23, 24, 27, and 28 from the 5' end of the tracrRNA portion comprise a chemical modification that is not a 2'-O-methyl chemical modification.

27. The chemically modified guide RNA of claim 26, wherein all ribose groups of the modified guide RNA are chemically modified.

* * * * *